US008021658B2

(12) United States Patent
Wong

(10) Patent No.: US 8,021,658 B2
(45) Date of Patent: Sep. 20, 2011

(54) ALTERNATIVE SPLICE FORMS OF PROTEINS AS BASIS FOR MULTIPLE THERAPEUTIC MODALITIES

(75) Inventor: Albert J. Wong, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 800 days.

(21) Appl. No.: 10/156,932

(22) Filed: May 28, 2002

(65) Prior Publication Data

US 2003/0069181 A1 Apr. 10, 2003

Related U.S. Application Data

(60) Provisional application No. 60/293,791, filed on May 25, 2001.

(51) Int. Cl.
*A61K 39/00* (2006.01)
*A01N 63/02* (2006.01)
(52) U.S. Cl. .................................. 424/93.71; 424/277.1
(58) Field of Classification Search .................. None
See application file for complete search history.

(56) References Cited

U.S. PATENT DOCUMENTS

| | | | | |
|---|---|---|---|---|
| 5,212,290 A | 5/1993 | Vogelstein et al. | ......... | 530/387.7 |
| 5,401,828 A | 3/1995 | Vogelstein et al. | ........... | 530/300 |
| 5,662,907 A | 9/1997 | Kubo et al. | ................ | 424/185.1 |
| 5,710,010 A | 1/1998 | Vogelstein et al. | .......... | 435/7.23 |
| 5,726,152 A | 3/1998 | Bayne et al. | ..................... | 514/12 |
| 5,814,317 A | 9/1998 | Vogelstein et al. | ........ | 424/143.1 |
| 5,894,018 A | 4/1999 | Davila et al. | ............. | 424/195.11 |
| 5,981,725 A | 11/1999 | Vogelstein et al. | .......... | 536/23.5 |
| 5,993,823 A * | 11/1999 | Boutillon et al. | .......... | 424/208.1 |
| 5,994,300 A | 11/1999 | Bayne et al. | ..................... | 514/12 |
| 6,046,380 A * | 4/2000 | Clark | .............................. | 800/14 |
| 6,077,519 A * | 6/2000 | Storkus et al. | ............. | 424/277.1 |
| 6,127,126 A | 10/2000 | Vogelstein et al. | ............... | 435/6 |
| 6,224,868 B1 | 5/2001 | Wong et al. | ................ | 424/185.1 |
| 6,361,946 B1 | 3/2002 | Alitalo et al. | ..................... | 435/6 |
| 6,488,932 B1 * | 12/2002 | Boon et al. | ................. | 424/185.1 |
| 6,805,865 B1 * | 10/2004 | Holaday et al. | ............ | 424/185.1 |
| 2003/0206905 A1 * | 11/2003 | Jakobovits et al. | ........ | 424/145.1 |

FOREIGN PATENT DOCUMENTS

| | | |
|---|---|---|
| CA | 2168988 | 2/1995 |
| WO | WO 96/16988 | 6/1996 |
| WO | WO 00/53219 | 9/2000 |
| WO | WO03/084467 | * 10/2004 |

OTHER PUBLICATIONS

Le Fur et al (PNAS, 1997, vol. 94, pp. 7561-7565).*
Le Fur et al (PNAS, 1997, vol. 94, pp. 5332-5337).*
Abstract of Wheeler (Salud p'ublica de M'exico, (Jul.-Aug. 1997) 39 (4) 283-7).*
Efferson et al (Anticancer Research, 2005, vol. 25, pp. 715-724).*
Bachman et al (Journal of Immunology, 2005, vol. 175, pp. 4677-4685).*
Verma et al (Nature, 1997, vol. 389, pp. 239-242).*
Eck et al (Gene-Based Therapy, In: The Pharmacological Basis of Therapeutics, Goodman and Gilman, Ed.s, 1996, pp. 77-101).*
Orkin et al ( "Report and Recommendation of the Panel to Assess the NIH Investment in Research on Gene Therapy", NIH, 1995).*
Harrison's Principles of Internal Medicine, 13th Edition, 1994, p. 1904.*
Hoffman et al (International J of Cancer, 2005, vol. 115, pp. 98-104).*
Paul, Fundamental Immunology, (text), 1993, pp. 1158-1170.*
Finke et al, Immunology Today, 1999, vol. 20, pp. 158-160.*
Apostolopoulos et al (Nature Medicine, 1998, vol. 4, pp. 315-320).*
Jager et al (PNAS, 2000, vol. 97, pp. 12198-12203).*
Semino et al (Journal of Biological Regulators and Homeostatic Agents, 1993, vol. 7, pp. 99-105).*
Abstract of Algarra et al International Journal of Clinical and Laboratory Research, 1997, vol. 27, pp. 95-102).*
Bodey et al (Anticancer Research, Jul.-Aug. 2000, vol. 20, pp. 2665-2676).*
Lauritzsen et al (International Journal of Cancer, 1998, vol. 78, pp. 216-222).*
Ohlen et al (Journal of Immunology, 2001, vol. 166, pp. 2863-2870).*
Antoinia et al (International Immunology, 1995, vol. 7, pp. 715-725).*
Yu and Restifo (Journal of Clinical Investigation, 2002, vol. 110, pp. 289-294, especially p. 292).*
Lee et al (Journal of Immunology, 1999, vol. 163, pp. 6292-6300).*
Abbas et al, Cellular and Molecular Immunology, 1991, p. 121, first column, first full paragraph.*
Chang et al, Journal of Experimental Medicine, 1999, vol. 189, pp. 483-491).*
Martin et al, Nature Genetics, 2002, vol. 31, pp. 429-434.*
Fayolle et al (Journal of Immunology, 1991, vol. 147, pp. 4069-4073).*
Nossal, Annual Review in Immunology, 1983, vol. 1, pp. 33-62.*
Sabin et al, JAMA, 1984, vol. 251, pp. 2988-2993.*
Lycke et al, Sandinavian Journal of Immunology, 1987, vol. 25, pp. 407-412.*
Smith et al (Immunology, 2002, vol. 106, pp. 144-158).*
C. Joynes, et al., "Alternative Splice Forms of VEGF family as the Basis for Anti-Tumor Vaccines" *Neuro-Oncology*, Oct. 2001, pp. 315.
Cécile Gouttefangeas, et al., "Problem Solving for Tumor Immunotherapy," *Nature Biotechnology*, vol. 18, May 2000, pp. 491-492.
I. Dralyuk, et al., "ASDB: Database of Alternatively Spliced Genes," *Nucleic Acid Research*, vol. 28, No. 1, 2000, pp. 296-297.

(Continued)

*Primary Examiner* — Karen Canella
(74) *Attorney, Agent, or Firm* — Drinker Biddle & Reath LLP

(57) ABSTRACT

Peptides or antibodies derived from alternative splice forms of proteins associated with a disease or physiologic condition are used as therapeutic or prophylactic agents. Peptides and antibodies derived from alternative splice forms of the vascular endothelial growth factor (VEGF) family of proteins are particularly useful in preventing or delaying the onset of tumors and inducing tumor regression.

38 Claims, 5 Drawing Sheets

OTHER PUBLICATIONS

J. Mendelsohn, "The epidermal growth factor receptor as a target for therapy with antireceptor monoclonal antibodies," *Seminars in Cancer Biology*, vol. 1, 1990, pp. 339-344.

David Berd, "Cancer Vaccines: Reborn or Just Recycled?," *Seminars in Oncology*, vol. 25, No. 6, Dec. 1998, pp. 605-610.

David K. Moscatello, et al., "A Naturally Occurring Mutant Human Epidermal Growth Factor Receptor as a Target for Peptide Vaccine Immunotherapy of Tumors," *Cancer Research*, vol. 57, Apr. 15, 1997, pp. 1419-1424.

Robert H. Oakley, et al., "The Dominant Negative Activity of the Human Glucocorticoid Receptor beta Isoform," *J. Biol. Chem.* vol. 274(39), Sep. 24, 1999, pp. 27857-27866.

Sanjay Thakur, et al., "Localization of BRCA1 and a Splice Variant Identifies the Nuclear Localization Signal," *Molecular and Cellular Biology*, vol. 17, No. 1, Jan. 1997, pp. 444-452.

Takahiko Horiuchi, et al., "Dominant Expression of a Novel Splice Variant of Caspase-8 in Human Peripheral Blood Lymphocytes," *Biochemical and Biophysical Research Communications 272*, 2000, pp. 877-881.

Chiara Collesi, et al., "A Splicing Variant of the RON Transcript Induces Constitutive Tyrosine Kinase Activity and an Invasive Phenotype," *Molecular and Cellular Biology*, vol. 16, No. 10, Oct. 1996, pp. 5518-5526.

Etienne Leygue, et al., "Expression of the Steroid Receptor RNA Activator in Human Breast Tumors," *Cancer Research* 59, Sep. 1999, pp. 4190-4193.

James G. Jackson, et al., "Elevated Levels of p66 Sch Are Found in Breast Cancer Cell Lines and Primary Tumors with High Metastatic Potential," *Clinical Cancer Research*, vol. 6, Mar. 2000, pp. 1135-1139.

Jun Liu, et al., "Molecular Heterogeneity and Function of EWS-WT1 Fusion Transcripts in Desmoplastic Small Round Cell Tumors," *Clinical Cancer Research*, vol. 6, Sep. 2000, pp. 3522-3529.

Judy M. Coulson, et al., "A Splice Variant of the Neuron-restrictive Silencer Factor Repressor is Expressed in Small Cell Lung Cancer: A Potential Role in Derepression of Neuroendocrine Genes and a Useful Clinical Marker," *Cancer Research* 60, Apr. 1, 2000, pp. 1840-1844.

Ivan Bieche, et al., "Increased Level of Exon 12 Alternatively Spliced BRCA2 Transcripts in Tumor Breast Tissue Compared with Normal Tissue," *Cancer Research* 59, Jun. 1, 1999, pp. 2546-2550.

Mitsunori Fukuda, et al., "Mutation of the Pleckstrin Homology Domain of Bruton's Tyrosine Kinase in Immunodeficiency Impaired Inositol 1,3,4,5-Tetrakisphosphate Binding Capacity," *The Journal of Biological Chemistry*, vol. 271, No. 48, Nov. 29, 1996, pp. 30303-30306.

Bai-Wei Gu, et al., "Variant-type PML-RARα Fusion Transcript in Acute Promyelocytic Leukemia: Use of a Cryptic Coding Sequence from Intron 2 of the RARα Gene and Identification of a New Clinical Subtype Resistant to Retinoic Acid Therapy," *PNAS*, vol. 99, No. 11, May 28, 2002, pp. 7640-7645.

A. M. Mileo, et al., "Two Forms of Acetylcholine Receptor γ Subunit in Mouse Muscle," *Proc. Natl. Acad. Sci. USA*, vol. 92, Mar. 1995, pp. 2686-2690.

Angel Raya, et al., "Goodpasture Antigen-binding Protein, the Kinase That Phosphorylates the Goodpasture Antigen, Is an Alternatively Spliced Variant Implicated in Autoimmune Pathogenesis," *The Journal of Biological Chemistry*, vol. 275, No. 51, Dec. 22, 2000, pp. 40392-40399.

Meena Kumari, "Differential Effects of Chronic Ethanol Treatment on N-Methyl-D-aspartate R1 Splice Variants in Fetal Cortical Neurons," *The Journal of Biological Chemistry*, vol. 276, No. 32, Aug. 10, 2001, pp. 29764-29771.

Gerhard Konig, et al., "Identification and Differential Expression of a Novel Alternative Splice Isoform of the βA4 Amyloid Precursor Protein (APP) mRNA in Leukocytes and Brain Microglial Cells," *The Journal of Biological Chemistry*, vol. 267, No. 15, May 25, 1992, pp. 10804-10809.

Paul Carango, et al., "Overexpression of DM20 Messenger RNA in Two Brothers with Pelizaeus-Merzbacher Disease," *Annals of Neurology*, vol. 38, 1995, pp. 610-617.

Isidore Tepler, et al., "The Gene for the Rat Mast Cell High Affinity IgE Receptor α Chain," *The Journal of Biological Chemistry*, vol. 264, No. 10, Apr. 5, 1989, pp. 5912-5915.

David G. Jackson, et al., "Multiple Variants of the Human Lymphocyte Homing Receptor CD44 Generated by Insertions at a Single Site in the Extracellular Domain," *The Journal of Biological Chemistry*, vol. 267, No. 7, Mar. 5, 1992, pp. 4732-4739.

Krishnendu Roy, et al., "Organization and Alternate Splicing of the Murine Folylpolyglutamate Synthetase Gene," *The Journal of Biological Chemistry*, vol. 271, No. 39, Sep. 27, 1996, pp. 23820-23827.

Chandrashekhar V. Patel, et al., "Endothelial Cells Express a Novel, Tumor Necrosis Factor-α-regulated Variant of HOXA9," *The Journal of Biological Chemistry*, vol. 274, No. 3, Jan. 15, 1999, pp. 1415-1422.

Eric Pasqualini, et al., "Molecular Cloning of the Oncofetal Isoform of the Human Pancreatic Bile Salt-dependent Lipase," *The Journal of Biological Chemistry*, vol. 273, No. 43, Oct. 23, 1998, pp. 28208-28218.

Liselotte E. Jensen, et al., "IRAK1b, a Novel Alternative Splice Variant of Interleukin-1 Receptor-associated Kinase (IRAK, Mediates Interleukin-1 Signaling and Has Prolonged Stability," *The Journal of Biological Chemistry*, vol. 276, No. 31, Aug. 3, 2001, pp. 29037-29044.

Jeehyeon Bae, et al., "MCL-1S, a Splicing Variant of the Antiapoptotic BCL-2 Family Member MCL-1, Encodes a Proapoptotic Protein Possessing Only the BH3 Domain," *The Journal of Biological Chemistry*, vol. 275, No. 33, Aug. 18, 2000, pp. 25255-25261.

Patrick G. Gallagher, et al., "A Splice Site Mutation of the β-Spectrin Gene Causing Exon Skipping in Hereditary Elliptocytosis Associated with a Truncated β-Spectrin Chain," *The Journal of Biological Chemistry*, vol. 266, No. 23, Aug. 15, 1991, pp. 15154-15159.

Huei-Min Lin, et al., "An Isoform of Branched-chain Aminotransferase Is a Novel Co-repressor for Thyroid Hormone Nuclear Receptors," *The Journal of Biological Chemistry*, vol. 276, Issue 51, Dec. 21, 2001, pp. 48196-48205.

Sheau Yu Hsu, et al., "A Splicing Variant of the Bcl-2 Member Bok with a Truncated BH3 Domain Induces Apoptosis but Does Not Dimerize with Antiapoptotic Bcl-2 Proteins in Vitro," *The Journal of Biological Chemistry*, vol. 273, Issue 46, Nov. 13, 1998, pp. 30139-30146.

J. Ross Hawkins, et al., "A 9-Base Pair Deletion in COL1A1 in a Lethal Variant of Osteogenesis Imperfecta," *The Journal of Biological Chemistry*, vol. 266, No. 33, Nov. 25, 1991, pp. 22370-22374.

Mei Zhou, et al., "A Novel Splice Variant of the Cell Death-promoting Protein BAX," *The Journal of Biological Chemistry*, vol. 273, Issue 19, May 8, 1998, pp. 11930-11936.

David K. Moscatello, et al., "Transformation and altered signal transduction by a naturally occurring mutant EGF receptor," *Oncogene 13*, 1996, pp. 85-96.

David K. Moscatello, et al., "Frequent Expression of a Mutant Epidermal Growth Factor Receptor in Multiple Human Tumors," *Cancer Research* 55, Dec. 1, 1995, pp. 5536-5539.

Julie K. Baltz, "Vaccines in the treatment of cancer," *Am. J. Heath-Syst. Pharm.*, vol. 52, Nov. 15, 1995, pp. 2574-2585.

Peter Aichele, et al., "T Cell Priming Versus T. Cell Tolerance Induced by Synthetic Peptides," *J. Exp. Med.*, vol. 182, Jul. 1995, pp. 261-266.

A. Jonas Ekstrand, et al., "Functional characterization of an EGF receptor with a truncated extracellular domain expressed in glioblastomas with EGFR gene amplification," *Oncogene 9*, 1994, pp. 2313-2320.

H. H. Sedlacek, "Vaccination for Treatment of Tumors: A Critical Comment," *Critical Reviews in Ocnogenesis*, 5 (6), 1994, pp. 555-587.

Carol J. Wikstrand, et al., "Investigation of a synthetic peptide as immunogen for a variant epidermal growth factor receptor associated with gliomas," *Journal of Neuroimmunology*, 46, 1993, pp. 165-174.

Albert J. Wong, et al., "Structural alterations of the epidermal growth factor receptor gene in human gliomas," *Proc. Natl. Acad. Sci. USA*, vol. 89, Apr. 1992, pp. 2965-2969.

Richard S. Morrison, "Suppression of Basic Fibroblast Growth Factor Expression by Antisense Oligodeoxynucleotides Inhibits the Growth of Transformed Human Astrocytes," *The Journal of Biological Chemistry*, vol. 266, No. 2, Jan. 15, 1991, pp. 728-734.

Sandra H. Bigner, et al., "Characterization of the Epidermal Growth Receptor in Human Glioma Cell Lines and Xenografts," *Cancer Research 50*, Dec. 15, 1990, pp. 8017-8022.

Hitoshi Yamazaki, et al., "A Deletion Mutation within the Ligand Binding Domain Is Responsible for Activation of Epidermal Growth Factor Receptor Gene in Human Brain Tumors," *Jpn. J. Cancer Res. 81*, Aug. 1990, pp. 773-779.

Y. Sawamura, et al., "Immunotherapy of brain tumors," *Journal of Neurosurgical Sciences*, vol. 34, No. 3-4, Jul.-Dec. 1990, pp. 265-278.

Peter A. Humphrey, et al., "Anti-synthetic peptide antibody reacting at the fusion junction of deletion-mutant epidermal growth factor receptors in human glioblastoma," *Proc. Natl. Acad. Sci. USA*, vol. 87, Jun. 1990, pp. 4207-4211.

C. P. Muller, et al., "Specific antibody response towards predicted epitopes of the epidermal growth factor receptor induced by a thermostable synthetic peptide adjuvant conjugate," *Clin. Exp. Immunol. 78*, 1989, pp. 499-504.

A. L. Harris, "Epidermal Growth Factor Receptor in Human Breast Cancer," *Recent Results in Cancer Research*, 1989, pp. 70-77.

Peter A. Humphrey, et al., "Amplification and Expression of the Epidermal Growth Factor Receptor Gene in Human Glioma Xenografts," *Cancer Research 48*, Apr. 15, 1988, pp. 2231-2238.

Albert J. Wong, et al., "Increased expression of the epidermal growth factor receptor gene in malignant gliomas is invariably associated with gene amplification," *Proc. Natl. Acad. Sci. USA*, vol. 84, Oct. 1987, pp. 6899-6903.

Pier Paolo Di Fiore, et al., Overexpression of the Human EGF Receptor Confers an EGF-Dependent Transformed Phenotype to NIH 3T3 Cells, *Cell*, vol. 51, Dec. 24, 1987, pp. 1063-1070.

Towia A. Libermann, et al., "Amplification, enhanced expression and possible rearrangement of EGF receptor gene in primary human brain tumours of glial origin," *Nature*, vol. 313, Jan. 10, 1985, pp. 144-147.

A. Ullrich, et al., "Human epidermal growth factor receptor cDNA sequence and aberrant expression of the amplified gene in A431 epidermoid carcinoma cells," *Nature*, vol. 309, May 31, 1984, pp. 418-425.

Ingegerd Hellstrom, et al., "Tumor Immunology: An Overview," *Annals New York Academy of Sciences 690*, 1993, pp. 24-33.

Juro Sakai, et al., "Structure Chromosome Location, and Expression of the Human Very Low Density Lipoprotein Receptor Gene," *The Journal of Biological Chemistry*, vol. 269, No. 3, Jan. 21, 1994, pp. 2173-2182.

Takahiko Horiuchi, et al., "Dominant Expression of a Novel Splice Variant of Caspase-8 in Human Peripheral Blood Lymphocytes," *Biochemical and Biophysical Research Communications*, vol. 272, No. 3, Jun. 16, 2000, pp. 877-881 (Abstract only).

G. H. Xiao, et al., "Identification of tuberous sclerosis 2 messenger RNA splice variants that are conserved and differentially expressed in rat and human tissues," *Cell Growth & Differentiation*, vol. 6, Issue 9, 1995, pp. 1185-1191 (Abstract only).

K. Lochner, et al., "A specific deletion in the breakpoint cluster region of the ALL-1 gene is associated with acute lymphoblastic T-cell leukemias," *Cancer Research*, vol. 56, Issue 9, 1996, pp. 2171-2177 (Abstract only).

G. L. Maxwell, et al., "Mutation of the PTEN tumor suppressor gene in endometrial hyperplasias," *Cancer Research*, vol. 58, Issue 12, 1998, pp. 2500-2503 (Abstract only).

R. Misao, et al., "Expression of sex hormone-binding globulin exon VII splicing variant messenger RNA in human uterine endometrial cancers," *Cancer Research*, vol. 57, Issue 24, 1997, pp. 5579-5583 (Abstract only).

S. Mosselman, et al., "Developmentally regulated expression of two novel platelet-derived growth factor alpha-receptor transcripts in human teratocarcinoma cells," *Cancer Research*, vol. 54, Issue 1, 1994, pp. 220-225 (Abstract only).

K.S. Yao, et al., "Alternative splicing and differential expression of DT-diaphorase transcripts in human colon tumors and in peripheral mononuclear cells in response to mitomycin C treatment," *Cancer Research*, vol. 56, Issue 8, 1996, pp. 1731-1736 (Abstract only).

I. Panagopoulos, et al., "The FHIT and PTPRG genes are deleted in benign proliferative breast disease associated with familial breast cancer and cytogenetic rearrangements of chromosome band 3p14," *Cancer Research*, vol. 56, Issue 21, 1996, pp. 4871-4875 (Abstract only).

K. M. Fong, et al., "FHIT and FRA3B 3p14.2 allele loss are common in lung cancer and preneoplastic bronchial lesions and are associated with cancer-related FHIT cDNA splicing aberrations," *Cancer Research*, vol. 57, Issue 11, 1997, pp. 2256-2267 (Abstract only).

E. Leygue, et al., "Prevalence of estrogen receptor variant messenger RNAs in human breast cancer," *Cancer Research*, vol. 56, Issue 19, 1996, pp. 4324-4327 (Abstract only).

C. G. Castles, et al., "Expression of a constitutively active estrogen receptor variant in the estrogen receptor-negative BT-20 human breast cancer cell line," *Cancer Research*, vol. 53, Issue 24, 1993, pp. 5934-5939 (Abstract only).

G. Carruba, et al., "Estradiol inhibits growth of hormone-nonresponsive PC3 human prostate cancer cells," *Cancer Research*, vol. 54, Issue 5, 1994, pp. 1190-1193 (Abstract only).

P. Dall, et al., "Surface protein expression and messenger RNA-splicing analysis of CdD44 in uterine cervical cancer and normal cervical epithelium," *Cancer Research*, vol. 54, Issue 13, 1994, pp. 3337-3341 (Abstract only).

S. Seiter, et al., "Expression of CD44 variant isoforms in malignant melanoma," *Clinical Cancer Research*, vol. 2, Issue 3, 1996, pp. 447-456 (Abstract only).

S. M. Woerner, et al., "Expression of CD44 splice variants in normal, dysplastic, and neoplastic cervical epithelium," *Clinical Cancer Research*, vol. 1, Issue 10, 1995, pp. 1125-1132 (Abstract.

K. Yoshida, et al., Abnormal retention of intron 9 in CD44 gene transcripts in human gastrointestinal tumors, *Cancer Research*, vol. 55, Issue 19, 1995, pp. 4273-4277 (Abstract only).

G. Ermak, et al., "Restricted patterns of CD44 variant exon expression in human papillary thyroid carcinoma," *Cancer Research*, vol. 56, Issue 5, 1996, pp. 1037-1042 (Abstract only).

H-T Zhang et al., "The amino acid isoform of vascular endothelial growth factor is more strongly tumorigenic than other splice variants in vivo", *British Journal of Cancer* (2000) 83(1), 63-68.

Francesca Di Modugno, et al. "MHC-Peptide Binding: Dimers of Cysteine-Containing Nonapeptides Bind With High Affinity to HLA-A2.1 Class I Molecules", *Journal of Immunotherapy*, 20(6); 431-436 (1997).

Burchardt et al., "Expression of messenger ribonucleic acid splice variants for vascular endothelial growth factor in the penis of adult rats and humans," *Biol. Reprod.* 60: 398-404 (1999), Soc'y for the Study of Reproduction, Madison WI.

Houck et al., "The vascular endothelial growth factor family: Identification of a fourth molecular species and characterization of alternative splicing of mRNA," *Mol. Endocrin.* 5: 1806-14 (1991), Endocrine Soc'y, Chevy Chase, MD.

Ferrara et al., "The vascular endothelial growth factor family of polypeptides," *J. Cell. Biochem.* 47: 211-18 (1991), Wiley-Liss, Inc., New York, NY.

Gollmer et al.,"Expression of vascular endothelial growth factor-b in human astrocytoma," *Neuro-Oncology* 2: 80-86 (Apr. 2000), Duke University Press, Durham, NC.

Yamana et al., "Specific immunotherapy with cancer vaccines," *Jpn. 1 Cancer Chemother.* 27(10): 1477-88 (2000) (Japanese language with abstract in English).

Harty et al., "CD8[+] T cells specific for a single nonomer epitope of *Listeria monocytogenes* are protective in vivo," *J. Exp. Med.* 175: 1531-38 (1992), The Rockefeller University Press, New York, NY.

\* cited by examiner

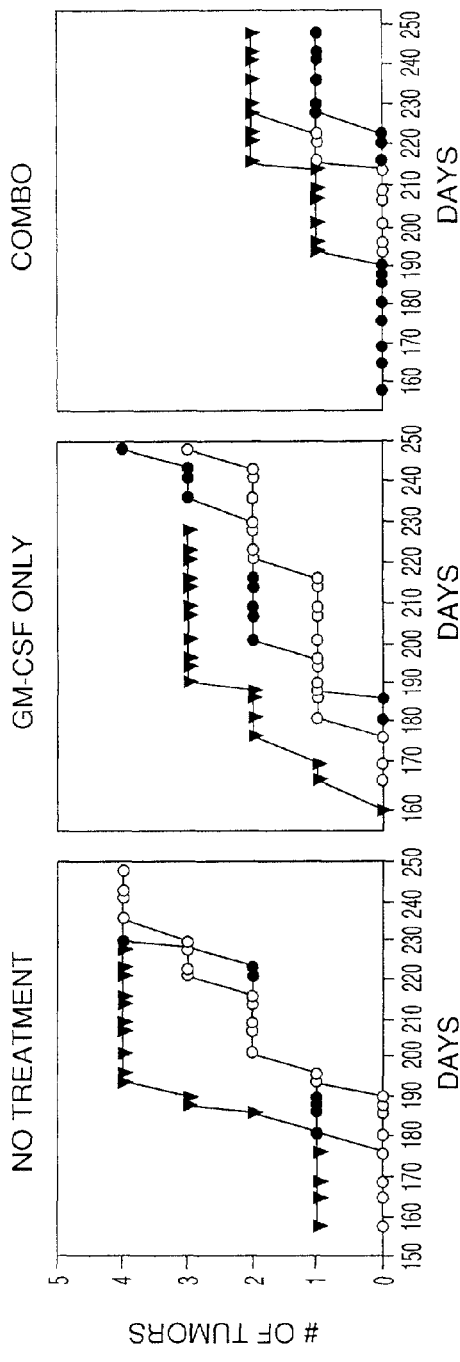
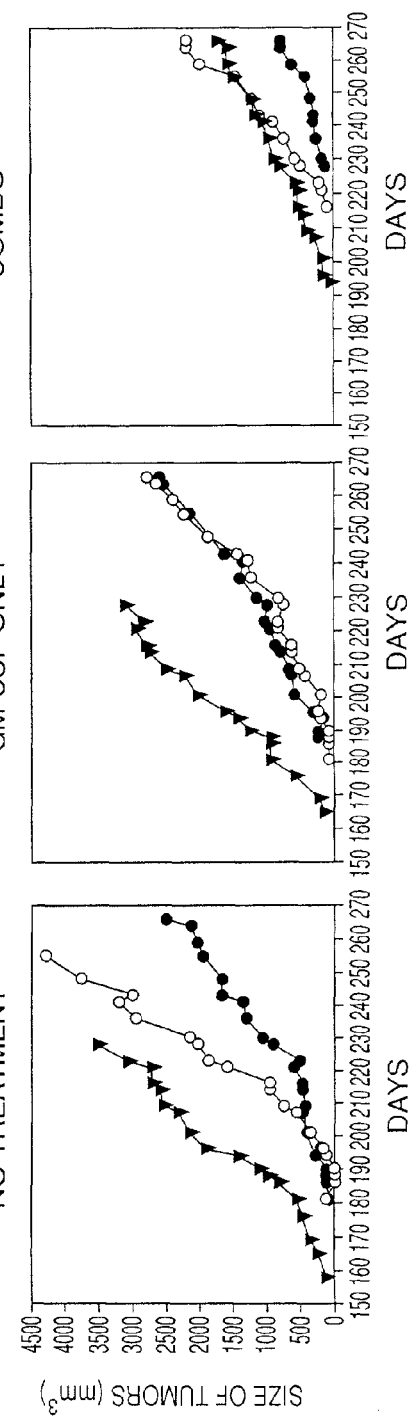
FIG. 3A
FIG. 3B

```
                              SEQUENCE LISTING

<160> NUMBER OF SEQ ID NOS: 82

<210> SEQ ID NO 1
<211> LENGTH: 271
<212> TYPE: PRT
<213> ORGANISM: Homo Sapiens

<400> SEQUENCE: 1

Met Phe Gly Leu Lys Arg Asn Ala Val Ile Gly Leu Asn Leu Tyr Cys
 1               5                  10                  15

Gly Gly Ala Gly Leu Gly Ala Gly Ser Gly Ala Thr Arg Pro Gly
            20                  25                  30

Gly Arg Leu Leu Ala Thr Glu Lys Glu Ala Ser Ala Arg Arg Glu Ile
            35                  40                  45

Gly Gly Gly Glu Ala Gly Ala Val Ile Gly Ser Ala Gly Ala Ser
        50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
                100                 105                 110

Ala Pro Ala Ala Asp Ala Ile Met Ser Pro Glu Glu Leu Asp Gly
            115                 120                 125

Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160

Pro Ser Thr Pro Pro Pro Ala Glu Glu Glu Glu Asp Glu Leu Tyr Arg
                165                 170                 175

Gln Ser Leu Glu Ile Ile Ser Arg Tyr Leu Arg Glu Gln Ala Thr Gly
                180                 185                 190

Ala Lys Asp Thr Lys Pro Met Gly Arg Ser Gly Ala Thr Ser Arg Lys
            195                 200                 205

Ala Leu Glu Thr Leu Arg Arg Val Gly Asp Gly Val Gln Arg Asn His
    210                 215                 220

Glu Thr Ala Phe Gln Gly Trp Val Cys Gly Val Leu Pro Cys Arg Gly
225                 230                 235                 240

Pro Arg Arg Trp His Gln Glu Cys Ala Ala Gly Phe Cys Arg Cys Cys
                245                 250                 255

Trp Ser Arg Ser Trp Phe Gly Ile Ser Asn Lys Ile Ala Leu Leu
                260                 265                 270

<210> SEQ ID NO 2
<211> LENGTH: 18
<212> TYPE: PRT
<213> ORGANISM: Homo sapiens

<400> SEQUENCE: 2

Arg Asn His Glu Thr Ala Phe Gln Gly Trp Val Cys Gly Val Leu Pro
 1               5                  10                  15

Cys Arg
```

<210> SEQ ID NO 3
<211> LENGTH: 61
<212> TYPE: PRT
<213> ORGANISM: Homo Sapiens

<400> SEQUENCE: 3

Asn Ser Asn His Val Ala Ser Gly Ala Pro Val Cys His Asn Pro Asn
1               5                   10                  15

Leu Pro Ser Trp Gln Gly Ala Leu Gly Pro Tyr Val Val Val Leu
            20                  25                  30

Ala Pro Asp Thr Trp Leu Ser Ser Leu Arg Leu Ser Ser Pro Gly
        35                  40                  45

Val Glu Gly Arg Ser Cys Ser Ala Arg Glu Thr Gln Ala
    50                  55                  60

<210> SEQ ID NO 4
<211> LENGTH: 682
<212> TYPE: PRT
<213> ORGANISM: Homo Sapiens

<400> SEQUENCE: 4

Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Pro Ala Pro Leu Pro Ser Pro Gly
            100                 105                 110

Thr Thr Ala Pro Arg Pro Ser Ser Ile Pro Ala Pro Ala Glu Ala Glu
        115                 120                 125

Ala Trp Ser Pro Arg Lys Leu Pro Ser Ser Ala Ser Thr Phe Leu Ser
    130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
        195                 200                 205

Thr His Asn Phe Ser Glu Glu Leu Lys Ile Gly Glu Gly Gly Phe Gly
    210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

```
Asp Phe Ala Gly Tyr Cys Ala Gln Asn Gly Phe Tyr Cys Leu Val Tyr
            275                 280                 285

Gly Phe Leu Pro Asn Gly Ser Leu Glu Asp Arg Leu His Cys Gln Thr
290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
                325                 330                 335

Ile His Gly Asp Ile Lys Ser Ser Asn Val Leu Leu Asp Glu Arg Leu
                340                 345                 350

Thr Pro Lys Leu Gly Asp Phe Gly Leu Ala Arg Phe Ser Arg Phe Ala
                355                 360                 365

Gly Ser Ser Pro Ser Gln Ser Ser Met Val Ala Arg Thr Gln Thr Val
370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Val Leu Glu
                405                 410                 415

Thr Leu Ala Gly Gln Arg Ala Val Lys Thr His Gly Ala Arg Thr Lys
                420                 425                 430

Tyr Leu Lys Asp Leu Val Glu Glu Ala Glu Ala Gly Val Ala
                435                 440                 445

Leu Arg Ser Thr Gln Ser Thr Leu Gln Ala Gly Leu Ala Ala Asp Ala
450                 455                 460

Trp Ala Ala Pro Ile Ala Met Gln Ile Tyr Lys Lys His Leu Asp Pro
465                 470                 475                 480

Arg Pro Gly Pro Cys Pro Pro Glu Leu Gly Leu Gly Leu Gln Leu
                485                 490                 495

Ala Cys Cys Cys Leu His Arg Arg Ala Lys Arg Arg Pro Pro Met Thr
                500                 505                 510

Gln Glu Asn Ser Tyr Val Ser Ser Thr Gly Arg Ala His Ser Gly Ala
                515                 520                 525

Ala Pro Trp Gln Pro Leu Ala Ala Pro Ser Gly Ala Ser Ala Gln Ala
                530                 535                 540

Ala Glu Gln Leu Gln Arg Gly Pro Asn Gln Pro Val Glu Ser Asp Glu
545                 550                 555                 560

Ser Leu Gly Gly Leu Ser Ala Ala Leu Arg Ser Trp His Leu Thr Pro
                565                 570                 575

Ser Cys Pro Leu Asp Pro Ala Pro Leu Arg Glu Ala Gly Cys Pro Gln
                580                 585                 590

Gly Asp Thr Ala Gly Glu Ser Ser Trp Gly Ser Gly Pro Gly Ser Arg
                595                 600                 605

Pro Thr Ala Val Glu Gly Leu Ala Leu Gly Ser Ser Ala Ser Ser Ser
610                 615                 620

Ser Glu Pro Pro Gln Ile Ile Ile Asn Pro Ala Arg Gln Lys Met Val
625                 630                 635                 640

Gln Lys Leu Ala Leu Tyr Glu Asp Gly Ala Leu Asp Ser Leu Gln Leu
                645                 650                 655

Leu Ser Ser Ser Ser Leu Pro Gly Leu Gly Leu Glu Gln Asp Arg Gln
                660                 665                 670

Gly Pro Glu Glu Ser Asp Glu Phe Gln Ser
                675                 680

<210> SEQ ID NO 5
```

```
<211> LENGTH: 30
<212> TYPE: PRT
<213> ORGANISM: Homo sapiens

<400> SEQUENCE: 5

Val Tyr Glu Arg Leu Glu Lys Leu Gln Ala Val Val Ala Gly Val Pro
 1               5                  10                  15

Gly His Ser Glu Ala Ala Ser Cys Ile Pro Pro Ser Pro Gln
            20                  25                  30

<210> SEQ ID NO 6
<211> LENGTH: 380
<212> TYPE: PRT
<213> ORGANISM: Homo Sapiens

<400> SEQUENCE: 6

Met Ala Ala Ala Leu Gly Gln Ile Trp Ala Arg Lys Leu Leu Ser
 1               5                  10                  15

Val Pro Trp Leu Leu Cys Gly Pro Arg Arg Tyr Ala Ser Ser Phe
            20                  25                  30

Lys Ala Ala Asp Leu Gln Leu Glu Met Thr Gln Lys Pro His Lys Lys
                35                  40                  45

Pro Gly Pro Gly Glu Pro Leu Val Phe Gly Lys Thr Phe Thr Asp His
 50                  55                  60

Met Leu Met Val Glu Trp Asn Asp Lys Gly Trp Gly Gln Pro Arg Ile
 65                  70                  75                  80

Gln Pro Phe Gln Asn Leu Thr Leu His Pro Ala Ser Ser Ser Leu His
                85                  90                  95

Tyr Ser Leu Gln Leu Phe Glu Gly Met Lys Ala Phe Lys Gly Lys Asp
            100                 105                 110

Gln Gln Val Arg Leu Phe Arg Pro Trp Leu Asn Met Asp Arg Met Leu
        115                 120                 125

Arg Ser Ala Met Arg Leu Cys Leu Pro Ser Phe Asp Lys Leu Glu Leu
    130                 135                 140

Leu Glu Cys Ile Arg Arg Leu Ile Glu Val Asp Lys Asp Trp Val Pro
145                 150                 155                 160

Asp Ala Ala Gly Thr Ser Leu Tyr Val Arg Pro Val Leu Ile Gly Asn
                165                 170                 175

Glu Pro Ser Leu Gly Val Ser Gln Pro Arg Arg Ala Leu Leu Phe Val
            180                 185                 190

Ile Leu Cys Pro Val Gly Ala Tyr Phe Pro Gly Gly Ser Val Thr Pro
        195                 200                 205

Val Ser Leu Leu Ala Asp Pro Ala Phe Ile Arg Ala Trp Val Gly Gly
    210                 215                 220

Val Gly Asn Tyr Lys Leu Gly Gly Asn Tyr Gly Pro Thr Val Leu Val
225                 230                 235                 240

Gln Gln Glu Ala Leu Lys Arg Gly Cys Glu Gln Val Leu Trp Leu Tyr
                245                 250                 255

Gly Pro Asp His Gln Leu Thr Glu Val Gly Thr Met Asn Ile Phe Val
            260                 265                 270

Tyr Trp Thr His Glu Asp Gly Val Leu Glu Leu Val Thr Pro Pro Leu
        275                 280                 285

Asn Gly Val Ile Leu Pro Gly Val Arg Gln Ser Leu Leu Asp Met
    290                 295                 300

Ala Gln Thr Trp Gly Glu Phe Arg Val Val Glu Arg Thr Ile Thr Met
305                 310                 315                 320
```

```
Lys Gln Leu Leu Arg Ala Leu Glu Glu Gly Arg Val Arg Glu Val Phe
                325                 330                 335
Gly Ser Gly Thr Ala Cys Gln Asn Leu His Ile Pro Thr Met Glu Asn
            340                 345                 350
Gly Pro Glu Leu Ile Leu Arg Phe Gln Lys Glu Leu Lys Glu Ile Gln
        355                 360                 365
Tyr Gly Ile Arg Ala His Glu Trp Met Phe Pro Val
    370                 375                 380

<210> SEQ ID NO 7
<211> LENGTH: 612
<212> TYPE: PRT
<213> ORGANISM: Homo Sapiens

<400> SEQUENCE: 7

Ala Lys Leu Gly Ala Val Tyr Thr Glu Gly Phe Val Glu Gly Val
 1               5                  10                  15
Asn Lys Lys Leu Gly Leu Leu Gly Asp Ser Val Asp Ile Phe Lys Gly
            20                  25                  30
Ile Pro Phe Ala Ala Pro Thr Lys Ala Leu Glu Asn Pro Gln Pro His
        35                  40                  45
Pro Gly Trp Gln Gly Thr Leu Lys Ala Lys Asn Phe Lys Lys Arg Cys
    50                  55                  60
Leu Gln Ala Thr Ile Thr Gln Asp Ser Thr Tyr Gly Asp Glu Asp Cys
65                  70                  75                  80
Leu Tyr Leu Asn Ile Trp Val Pro Gln Gly Arg Lys Gln Val Ser Arg
                85                  90                  95
Asp Leu Pro Val Met Ile Trp Ile Tyr Gly Gly Ala Phe Leu Met Gly
            100                 105                 110
Ser Gly His Gly Ala Asn Phe Leu Asn Asn Tyr Leu Tyr Asp Gly Glu
        115                 120                 125
Glu Ile Ala Thr Arg Gly Asn Val Ile Val Val Thr Phe Asn Tyr Arg
    130                 135                 140
Val Gly Pro Leu Gly Phe Leu Ser Thr Gly Asp Ala Asn Leu Pro Gly
145                 150                 155                 160
Asn Tyr Gly Leu Arg Asp Gln His Met Ala Ile Ala Trp Val Lys Arg
                165                 170                 175
Asn Ile Ala Ala Phe Gly Gly Asp Pro Asn Asn Ile Thr Leu Phe Gly
            180                 185                 190
Glu Ser Ala Gly Gly Ala Ser Val Ser Leu Gln Thr Leu Ser Pro Tyr
        195                 200                 205
Asn Lys Gly Leu Ile Arg Arg Ala Ile Ser Gln Ser Gly Val Ala Leu
    210                 215                 220
Ser Pro Trp Val Ile Gln Lys Asn Pro Leu Phe Trp Ala Lys Lys Val
225                 230                 235                 240
Ala Glu Lys Val Gly Cys Pro Val Gly Asp Ala Ala Arg Met Ala Gln
                245                 250                 255
Cys Leu Lys Val Thr Asp Pro Arg Ala Leu Thr Leu Ala Tyr Lys Val
            260                 265                 270
Pro Leu Ala Gly Leu Glu Tyr Pro Met Leu His Tyr Val Gly Phe Val
        275                 280                 285
Pro Val Ile Asp Gly Asp Phe Ile Pro Ala Asp Pro Ile Asn Leu Tyr
    290                 295                 300
Ala Asn Ala Ala Asp Ile Asp Tyr Ile Ala Gly Thr Asn Asn Met Asp
305                 310                 315                 320
```

-continued

```
Gly His Ile Phe Ala Ser Ile Asp Met Pro Ala Ile Asn Lys Gly Asn
                325                 330                 335

Lys Lys Val Thr Glu Glu Asp Phe Tyr Lys Leu Val Ser Glu Phe Thr
            340                 345                 350

Ile Thr Lys Gly Leu Arg Gly Ala Lys Thr Thr Phe Asp Val Tyr Thr
        355                 360                 365

Glu Ser Trp Ala Gln Asp Pro Ser Gln Glu Asn Lys Lys Lys Thr Val
    370                 375                 380

Val Asp Phe Glu Thr Asp Val Leu Phe Leu Val Pro Thr Glu Ile Ala
385                 390                 395                 400

Leu Ala Gln His Arg Ala Asn Ala Lys Ser Ala Lys Thr Tyr Ala Tyr
                405                 410                 415

Leu Phe Ser His Pro Ser Arg Met Pro Val Tyr Pro Lys Trp Val Gly
            420                 425                 430

Ala Asp His Ala Asp Asp Ile Gln Tyr Val Phe Gly Lys Pro Phe Ala
        435                 440                 445

Thr Pro Thr Gly Tyr Arg Pro Gln Asp Arg Thr Val Ser Lys Ala Met
    450                 455                 460

Ile Ala Tyr Trp Thr Asn Phe Ala Lys Thr Gly Asp Pro Asn Met Gly
465                 470                 475                 480

Asp Ser Ala Val Pro Thr His Trp Glu Pro Tyr Thr Thr Glu Asn Ser
                485                 490                 495

Gly Tyr Leu Glu Ile Thr Lys Lys Met Gly Ser Ser Ser Met Lys Arg
            500                 505                 510

Ser Leu Arg Thr Asn Phe Leu Arg Tyr Trp Thr Leu Thr Tyr Leu Ala
        515                 520                 525

Leu Pro Thr Val Thr Asp Gln Glu Ala Thr Pro Val Pro Pro Thr Gly
    530                 535                 540

Asp Ser Glu Ala Thr Pro Val Pro Pro Thr Gly Asp Ser Glu Thr Ala
545                 550                 555                 560

Pro Val Pro Pro Thr Gly Asp Ser Gly Ala Pro Pro Val Pro Pro Thr
                565                 570                 575

Gly Asp Ser Gly Ala Pro Pro Val Pro Pro Thr Gly Asp Ser Glu Ala
            580                 585                 590

Ala Pro Val Pro Pro Thr Gly Asp Ser Lys Glu Ala Gln Met Pro Ala
        595                 600                 605

Val Ile Arg Phe
        610

<210> SEQ ID NO 8
<211> LENGTH: 16
<212> TYPE: PRT
<213> ORGANISM: Homo sapiens

<400> SEQUENCE: 8

Ala Pro Val Pro Pro Thr Gly Asp Ser Gly Ala Pro Val Pro Pro
 1               5                  10                  15

<210> SEQ ID NO 9
<211> LENGTH: 271
<212> TYPE: PRT
<213> ORGANISM: Homo Sapiens

<400> SEQUENCE: 9

Met Ala Thr Thr Gly Ala Leu Gly Asn Tyr Tyr Val Asp Ser Phe Leu
 1               5                  10                  15

Leu Gly Ala Asp Ala Ala Asp Glu Leu Ser Val Gly Arg Tyr Ala Pro
```

```
                    20                  25                  30
Gly Thr Leu Gly Gln Pro Pro Arg Gln Ala Ala Thr Leu Ala Glu His
                35                  40                  45

Pro Asp Phe Ser Pro Cys Ser Phe Gln Ser Lys Ala Thr Val Phe Val
            50                  55                  60

Ala Ser Trp Asn Pro Val His Ala Ala Gly Ala Asn Ala Val Pro Ala
65                  70                  75                  80

Val Tyr His His His His His His Pro Tyr Val His Pro Gln Ala Pro
                    85                  90                  95

Val Ala Ala Ala Pro Asp Gly Arg Tyr Met Arg Ser Trp Leu Glu
            100                 105                 110

Pro Thr Pro Gly Ala Leu Ser Phe Ala Gly Leu Pro Ser Ser Arg Pro
                115                 120                 125

Tyr Gly Ile Lys Pro Glu Pro Leu Ser Ala Arg Arg Gly Asp Cys Pro
            130                 135                 140

Thr Leu Asp Thr His Thr Leu Ser Leu Thr Asp Tyr Ala Cys Gly Ser
145                 150                 155                 160

Pro Pro Val Asp Arg Glu Lys Gln Pro Ser Glu Gly Ala Phe Ser Glu
                165                 170                 175

Asn Asn Ala Glu Asn Glu Ser Gly Gly Asp Lys Pro Ile Asp Pro
            180                 185                 190

Asn Asn Pro Ala Ala Asn Trp Leu His Ala Arg Ser Thr Arg Lys Lys
                195                 200                 205

Arg Cys Pro Tyr Thr Lys His Gln Thr Leu Glu Leu Glu Lys Glu Phe
            210                 215                 220

Leu Phe Asn Met Tyr Leu Thr Arg Asp Arg Arg Tyr Glu Val Ala Arg
225                 230                 235                 240

Leu Phe Asn Leu Thr Glu Arg Gln Val Lys Ile Trp Phe Gln Asn Arg
                245                 250                 255

Arg Met Lys Met Lys Lys Ile Asn Lys Asp Arg Ala Lys Asp Glu
            260                 265                 270

<210> SEQ ID NO 10
<211> LENGTH: 14
<212> TYPE: PRT
<213> ORGANISM: Homo sapiens

<400> SEQUENCE: 10

Asp Lys Pro Pro Ile Asp Pro Asn Asn Pro Ala Ala Asn Trp
1               5                   10

<210> SEQ ID NO 11
<211> LENGTH: 587
<212> TYPE: PRT
<213> ORGANISM: Mus musculus

<400> SEQUENCE: 11

Met Ser Trp Ala Arg Ser Arg Leu Cys Ser Thr Leu Ser Leu Ala Ala
1               5                   10                  15

Val Ser Ala Arg Gly Ala Thr Thr Glu Gly Pro Ala Arg Gly Met
            20                  25                  30

Ser Ala Gly Pro Ala Pro Gln Glu Pro Gly Met Glu Tyr Gln Asp Ala
        35                  40                  45

Val Arg Thr Leu Asn Thr Leu Gln Thr Asn Ala Ser Tyr Leu Glu Gln
    50                  55                  60

Val Lys Arg Gln Arg Ser Asp Pro Gln Ala Gln Leu Glu Ala Met Glu
65                  70                  75                  80
```

```
Met Tyr Leu Ala Arg Ser Gly Leu Gln Val Glu Asp Leu Asn Arg Leu
                85                  90                  95
Asn Ile Ile His Val Thr Gly Thr Lys Gly Lys Gly Ser Thr Cys Ala
            100                 105                 110
Phe Thr Glu Arg Ile Leu Arg Asn Tyr Gly Leu Lys Thr Gly Phe Phe
            115                 120                 125
Arg Ser Pro His Met Val Gln Val Arg Asp Arg Ile Arg Ile Asn Gly
        130                 135                 140
Lys Pro Ile Ser Pro Glu Leu Phe Thr Lys His Phe Trp Cys Leu Tyr
145                 150                 155                 160
Asn Gln Leu Glu Glu Phe Lys Asp Asp Ser His Val Ser Met Pro Ser
                165                 170                 175
Tyr Phe Arg Phe Leu Thr Leu Met Ala Phe His Val Phe Leu Gln Glu
            180                 185                 190
Lys Val Asp Leu Ala Val Val Glu Val Gly Ile Gly Gly Ala Phe Asp
        195                 200                 205
Cys Thr Asn Ile Ile Arg Lys Pro Val Val Cys Gly Val Ser Ser Leu
    210                 215                 220
Gly Ile Asp His Thr Ser Leu Leu Gly Asp Thr Val Glu Lys Ile Ala
225                 230                 235                 240
Trp Gln Lys Gly Gly Ile Phe Lys Pro Gly Val Pro Ala Phe Thr Val
                245                 250                 255
Val Gln Pro Glu Gly Pro Leu Ala Val Leu Arg Asp Arg Ala Gln Gln
            260                 265                 270
Ile Gly Cys Pro Leu Tyr Leu Cys Pro Pro Leu Glu Ala Leu Glu Glu
        275                 280                 285
Val Gly Leu Pro Leu Ser Leu Gly Leu Glu Gly Ala His Gln Arg Ser
    290                 295                 300
Asn Ala Ala Leu Ala Leu Gln Leu Ala His Cys Trp Leu Glu Arg Gln
305                 310                 315                 320
Asp His Gln Asp Ile Gln Glu Leu Lys Val Ser Arg Pro Ser Ile Arg
                325                 330                 335
Trp Gln Leu Pro Leu Ala Pro Val Phe Arg Pro Thr Pro His Met Arg
            340                 345                 350
Arg Gly Leu Arg Asp Thr Val Trp Pro Gly Arg Thr Gln Ile Leu Gln
        355                 360                 365
Arg Gly Pro Leu Thr Trp Tyr Leu Asp Gly Ala His Thr Thr Ser Ser
    370                 375                 380
Val Gln Ala Cys Val His Trp Tyr Arg Gln Ser Leu Glu Arg Ser Lys
385                 390                 395                 400
Arg Thr Asp Gly Gly Ser Glu Val His Ile Leu Leu Phe Asn Ser Thr
                405                 410                 415
Gly Asp Arg Asp Ser Ala Ala Leu Leu Lys Leu Leu Gln Pro Cys Gln
            420                 425                 430
Phe Asp Tyr Ala Val Phe Cys Pro Asn Val Thr Glu Val Ser Ser Ile
        435                 440                 445
Gly Asn Ala Asp Gln Gln Asn Phe Thr Val Thr Leu Asp Gln Val Leu
    450                 455                 460
Leu Arg Cys Leu Gln His Gln Gln His Trp Asn Gly Leu Ala Glu Lys
465                 470                 475                 480
Gln Ala Ser Ser Asn Leu Trp Ser Ser Cys Gly Pro Asp Pro Ala Gly
                485                 490                 495
Pro Gly Ser Leu Leu Leu Ala Pro His Pro Pro Gln Pro Thr Arg Thr
```

```
                    500                 505                 510
Ser Ser Leu Val Phe Ser Cys Ile Ser His Ala Leu Leu Trp Ile Ser
            515                 520                 525

Gln Gly Arg Asp Pro Ile Phe Gln Pro Gln Ser Leu Pro Arg Asn Leu
        530                 535                 540

Leu Asn His Pro Thr Ala Asn Ser Gly Ala Ser Ile Leu Arg Glu Ala
545                 550                 555                 560

Ala Ala Ile His Val Leu Val Thr Gly Ser Leu His Leu Val Gly Gly
                565                 570                 575

Val Leu Lys Leu Leu Asp Pro Ser Met Ser Gln
            580                 585

<210> SEQ ID NO 12
<211> LENGTH: 18
<212> TYPE: PRT
<213> ORGANISM: Mus musculus

<400> SEQUENCE: 12

Ala Val Ser Ala Arg Gly Ala Thr Thr Glu Gly Pro Ala Arg Arg Gly
1               5                   10                  15

Met Ser

<210> SEQ ID NO 13
<211> LENGTH: 237
<212> TYPE: DNA
<213> ORGANISM: Homo Sapiens
<220> FEATURE:
<221> NAME/KEY: CDS
<222> LOCATION: (1)...(237)

<400> SEQUENCE: 13 gac aga atc cct gct acc aat agg aat gat gtc aca ggt gga aga aga      48
Asp Arg Ile Pro Ala Thr Asn Arg Asn Asp Val Thr Gly Gly Arg Arg
1               5                   10                  15 gac cca aat cat tct gaa ggc tca act act tta ctg gaa ggt tat acc      96
Asp Pro Asn His Ser Glu Gly Ser Thr Thr Leu Leu Glu Gly Tyr Thr
                20                  25                  30 tct cat tac cca cac acg aag gaa agc agg acc ttc atc cca gtg acc     144
Ser His Tyr Pro His Thr Lys Glu Ser Arg Thr Phe Ile Pro Val Thr
            35                  40                  45 tca gct aag act ggg tcc ttt gga gtt act gca gtt act gtt gga gat     192
Ser Ala Lys Thr Gly Ser Phe Gly Val Thr Ala Val Thr Val Gly Asp
        50                  55                  60 tcc aac tct aat gtc aat cgt tcc tta tca gga gac caa gac aca         237
Ser Asn Ser Asn Val Asn Arg Ser Leu Ser Gly Asp Gln Asp Thr
65                  70                  75

<210> SEQ ID NO 14
<211> LENGTH: 79
<212> TYPE: PRT
<213> ORGANISM: Homo Sapiens

<400> SEQUENCE: 14

Asp Arg Ile Pro Ala Thr Asn Arg Asn Asp Val Thr Gly Gly Arg Arg
1               5                   10                  15

Asp Pro Asn His Ser Glu Gly Ser Thr Thr Leu Leu Glu Gly Tyr Thr
                20                  25                  30

Ser His Tyr Pro His Thr Lys Glu Ser Arg Thr Phe Ile Pro Val Thr
            35                  40                  45

Ser Ala Lys Thr Gly Ser Phe Gly Val Thr Ala Val Thr Val Gly Asp
        50                  55                  60
```

```
Ser Asn Ser Asn Val Asn Arg Ser Leu Ser Gly Asp Gln Asp Thr
 65                  70                  75

<210> SEQ ID NO 15
<211> LENGTH: 327
<212> TYPE: DNA
<213> ORGANISM: Homo Sapiens
<220> FEATURE:
<221> NAME/KEY: CDS
<222> LOCATION: (1)...(327)

<400> SEQUENCE: 15 gac aga atc cct gct acc aag cag agt aat tct cag agc ttc tct aca      48
Asp Arg Ile Pro Ala Thr Lys Gln Ser Asn Ser Gln Ser Phe Ser Thr
 1               5                  10                  15 tca cat gaa ggc ttg gaa gaa gat aaa gac cat cca aca act tct act      96
Ser His Glu Gly Leu Glu Glu Asp Lys Asp His Pro Thr Thr Ser Thr
             20                  25                  30 ctg aca tca agc aat agg aat gat gtc aca ggt gga aga aga gac cca     144
Leu Thr Ser Ser Asn Arg Asn Asp Val Thr Gly Gly Arg Arg Asp Pro
         35                  40                  45 aat cat tct gaa ggc tca act act tta ctg gaa ggt tat acc tct cat     192
Asn His Ser Glu Gly Ser Thr Thr Leu Leu Glu Gly Tyr Thr Ser His
     50                  55                  60 tac cca cac acg aag gaa agc agg acc ttc atc cca gtg acc tca gct     240
Tyr Pro His Thr Lys Glu Ser Arg Thr Phe Ile Pro Val Thr Ser Ala
 65                  70                  75                  80 aag act ggg tcc ttt gga gtt act gca gtt act gtt gga gat tcc aac     288
Lys Thr Gly Ser Phe Gly Val Thr Ala Val Thr Val Gly Asp Ser Asn
                 85                  90                  95 tct aat gtc aat cgt tcc tta tca gga gac caa gac aca                 327
Ser Asn Val Asn Arg Ser Leu Ser Gly Asp Gln Asp Thr
            100                 105

<210> SEQ ID NO 16
<211> LENGTH: 109
<212> TYPE: PRT
<213> ORGANISM: Homo Sapiens

<400> SEQUENCE: 16

Asp Arg Ile Pro Ala Thr Lys Gln Ser Asn Ser Gln Ser Phe Ser Thr
 1               5                  10                  15

Ser His Glu Gly Leu Glu Glu Asp Lys Asp His Pro Thr Thr Ser Thr
             20                  25                  30

Leu Thr Ser Ser Asn Arg Asn Asp Val Thr Gly Gly Arg Arg Asp Pro
         35                  40                  45

Asn His Ser Glu Gly Ser Thr Thr Leu Leu Glu Gly Tyr Thr Ser His
     50                  55                  60

Tyr Pro His Thr Lys Glu Ser Arg Thr Phe Ile Pro Val Thr Ser Ala
 65                  70                  75                  80

Lys Thr Gly Ser Phe Gly Val Thr Ala Val Thr Val Gly Asp Ser Asn
                 85                  90                  95

Ser Asn Val Asn Arg Ser Leu Ser Gly Asp Gln Asp Thr
            100                 105

<210> SEQ ID NO 17
<211> LENGTH: 429
<212> TYPE: DNA
<213> ORGANISM: Homo Sapiens
<220> FEATURE:
<221> NAME/KEY: CDS
<222> LOCATION: (1)...(429)
```

<400> SEQUENCE: 17

| | | | | | | | | | | | | | | | | |
|---|---|---|---|---|---|---|---|---|---|---|---|---|---|---|---|---|
| gac | aga | atc | cct | gct | acc | aat | atg | gac | tcc | agt | cat | agt | aca | acg | ctt | 48 |
| Asp | Arg | Ile | Pro | Ala | Thr | Asn | Met | Asp | Ser | Ser | His | Ser | Thr | Thr | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cag | cct | act | gca | aat | cca | aac | aca | ggt | ttg | gtg | gaa | gat | ttg | gac | agg | 96 |
| Gln | Pro | Thr | Ala | Asn | Pro | Asn | Thr | Gly | Leu | Val | Glu | Asp | Leu | Asp | Arg | |
| | | | 20 | | | | | 25 | | | | | 30 | | | |

| | | | | | | | | | | | | | | | | |
|---|---|---|---|---|---|---|---|---|---|---|---|---|---|---|---|---|
| aca | gga | cct | ctt | tca | atg | aca | acg | cag | cag | agt | aat | tct | cag | agc | ttc | 144 |
| Thr | Gly | Pro | Leu | Ser | Met | Thr | Thr | Gln | Gln | Ser | Asn | Ser | Gln | Ser | Phe | |
| | | 35 | | | | | 40 | | | | | 45 | | | | |

| | | | | | | | | | | | | | | | | |
|---|---|---|---|---|---|---|---|---|---|---|---|---|---|---|---|---|
| tct | aca | tca | cat | gaa | ggc | ttg | gaa | gaa | gat | aaa | gac | cat | cca | aca | act | 192 |
| Ser | Thr | Ser | His | Glu | Gly | Leu | Glu | Glu | Asp | Lys | Asp | His | Pro | Thr | Thr | |
| | 50 | | | | | 55 | | | | | 60 | | | | | |

| | | | | | | | | | | | | | | | | |
|---|---|---|---|---|---|---|---|---|---|---|---|---|---|---|---|---|
| tct | act | ctg | aca | tca | agc | aat | agg | aat | gat | gtc | aca | ggt | gga | aga | aga | 240 |
| Ser | Thr | Leu | Thr | Ser | Ser | Asn | Arg | Asn | Asp | Val | Thr | Gly | Gly | Arg | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gac | cca | aat | cat | tct | gaa | ggc | tca | act | act | tta | ctg | gaa | ggt | tat | acc | 288 |
| Asp | Pro | Asn | His | Ser | Glu | Gly | Ser | Thr | Thr | Leu | Leu | Glu | Gly | Tyr | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| tct | cat | tac | cca | cac | acg | aag | gaa | agc | agg | acc | ttc | atc | cca | gtg | acc | 336 |
| Ser | His | Tyr | Pro | His | Thr | Lys | Glu | Ser | Arg | Thr | Phe | Ile | Pro | Val | Thr | |
| | | | 100 | | | | | 105 | | | | | 110 | | | |

| | | | | | | | | | | | | | | | | |
|---|---|---|---|---|---|---|---|---|---|---|---|---|---|---|---|---|
| tca | gct | aag | act | ggg | tcc | ttt | gga | gtt | act | gca | gtt | act | gtt | gga | gat | 384 |
| Ser | Ala | Lys | Thr | Gly | Ser | Phe | Gly | Val | Thr | Ala | Val | Thr | Val | Gly | Asp | |
| | | 115 | | | | | 120 | | | | | 125 | | | | |

| | | | | | | | | | | | | | | |
|---|---|---|---|---|---|---|---|---|---|---|---|---|---|---|
| tcc | aac | tct | aat | gtc | aat | cgt | tcc | tta | tca | gga | gac | caa | gac | aca | 429 |
| Ser | Asn | Ser | Asn | Val | Asn | Arg | Ser | Leu | Ser | Gly | Asp | Gln | Asp | Thr | |
| | 130 | | | | | 135 | | | | | 140 | | | | |

<210> SEQ ID NO 18
<211> LENGTH: 143
<212> TYPE: PRT
<213> ORGANISM: Homo Sapiens

<400> SEQUENCE: 18

| | | | | | | | | | | | | | |
|---|---|---|---|---|---|---|---|---|---|---|---|---|---|
| Asp | Arg | Ile | Pro | Ala | Thr | Asn | Met | Asp | Ser | Ser | His | Ser | Thr | Thr | Leu |
| 1 | | | | 5 | | | | | 10 | | | | | 15 | |

| | | | | | | | | | | | | | |
|---|---|---|---|---|---|---|---|---|---|---|---|---|---|
| Gln | Pro | Thr | Ala | Asn | Pro | Asn | Thr | Gly | Leu | Val | Glu | Asp | Leu | Asp | Arg |
| | | | 20 | | | | | 25 | | | | | 30 | | |

| | | | | | | | | | | | | | |
|---|---|---|---|---|---|---|---|---|---|---|---|---|---|
| Thr | Gly | Pro | Leu | Ser | Met | Thr | Thr | Gln | Gln | Ser | Asn | Ser | Gln | Ser | Phe |
| | | 35 | | | | | 40 | | | | | 45 | | | |

| | | | | | | | | | | | | | |
|---|---|---|---|---|---|---|---|---|---|---|---|---|---|
| Ser | Thr | Ser | His | Glu | Gly | Leu | Glu | Glu | Asp | Lys | Asp | His | Pro | Thr | Thr |
| | 50 | | | | | 55 | | | | | 60 | | | | |

| | | | | | | | | | | | | | |
|---|---|---|---|---|---|---|---|---|---|---|---|---|---|
| Ser | Thr | Leu | Thr | Ser | Ser | Asn | Arg | Asn | Asp | Val | Thr | Gly | Gly | Arg | Arg |
| 65 | | | | | 70 | | | | | 75 | | | | | 80 |

| | | | | | | | | | | | | | |
|---|---|---|---|---|---|---|---|---|---|---|---|---|---|
| Asp | Pro | Asn | His | Ser | Glu | Gly | Ser | Thr | Thr | Leu | Leu | Glu | Gly | Tyr | Thr |
| | | | | 85 | | | | | 90 | | | | | 95 | |

| | | | | | | | | | | | | | |
|---|---|---|---|---|---|---|---|---|---|---|---|---|---|
| Ser | His | Tyr | Pro | His | Thr | Lys | Glu | Ser | Arg | Thr | Phe | Ile | Pro | Val | Thr |
| | | | 100 | | | | | 105 | | | | | 110 | | |

| | | | | | | | | | | | | | |
|---|---|---|---|---|---|---|---|---|---|---|---|---|---|
| Ser | Ala | Lys | Thr | Gly | Ser | Phe | Gly | Val | Thr | Ala | Val | Thr | Val | Gly | Asp |
| | | 115 | | | | | 120 | | | | | 125 | | | |

| | | | | | | | | | | | | | |
|---|---|---|---|---|---|---|---|---|---|---|---|---|---|
| Ser | Asn | Ser | Asn | Val | Asn | Arg | Ser | Leu | Ser | Gly | Asp | Gln | Asp | Thr | |
| | 130 | | | | | 135 | | | | | 140 | | | | |

<210> SEQ ID NO 19
<211> LENGTH: 555
<212> TYPE: DNA
<213> ORGANISM: Homo Sapiens
<220> FEATURE:

<221> NAME/KEY: CDS
<222> LOCATION: (1)...(555)

<400> SEQUENCE: 19

| | | | | | | | | | | | | | | | | |
|---|---|---|---|---|---|---|---|---|---|---|---|---|---|---|---|---|
| gac | aga | atc | cct | gct | acc | agt | acg | tct | tca | aat | acc | atc | tca | gca | ggc | 48 |
| Asp | Arg | Ile | Pro | Ala | Thr | Ser | Thr | Ser | Ser | Asn | Thr | Ile | Ser | Ala | Gly | |
| 1 | | | | 5 | | | | | 10 | | | | | 15 | | |
| tgg | gag | cca | aat | gaa | gaa | agt | gaa | gat | gaa | aga | gac | aga | cac | ctc | agt | 96 |
| Trp | Glu | Pro | Asn | Glu | Glu | Ser | Glu | Asp | Glu | Arg | Asp | Arg | His | Leu | Ser | |
| | | | 20 | | | | | 25 | | | | | 30 | | | |
| ttt | tct | gga | tca | ggc | att | gat | gat | gat | gaa | gat | ttt | atc | tcc | agc | acc | 144 |
| Phe | Ser | Gly | Ser | Gly | Ile | Asp | Asp | Asp | Glu | Asp | Phe | Ile | Ser | Ser | Thr | |
| | | | | 35 | | | | | 40 | | | | | 45 | | |
| aat | atg | gac | tcc | agt | cat | agt | aca | acg | ctt | cag | cct | act | gca | aat | cca | 192 |
| Asn | Met | Asp | Ser | Ser | His | Ser | Thr | Thr | Leu | Gln | Pro | Thr | Ala | Asn | Pro | |
| | 50 | | | | | 55 | | | | | 60 | | | | | |
| aac | aca | ggt | ttg | gtg | gaa | gat | ttg | gac | agg | aca | gga | cct | ctt | tca | atg | 240 |
| Asn | Thr | Gly | Leu | Val | Glu | Asp | Leu | Asp | Arg | Thr | Gly | Pro | Leu | Ser | Met | |
| 65 | | | | | 70 | | | | | 75 | | | | | 80 | |
| aca | acg | cag | cag | agt | aat | tct | cag | agc | ttc | tct | aca | tca | cat | gaa | ggc | 288 |
| Thr | Thr | Gln | Gln | Ser | Asn | Ser | Gln | Ser | Phe | Ser | Thr | Ser | His | Glu | Gly | |
| | | | | 85 | | | | | 90 | | | | | 95 | | |
| ttg | gaa | gaa | gat | aaa | gac | cat | cca | aca | act | tct | act | ctg | aca | tca | agc | 336 |
| Leu | Glu | Glu | Asp | Lys | Asp | His | Pro | Thr | Thr | Ser | Thr | Leu | Thr | Ser | Ser | |
| | | | | 100 | | | | | 105 | | | | | 110 | | |
| aat | agg | aat | gat | gtc | aca | ggt | gga | aga | aga | gac | cca | aat | cat | tct | gaa | 384 |
| Asn | Arg | Asn | Asp | Val | Thr | Gly | Gly | Arg | Arg | Asp | Pro | Asn | His | Ser | Glu | |
| | | | 115 | | | | | 120 | | | | | 125 | | | |
| ggc | tca | act | act | tta | ctg | gaa | ggt | tat | acc | tct | cat | tac | cca | cac | acg | 432 |
| Gly | Ser | Thr | Thr | Leu | Leu | Glu | Gly | Tyr | Thr | Ser | His | Tyr | Pro | His | Thr | |
| | 130 | | | | | 135 | | | | | 140 | | | | | |
| aag | gaa | agc | agg | acc | ttc | atc | cca | gtg | acc | tca | gct | aag | act | ggg | tcc | 480 |
| Lys | Glu | Ser | Arg | Thr | Phe | Ile | Pro | Val | Thr | Ser | Ala | Lys | Thr | Gly | Ser | |
| 145 | | | | | 150 | | | | | 155 | | | | | 160 | |
| ttt | gga | gtt | act | gca | gtt | act | gtt | gga | gat | tcc | aac | tct | aat | gtc | aat | 528 |
| Phe | Gly | Val | Thr | Ala | Val | Thr | Val | Gly | Asp | Ser | Asn | Ser | Asn | Val | Asn | |
| | | | | 165 | | | | | 170 | | | | | 175 | | |
| cgt | tcc | tta | tca | gga | gac | caa | gac | aca | | | | | | | | 555 |
| Arg | Ser | Leu | Ser | Gly | Asp | Gln | Asp | Thr | | | | | | | | |
| | | | 180 | | | | | 185 | | | | | | | | |

<210> SEQ ID NO 20
<211> LENGTH: 185
<212> TYPE: PRT
<213> ORGANISM: Homo Sapiens

<400> SEQUENCE: 20

Asp Arg Ile Pro Ala Thr Ser Thr Ser Ser Asn Thr Ile Ser Ala Gly
1               5                   10                  15

Trp Glu Pro Asn Glu Glu Ser Glu Asp Glu Arg Asp Arg His Leu Ser
            20                  25                  30

Phe Ser Gly Ser Gly Ile Asp Asp Asp Glu Asp Phe Ile Ser Ser Thr
        35                  40                  45

Asn Met Asp Ser Ser His Ser Thr Thr Leu Gln Pro Thr Ala Asn Pro
    50                  55                  60

Asn Thr Gly Leu Val Glu Asp Leu Asp Arg Thr Gly Pro Leu Ser Met
65                  70                  75                  80

Thr Thr Gln Gln Ser Asn Ser Gln Ser Phe Ser Thr Ser His Glu Gly
                85                  90                  95

Leu Glu Glu Asp Lys Asp His Pro Thr Thr Ser Thr Leu Thr Ser Ser

```
                        100                 105                 110
Asn Arg Asn Asp Val Thr Gly Gly Arg Arg Asp Pro Asn His Ser Glu
            115                 120                 125

Gly Ser Thr Thr Leu Leu Glu Gly Tyr Thr Ser His Tyr Pro His Thr
    130                 135                 140

Lys Glu Ser Arg Thr Phe Ile Pro Val Thr Ser Ala Lys Thr Gly Ser
145                 150                 155                 160

Phe Gly Val Thr Ala Val Thr Val Gly Asp Ser Asn Ser Asn Val Asn
                165                 170                 175

Arg Ser Leu Ser Gly Asp Gln Asp Thr
            180                 185

<210> SEQ ID NO 21
<211> LENGTH: 561
<212> TYPE: DNA
<213> ORGANISM: Homo Sapiens
<220> FEATURE:
<221> NAME/KEY: CDS
<222> LOCATION: (1)...(561)

<400> SEQUENCE: 21 gac aga atc cct gct acc aca gcc tca gct cat acc agc cat cca atg     48
Asp Arg Ile Pro Ala Thr Thr Ala Ser Ala His Thr Ser His Pro Met
1               5                   10                  15 caa gga agg aca aca cca agc cca gag gac agt tcc tgg act gat ttc     96
Gln Gly Arg Thr Thr Pro Ser Pro Glu Asp Ser Ser Trp Thr Asp Phe
            20                  25                  30 ttc aac cca atc tca cac ccc atg gga cga ggt cat caa gca gga aga    144
Phe Asn Pro Ile Ser His Pro Met Gly Arg Gly His Gln Ala Gly Arg
        35                  40                  45 agg atg gat atg gac tcc agt cat agt aca acg ctt cag cct act gca    192
Arg Met Asp Met Asp Ser Ser His Ser Thr Thr Leu Gln Pro Thr Ala
    50                  55                  60 aat cca aac aca ggt ttg gtg gaa gat ttg gac agg aca gga cct ctt    240
Asn Pro Asn Thr Gly Leu Val Glu Asp Leu Asp Arg Thr Gly Pro Leu
65                  70                  75                  80 tca atg aca acg cag cag agt aat tct cag agc ttc tct aca tca cat    288
Ser Met Thr Thr Gln Gln Ser Asn Ser Gln Ser Phe Ser Thr Ser His
                85                  90                  95 gaa ggc ttg gaa gaa gat aaa gac cat cca aca act tct act ctg aca    336
Glu Gly Leu Glu Glu Asp Lys Asp His Pro Thr Thr Ser Thr Leu Thr
            100                 105                 110 tca agc aat agg aat gat gtc aca ggt gga aga aga gac cca aat cat    384
Ser Ser Asn Arg Asn Asp Val Thr Gly Gly Arg Arg Asp Pro Asn His
        115                 120                 125 tct gaa ggc tca act act tta ctg gaa ggt tat acc tct cat tac cca    432
Ser Glu Gly Ser Thr Thr Leu Leu Glu Gly Tyr Thr Ser His Tyr Pro
    130                 135                 140 cac acg aag gaa agc agg acc ttc atc cca gtg acc tca gct aag act    480
His Thr Lys Glu Ser Arg Thr Phe Ile Pro Val Thr Ser Ala Lys Thr
145                 150                 155                 160 ggg tcc ttt gga gtt act gca gtt act gtt gga gat tcc aac tct aat    528
Gly Ser Phe Gly Val Thr Ala Val Thr Val Gly Asp Ser Asn Ser Asn
                165                 170                 175 gtc aat cgt tcc tta tca gga gac caa gac aca                        561
Val Asn Arg Ser Leu Ser Gly Asp Gln Asp Thr
            180                 185

<210> SEQ ID NO 22
<211> LENGTH: 187
<212> TYPE: PRT
```

<213> ORGANISM: Homo Sapiens

<400> SEQUENCE: 22

```
Asp Arg Ile Pro Ala Thr Thr Ala Ser Ala His Thr Ser His Pro Met
 1               5                  10                  15

Gln Gly Arg Thr Thr Pro Ser Pro Glu Asp Ser Ser Trp Thr Asp Phe
            20                  25                  30

Phe Asn Pro Ile Ser His Pro Met Gly Arg Gly His Gln Ala Gly Arg
        35                  40                  45

Arg Met Asp Met Asp Ser Ser His Ser Thr Thr Leu Gln Pro Thr Ala
    50                  55                  60

Asn Pro Asn Thr Gly Leu Val Glu Asp Leu Asp Arg Thr Gly Pro Leu
65                  70                  75                  80

Ser Met Thr Thr Gln Gln Ser Asn Ser Gln Ser Phe Ser Thr Ser His
                85                  90                  95

Glu Gly Leu Glu Glu Asp Lys Asp His Pro Thr Thr Ser Thr Leu Thr
            100                 105                 110

Ser Ser Asn Arg Asn Asp Val Thr Gly Gly Arg Arg Asp Pro Asn His
        115                 120                 125

Ser Glu Gly Ser Thr Thr Leu Leu Glu Gly Tyr Thr Ser His Tyr Pro
    130                 135                 140

His Thr Lys Glu Ser Arg Thr Phe Ile Pro Val Thr Ser Ala Lys Thr
145                 150                 155                 160

Gly Ser Phe Gly Val Thr Ala Val Thr Val Gly Asp Ser Asn Ser Asn
                165                 170                 175

Val Asn Arg Ser Leu Ser Gly Asp Gln Asp Thr
            180                 185
```

<210> SEQ ID NO 23
<211> LENGTH: 193
<212> TYPE: PRT
<213> ORGANISM: Rattus Norvegicus

<400> SEQUENCE: 23

```
Gln Leu Arg Asn Phe Leu Lys Cys Ser Glu Asp Asn Pro Leu Phe Ala
 1               5                  10                  15

Gly Ile Asp Cys Glu Val Phe Glu Ser Arg Phe Pro Thr Thr Met Ala
            20                  25                  30

Leu Ser Val Leu Val Thr Ile Glu Met Cys Asn Ala Leu Asn Ser Val
        35                  40                  45

Ser Glu Asn Gln Ser Leu Leu Arg Met Pro Pro Trp Leu Asn Pro Trp
    50                  55                  60

Leu Leu Gly Ala Val Val Met Ser Met Ala Leu His Phe Leu Ile Leu
65                  70                  75                  80

Leu Val Pro Pro Leu Pro Leu Ile Phe Gln Val Thr Pro Leu Ser Gly
                85                  90                  95

Arg Gln Trp Gly Val Val Leu Gln Met Ser Leu Pro Val Ile Leu Leu
            100                 105                 110

Asp Glu Ala Leu Lys Tyr Leu Ser Arg His His Val Asp Gly Val Leu
        115                 120                 125

Glu Thr Phe Met Gln Ala Trp Cys Lys Gln Pro Leu Pro Gly Pro His
    130                 135                 140

Thr Thr Arg Gly Trp Leu Pro Gly Cys His Phe Asn Gly Trp Glu Gln
145                 150                 155                 160

Thr Glu Glu Phe Val Phe Ile Gln Glu Arg Trp Thr Val Ser Gly Leu
                165                 170                 175
```

```
Gly Pro Glu Lys Lys Ala Arg Glu Arg Leu Gly Leu Val Ser Ala Ala
            180                 185                 190

Ser

<210> SEQ ID NO 24
<211> LENGTH: 161
<212> TYPE: PRT
<213> ORGANISM: Homo Sapiens

<400> SEQUENCE: 24

Glu Ser Arg Phe Pro Thr Thr Met Ala Leu Ser Val Leu Val Thr Ile
  1               5                  10                  15

Glu Met Cys Asn Ala Leu Asn Ser Val Ser Glu Asn Gln Ser Leu Leu
             20                  25                  30

Arg Met Pro Pro Trp Met Asn Pro Trp Leu Leu Val Ala Val Ala Met
         35                  40                  45

Ser Met Ala Leu His Phe Leu Ile Leu Leu Val Pro Pro Leu Pro Leu
     50                  55                  60

Ile Phe Gln Val Thr Pro Leu Ser Gly Arg Gln Trp Val Val Val Leu
 65                  70                  75                  80

Gln Ile Ser Leu Pro Val Ile Leu Leu Asp Glu Ala Leu Lys Tyr Leu
                 85                  90                  95

Ser Arg Asn His Met His Ala Cys Leu Tyr Pro Gly Leu Leu Arg Thr
            100                 105                 110

Val Ser Gln Ala Trp Ser Arg Gln Pro Leu Thr Thr Ser Trp Thr Pro
        115                 120                 125

Asp His Thr Gly Leu Ala Ser Leu Gly Gln Gly His Ser Ile Val Ser
    130                 135                 140

Leu Ser Glu Leu Leu Arg Glu Gly Gly Ser Arg Glu Glu Met Ser Gln
145                 150                 155                 160

Lys

<210> SEQ ID NO 25
<211> LENGTH: 153
<212> TYPE: PRT
<213> ORGANISM: Homo sapiens

<400> SEQUENCE: 25

Glu Ser Arg Phe Pro Thr Thr Met Ala Leu Ser Val Leu Val Thr Ile
  1               5                  10                  15

Glu Met Cys Asn Ala Leu Asn Ser Val Ser Glu Asn Gln Ser Leu Leu
             20                  25                  30

Arg Met Pro Pro Trp Met Asn Pro Trp Leu Leu Val Ala Val Ala Met
         35                  40                  45

Ser Met Ala Leu His Phe Leu Ile Leu Leu Val Pro Pro Leu Pro Leu
     50                  55                  60

Ile Phe Gln Val Thr Pro Leu Ser Gly Arg Gln Trp Val Val Val Leu
 65                  70                  75                  80

Gln Ile Ser Leu Pro Val Ile Leu Leu Asp Glu Ala Leu Lys Tyr Leu
                 85                  90                  95

Ser Arg Asn His Met His Ala Cys Leu Tyr Pro Gly Leu Leu Arg Thr
            100                 105                 110

Val Ser Gln Ala Trp Ser Arg Gln Pro Leu Thr Thr Ser Trp Thr Pro
        115                 120                 125

Asp His Thr Gly Ala Arg Asp Thr Ala Ser Ser Arg Cys Gln Ser Cys
    130                 135                 140
```

```
Ser Glu Arg Glu Glu Ala Gly Lys Lys
145                 150
```

<210> SEQ ID NO 26
<211> LENGTH: 17
<212> TYPE: PRT
<213> ORGANISM: Homo sapiens

<400> SEQUENCE: 26

```
Leu Ile Leu Val Gly Glu Pro Ser Ile Ser Thr Pro Asp Gly Thr Ile
1               5                   10                  15

Lys
```

<210> SEQ ID NO 27
<211> LENGTH: 101
<212> TYPE: PRT
<213> ORGANISM: Homo sapiens

<400> SEQUENCE: 27

```
Met Glu Asp Asp Glu Leu Thr Asp Ser Lys Leu Pro Ser His Ala Thr
1               5                   10                  15

His Ser Leu Phe Thr Cys Pro Glu Asn Glu Met Val Leu Ser Asn
            20                  25                  30

Ser Arg Ile Gly Lys Arg Arg Gly Glu Pro Leu Ile Leu Val Gly Glu
        35                  40                  45

Pro Ser Ile Ser Thr Pro Asp Gly Thr Ile Lys Asp Arg Arg Leu Phe
50                  55                  60

Met His His Val Ser Leu Glu Pro Ile Thr Cys Val Pro Phe Arg Thr
65                  70                  75                  80

Thr Lys Glu Arg Gln Ile Gln Asn Pro Asn Phe Thr Ala Pro Gly
            85                  90                  95

Gln Glu Phe Leu Ser
            100
```

<210> SEQ ID NO 28
<211> LENGTH: 149
<212> TYPE: PRT
<213> ORGANISM: Homo sapiens

<400> SEQUENCE: 28

```
Ala Glu Lys Gln Ala Lys Ala Arg Glu Ser Gly Ser Ser Thr Ala Glu
1               5                   10                  15

Glu Gly Asp Phe Ser Lys Gly Pro Ile Arg Cys Asp Arg Cys Gly Tyr
            20                  25                  30

Asn Thr Asn Arg Tyr Asp His Tyr Thr Ala His Leu Lys His His Thr
        35                  40                  45

Arg Ala Gly Asp Asn Glu Arg Val Tyr Lys Cys Ile Ile Cys Thr Tyr
50                  55                  60

Thr Thr Val Ser Glu Tyr His Trp Arg Lys His Leu Arg Asn His Phe
65                  70                  75                  80

Pro Arg Lys Val Tyr Thr Cys Gly Lys Cys Asn Tyr Phe Ser Asp Arg
            85                  90                  95

Lys Asn Asn Tyr Val Gln His Val Arg Thr His Thr Gly Glu Arg Pro
            100                 105                 110

Tyr Lys Cys Glu Leu Cys Pro Tyr Ser Ser Ser Gln Lys Thr His Leu
        115                 120                 125

Thr Arg His Met Arg Thr His Ser Val Gly Tyr Gly Tyr His Leu Val
130                 135                 140
```

Ile Phe Thr Arg Val
145

<210> SEQ ID NO 29
<211> LENGTH: 13
<212> TYPE: PRT
<213> ORGANISM: Homo sapiens

<400> SEQUENCE: 29

Val Gly Tyr Gly Tyr His Leu Val Ile Phe Thr Arg Val
 1               5                  10

<210> SEQ ID NO 30
<211> LENGTH: 875
<212> TYPE: DNA
<213> ORGANISM: Homo sapiens

<400> SEQUENCE: 30

| | | | | | |
|---|---|---|---|---|---|
| cgcttggcgg | agctgtacgt | gaagccgggc | aacaaggaac | gcggctggaa | cgacccgccg | 60 |
| cagttctcat | acgggctgca | gacccaggcc | ggcggaccca | ggcgctcgct | gcttaccaag | 120 |
| agggtagccg | caccccagga | tggatccccc | agagtccccg | catcagagac | ttctcctggg | 180 |
| cctcccccaa | tggggcctcc | acctccttca | gtaaggctc | ccaggtcccc | acctgtgggg | 240 |
| agtggtcctg | cctctggcgt | ggagcccaca | agtttcccag | tcgagtctga | ggctgtgatg | 300 |
| gaggatgtgc | tgagaccttt | ggaacaggca | ttggaagact | gccgtggcca | cacaaggaag | 360 |
| caggtatgtg | atgacatcag | ccgacgcctg | gcactgctgc | aggaacagtg | ggctggagga | 420 |
| aagttgtcaa | tacctgtaaa | gaagagaatg | gctctactgg | tgcaagagct | ttcaagccac | 480 |
| cggtgggacg | cagcagatga | catccaccgc | tccctcatgg | ttgaccatgt | gactgaggtc | 540 |
| agtcagtgga | tggtaggagt | taaaagatta | attgcagaaa | agaggagtct | gttttcagag | 600 |
| gaggcagcca | tgaagagaa | atctgcagcc | acagctgaga | agaaccatac | ataccaggc | 660 |
| ttccagcagg | cttcataatc | ctcggttccc | cagactcacc | ggacaccatc | tcctatgcct | 720 |
| tggagacctt | ctgtcacttg | gctcccttct | taccaccacc | aagactgtcc | cactgggcct | 780 |
| gacccaccta | tgagggaaga | agtcccacct | gggccagagg | gagttcatgt | gttactcata | 840 |
| acatgcattt | caataaaaac | atctctgcgg | tggtg | | | 875 |

<210> SEQ ID NO 31
<211> LENGTH: 672
<212> TYPE: DNA
<213> ORGANISM: Homo sapiens

<400> SEQUENCE: 31

| | | | | | |
|---|---|---|---|---|---|
| cgcttggcgg | agctgtacgt | gaagccgggc | aacaaggaac | gcggctggaa | cgacccgccg | 60 |
| cagttctcat | acgggctgca | gacccaggcc | ggcggaccca | ggcgctcgct | gcttaccaag | 120 |
| agggtagccg | caccccagga | tggatccccc | agagaagcag | gtatgtgatg | acatcagccg | 180 |
| acgcctggca | ctgctgcagg | aacagtgggc | tggaggaaag | ttgtcaatac | ctgtaaagaa | 240 |
| gagaatggct | ctactggtgc | aagagctttc | aagccaccgg | tggacgcag | cagatgacat | 300 |
| ccaccgctcc | ctcatggttg | accatgtgac | tgaggtcagt | cagtggatgg | taggagttaa | 360 |
| aagattaatt | gcagaaaaga | ggagtctgtt | ttcagaggag | gcagccaatg | aagagaaatc | 420 |
| tgcagccaca | gctgagaaga | accataccat | accaggcttc | agcaggctt | cataatcctc | 480 |
| ggttccccag | actcaccgga | caccatctcc | tatgccttgg | agaccttctg | tcacttggct | 540 |
| cccttcttac | caccaccaag | actgtcccac | tgggcctgac | ccacctatga | gggaagaagt | 600 |

```
cccacctggg ccagagggag ttcatgtgtt actcataaca tgcatttcaa taaaaacatc   660
tctgcggtgg tg                                                       672
```

<210> SEQ ID NO 32
<211> LENGTH: 598
<212> TYPE: PRT
<213> ORGANISM: Homo sapiens

<400> SEQUENCE: 32

```
Met Ser Asp Asn Gln Ser Trp Asn Ser Gly Ser Glu Glu Asp Pro
 1               5                  10                  15

Glu Thr Glu Ser Gly Pro Pro Val Glu Arg Cys Gly Val Leu Ser Lys
            20                  25                  30

Trp Thr Asn Tyr Ile His Gly Trp Gln Asp Arg Trp Val Val Leu Lys
        35                  40                  45

Asn Asn Ala Leu Ser Tyr Tyr Lys Ser Glu Asp Glu Thr Glu Tyr Gly
50                  55                  60

Cys Arg Gly Ser Ile Cys Leu Ser Lys Ala Val Ile Thr Pro His Asp
65                  70                  75                  80

Phe Asp Glu Cys Arg Phe Asp Ile Ser Val Asn Asp Ser Val Trp Tyr
                85                  90                  95

Leu Arg Ala Gln Asp Pro Asp His Arg Gln Gln Trp Ile Asp Ala Ile
            100                 105                 110

Glu Gln His Lys Thr Glu Ser Gly Tyr Gly Ser Glu Ser Ser Leu Arg
        115                 120                 125

Arg His Gly Ser Met Val Ser Leu Val Ser Gly Ala Ser Gly Tyr Ser
    130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Ala Cys Ala Asp Ala Val Ser Lys Asp
            180                 185                 190

Glu Leu Gln Arg Asp Lys Val Val Glu Asp Asp Glu Asp Phe Pro
        195                 200                 205

Thr Thr Arg Ser Asp Gly Asp Phe Leu His Ser Thr Asn Gly Asn Lys
    210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
            260                 265                 270

Trp Gln Lys Arg Leu Asp Lys Glu Thr Glu Lys Lys Arg Arg Thr Glu
        275                 280                 285

Glu Ala Tyr Lys Asn Ala Met Thr Glu Leu Lys Lys Ser His Phe
    290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                325                 330                 335

Glu Glu Gln Ser Gln Ser Glu Lys Val Arg Leu His Trp Pro Thr Ser
            340                 345                 350

Leu Pro Ser Gly Asp Ala Phe Ser Ser Val Gly Thr His Arg Phe Val
```

```
                355                 360                 365
Gln Lys Val Glu Glu Met Val Gln Asn His Met Thr Tyr Ser Leu Gln
    370                 375                 380

Asp Val Gly Gly Asp Ala Asn Trp Gln Leu Val Val Glu Glu Gly Glu
385                 390                 395                 400

Met Lys Val Tyr Arg Arg Glu Val Glu Glu Asn Gly Ile Val Leu Asp
                405                 410                 415

Pro Leu Lys Ala Thr His Ala Val Lys Gly Val Thr Gly His Glu Val
            420                 425                 430

Cys Asn Tyr Phe Trp Asn Val Asp Val Arg Asn Asp Trp Glu Thr Thr
        435                 440                 445

Ile Glu Asn Phe His Val Val Glu Thr Leu Ala Asp Asn Ala Ile Ile
    450                 455                 460

Ile Tyr Gln Thr His Lys Arg Val Trp Pro Ala Ser Gln Arg Asp Val
465                 470                 475                 480

Leu Tyr Leu Ser Val Ile Arg Lys Ile Pro Ala Leu Thr Glu Asn Asp
                485                 490                 495

Pro Glu Thr Trp Ile Val Cys Asn Phe Ser Val Asp His Asp Ser Ala
            500                 505                 510

Pro Leu Asn Asn Arg Cys Val Arg Ala Lys Ile Asn Val Ala Met Ile
        515                 520                 525

Cys Gln Thr Leu Val Ser Pro Pro Glu Gly Asn Gln Glu Ile Ser Arg
    530                 535                 540

Asp Asn Ile Leu Cys Lys Ile Thr Tyr Val Ala Asn Val Asn Pro Gly
545                 550                 555                 560

Gly Trp Ala Pro Ala Ser Val Leu Arg Ala Val Ala Lys Arg Glu Tyr
                565                 570                 575

Pro Lys Phe Leu Lys Arg Phe Thr Ser Tyr Val Gln Glu Lys Thr Ala
            580                 585                 590

Gly Lys Pro Ile Leu Phe
        595

<210> SEQ ID NO 33
<211> LENGTH: 572
<212> TYPE: PRT
<213> ORGANISM: Homo sapiens

<400> SEQUENCE: 33

Met Ser Asp Asn Gln Ser Trp Asn Ser Gly Ser Glu Glu Asp Pro
1               5                   10                  15

Glu Thr Glu Ser Gly Pro Pro Val Glu Arg Cys Gly Val Leu Ser Lys
                20                  25                  30

Trp Thr Asn Tyr Ile His Gly Trp Gln Asp Arg Trp Val Val Leu Lys
            35                  40                  45

Asn Asn Ala Leu Ser Tyr Tyr Lys Ser Glu Asp Glu Thr Glu Tyr Gly
        50                  55                  60

Cys Arg Gly Ser Ile Cys Leu Ser Lys Ala Val Ile Thr Pro His Asp
65                  70                  75                  80

Phe Asp Glu Cys Arg Phe Asp Ile Ser Val Asn Asp Ser Val Trp Tyr
                85                  90                  95

Leu Arg Ala Gln Asp Pro Asp His Arg Gln Gln Trp Ile Asp Ala Ile
            100                 105                 110

Glu Gln His Lys Thr Glu Ser Gly Tyr Gly Ser Glu Ser Ser Leu Arg
        115                 120                 125

Arg His Gly Ser Met Val Ser Leu Val Ser Gly Ala Ser Gly Tyr Ser
```

```
                130                 135                 140
Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Ala Cys Ala Asp Ala Val Ser Lys Asp
                180                 185                 190

Glu Leu Gln Arg Asp Lys Val Val Glu Asp Glu Asp Asp Phe Pro
                195                 200                 205

Thr Thr Arg Ser Asp Gly Asp Phe Leu His Ser Thr Asn Gly Asn Lys
210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
                260                 265                 270

Trp Gln Lys Arg Leu Asp Lys Glu Thr Glu Lys Lys Arg Arg Thr Glu
                275                 280                 285

Glu Ala Tyr Lys Asn Ala Met Thr Glu Leu Lys Lys Lys Ser His Phe
290                 295                 300

Gly Gly Pro Asp Tyr Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                325                 330                 335

Glu Glu Gln Ser Gln Ser Glu Lys Val Arg Leu His Trp Pro Thr Ser
                340                 345                 350

Leu Pro Ser Gly Asp Ala Phe Ser Ser Val Gly Thr His Arg Phe Val
                355                 360                 365

Gln Lys Glu Glu Gly Glu Met Lys Val Tyr Arg Arg Glu Val Glu Glu
370                 375                 380

Asn Gly Ile Val Leu Asp Pro Leu Lys Ala Thr His Ala Val Lys Gly
385                 390                 395                 400

Val Thr Gly His Glu Val Cys Asn Tyr Phe Trp Asn Val Asp Val Arg
                405                 410                 415

Asn Asp Trp Glu Thr Thr Ile Glu Asn Phe His Val Val Glu Thr Leu
                420                 425                 430

Ala Asp Asn Ala Ile Ile Tyr Gln Thr His Lys Arg Val Trp Pro
                435                 440                 445

Ala Ser Gln Arg Asp Val Leu Tyr Leu Ser Val Ile Arg Lys Ile Pro
450                 455                 460

Ala Leu Thr Glu Asn Asp Pro Glu Thr Trp Ile Val Cys Asn Phe Ser
465                 470                 475                 480

Val Asp His Asp Ser Ala Pro Leu Asn Asn Arg Cys Val Arg Ala Lys
                485                 490                 495

Ile Asn Val Ala Met Ile Cys Gln Thr Leu Val Ser Pro Pro Glu Gly
                500                 505                 510

Asn Gln Glu Ile Ser Arg Asp Asn Ile Leu Cys Lys Ile Thr Tyr Val
                515                 520                 525

Ala Asn Val Asn Pro Gly Gly Trp Ala Pro Ala Ser Val Leu Arg Ala
                530                 535                 540

Val Ala Lys Arg Glu Tyr Pro Lys Phe Leu Lys Arg Phe Thr Ser Tyr
545                 550                 555                 560
```

Val Gln Glu Lys Thr Ala Gly Lys Pro Ile Leu Phe
            565                 570

<210> SEQ ID NO 34
<211> LENGTH: 89
<212> TYPE: PRT
<213> ORGANISM: Homo sapiens

<400> SEQUENCE: 34

Ser Gln Ser Glu Lys Val Arg Leu His Trp Pro Thr Ser Leu Pro Ser
 1               5                  10                  15

Gly Asp Ala Phe Ser Ser Val Gly Thr His Arg Phe Val Gln Lys Pro
             20                  25                  30

Tyr Ser Arg Ser Ser Ser Met Ser Ser Ile Asp Leu Val Ser Ala Ser
         35                  40                  45

Asp Asp Val His Arg Phe Ser Ser Gln Val Glu Glu Met Val Gln Asn
     50                  55                  60

His Met Thr Tyr Ser Leu Gln Asp Val Gly Gly Asp Ala Asn Trp Gln
 65                  70                  75                  80

Leu Val Val Glu Glu Gly Glu Met Lys
                 85

<210> SEQ ID NO 35
<211> LENGTH: 63
<212> TYPE: PRT
<213> ORGANISM: Homo sapiens

<400> SEQUENCE: 35

Gly Leu Pro Leu Ala Glu Ser Leu Lys Arg Leu Met Ser Leu Ser Pro
 1               5                  10                  15

Gly Arg Pro Pro Leu Leu Leu Trp Asp Ala His Val Ala Asp Arg Asp
             20                  25                  30

His Leu Cys Gly Gly Ser Ala His Arg Leu Thr His His Leu Glu Glu
         35                  40                  45

Asp Gly Leu Arg Pro Pro Ala Ala Leu Asp Cys Val Phe Pro Pro
     50                  55                  60

<210> SEQ ID NO 36
<211> LENGTH: 13
<212> TYPE: PRT
<213> ORGANISM: Homo sapiens

<400> SEQUENCE: 36

His Leu Asp Ala Gly Thr Val Glu Pro Lys Arg Glu Lys
 1               5                  10

<210> SEQ ID NO 37
<211> LENGTH: 57
<212> TYPE: PRT
<213> ORGANISM: Homo sapiens

<400> SEQUENCE: 37

Ile Glu Thr Arg Ser Lys Asn Phe Ser Ala Cys Leu Glu Leu Gly Glu
 1               5                  10                  15

Ser Leu Leu Gln Arg Gln His Gln Ala Ser Glu Glu Ile Arg Glu Lys
             20                  25                  30

Leu Gln Gln Val Met Ser Arg Arg Lys Glu Met Asn Glu Lys Trp Glu
         35                  40                  45

Ala Arg Trp Glu Arg Leu Arg Met Ser
     50                  55

```
<210> SEQ ID NO 38
<211> LENGTH: 10
<212> TYPE: PRT
<213> ORGANISM: Homo sapiens

<400> SEQUENCE: 38

Gly Pro Pro Gly Ala Pro Gly Ala Pro Gly
1               5                   10

<210> SEQ ID NO 39
<211> LENGTH: 14
<212> TYPE: PRT
<213> ORGANISM: Homo sapiens

<400> SEQUENCE: 39

Thr Val Leu Leu Arg Leu Gly Ile Thr Trp Gly Lys Val Val
1               5                   10

<210> SEQ ID NO 40
<211> LENGTH: 16
<212> TYPE: DNA
<213> ORGANISM: Homo Sapiens - Alt1

<400> SEQUENCE: 40
tctgtacctg atactc                                                     16

<210> SEQ ID NO 41
<211> LENGTH: 16
<212> TYPE: DNA
<213> ORGANISM: Homo sapiens - Alt2

<400> SEQUENCE: 41
ctacagactg atactc                                                     16

<210> SEQ ID NO 42
<211> LENGTH: 11
<212> TYPE: PRT
<213> ORGANISM: Artificial Sequence
<220> FEATURE:
<223> OTHER INFORMATION: Protein Transduction Domain

<400> SEQUENCE: 42

Tyr Gly Arg Lys Lys Arg Arg Gln Arg Arg
1               5                   10

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
ccgaaaccat gaactttctg c                                               21

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
cttggcgatt tagcagcaga t                                               21
```

```
<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
accctggctt tactgctgta c                                              21

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
aaatggcgaa tccagtccca c                                              21

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
ttactgctgt acctccacca t                                              21

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
gaaggatctc ctcttccttc a                                              21

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
ctgcttgttg cactgctgca g                                              21

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
tctggaaagc agcttgtcac t                                              21

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
```

```
gcccctgtgt cccagtttga t                                              21
```

<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52

```
tacaggtgac tgggttgagc t                                              21
```

<210> SEQ ID NO 53
<211> LENGTH: 21
<212> TYPE: DNA
<213> ORGANISM: Artificial Sequence
<220> FEATURE:
<223> OTHER INFORMATION: Primer

<400> SEQUENCE: 53

```
agccaccaga agaaagtggt g                                              21
```

<210> SEQ ID NO 54
<211> LENGTH: 21
<212> TYPE: DNA
<213> ORGANISM: Artificial Sequence
<220> FEATURE:
<223> OTHER INFORMATION: Primer

<400> SEQUENCE: 54

```
tgtctgggtt gagctctaag c                                              21
```

<210> SEQ ID NO 55
<211> LENGTH: 21
<212> TYPE: DNA
<213> ORGANISM: Artificial Sequence
<220> FEATURE:
<223> OTHER INFORMATION: Primer

<400> SEQUENCE: 55

```
aacatgcact tgctgtgctt c                                              21
```

<210> SEQ ID NO 56
<211> LENGTH: 21
<212> TYPE: DNA
<213> ORGANISM: Artificial Sequence
<220> FEATURE:
<223> OTHER INFORMATION: Primer

<400> SEQUENCE: 56

```
ctctcccgca gtaatccaca t                                              21
```

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57

```
gaggtcaagg cttttgaagg c                                              21
```

<210> SEQ ID NO 58
<211> LENGTH: 21
<212> TYPE: DNA
<213> ORGANISM: Artificial Sequence

```
<220> FEATURE:
<223> OTHER INFORMATION: Primer

<400> SEQUENCE: 58
cttgggcctc tgttaccatg t                                              21

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
gcttttgaag gcaaagacct g                                              21

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
ttaccatgtg gtcccacaga g                                              21

<210> SEQ ID NO 61
<211> LENGTH: 21
<212> TYPE: DNA
<213> ORGANISM: Artificial Sequence
<220> FEATURE:
<223> OTHER INFORMATION: Primer

<400> SEQUENCE: 61
ggagaatgcc ttttgcaaca c                                              21

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
gccattgcat ggaaatgtgg c                                              21

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
caactgctta gtcatcggta g                                              21

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
acttgacaaa gcagtgagct g                                              21
```

```
<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
atgtatggag aatggggaat g                                              21

<210> SEQ ID NO 66
<211> LENGTH: 21
<212> TYPE: DNA
<213> ORGANISM: Artificial Sequence
<220> FEATURE:
<223> OTHER INFORMATION: Primer

<400> SEQUENCE: 66
gttgaatcaa gggttctcct g                                              21

<210> SEQ ID NO 67
<211> LENGTH: 21
<212> TYPE: DNA
<213> ORGANISM: Artificial Sequence
<220> FEATURE:
<223> OTHER INFORMATION: Primer

<400> SEQUENCE: 67
tctcctctgg tatcagcgtc t                                              21

<210> SEQ ID NO 68
<211> LENGTH: 21
<212> TYPE: DNA
<213> ORGANISM: Artificial Sequence
<220> FEATURE:
<223> OTHER INFORMATION: Primer

<400> SEQUENCE: 68
gcactgaatt cctgagtgtc t                                              21

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
tggtgattgt gccttgaagg a                                              21

<210> SEQ ID NO 70
<211> LENGTH: 21
<212> TYPE: DNA
<213> ORGANISM: Artificial Sequence
<220> FEATURE:
<223> OTHER INFORMATION: Primer

<400> SEQUENCE: 70
tccatgcccc ttatcatgga g                                              21

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
```

```
tgaaggacct tggctctgga t                                              21
```

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72

```
aatagagggt aggtaccagc a                                              21
```

<210> SEQ ID NO 73
<211> LENGTH: 12
<212> TYPE: PRT
<213> ORGANISM: Artificial Sequence
<220> FEATURE:
<223> OTHER INFORMATION: VEGF alt splice #1

<400> SEQUENCE: 73

```
Arg Thr Lys Pro Glu Lys Cys Asp Lys Pro Arg Arg
  1               5                  10
```

<210> SEQ ID NO 74
<211> LENGTH: 36
<212> TYPE: DNA
<213> ORGANISM: Artificial Sequence
<220> FEATURE:
<223> OTHER INFORMATION: VEGF alt splice #1 nucleotide

<400> SEQUENCE: 74

```
agaacaaagc cagaaaaatg tgacaagcca aggcgg                              36
```

<210> SEQ ID NO 75
<211> LENGTH: 13
<212> TYPE: PRT
<213> ORGANISM: Artificial Sequence
<220> FEATURE:
<223> OTHER INFORMATION: VEGFB  alt splice #1 peptide

<400> SEQUENCE: 75

```
Val Val Lys Gln Leu Val Gln Thr Pro Pro Leu Pro Pro
  1               5                  10
```

<210> SEQ ID NO 76
<211> LENGTH: 39
<212> TYPE: DNA
<213> ORGANISM: Artificial Sequence
<220> FEATURE:
<223> OTHER INFORMATION: VEGFB  alt splice #1 nucleotide

<400> SEQUENCE: 76

```
gtggtcaaac aactagtgca gacgccgccg cttcctcca                           39
```

<210> SEQ ID NO 77
<211> LENGTH: 12
<212> TYPE: PRT
<213> ORGANISM: Artificial Sequence
<220> FEATURE:
<223> OTHER INFORMATION: VEGFD alt splice #1 peptide

<400> SEQUENCE: 77

```
His Gly Pro Val Lys Met Ser Ser Phe Gln Glu Thr
  1               5                  10
```

<210> SEQ ID NO 78

```
-continued

<211> LENGTH: 36
<212> TYPE: DNA
<213> ORGANISM: Artificial Sequence
<220> FEATURE:
<223> OTHER INFORMATION: VEGFD alt splice #1 nucleotide

<400> SEQUENCE: 78
catggaccag tgaagatgtc ctcattccaa gaaact                                 36

<210> SEQ ID NO 79
<211> LENGTH: 12
<212> TYPE: PRT
<213> ORGANISM: Artificial Sequence
<220> FEATURE:
<223> OTHER INFORMATION: VEGFD  alt splice #2 peptide

<400> SEQUENCE: 79

Leu Glu Arg Ser Glu Ser Cys Glu Asp Arg Cys Pro
 1               5                  10

<210> SEQ ID NO 80
<211> LENGTH: 36
<212> TYPE: DNA
<213> ORGANISM: Artificial Sequence
<220> FEATURE:
<223> OTHER INFORMATION: VEGFD alt splice #2 nucleotide

<400> SEQUENCE: 80
ttggaacgat ctgaaagctg tgaggacaga tgtcct                                 36

<210> SEQ ID NO 81
<211> LENGTH: 13
<212> TYPE: PRT
<213> ORGANISM: Artificial Sequence
<220> FEATURE:
<223> OTHER INFORMATION: VEGF alt splice #1 peptide + C

<400> SEQUENCE: 81

Arg Thr Lys Pro Glu Lys Cys Asp Lys Pro Arg Arg Cys
 1               5                  10

<210> SEQ ID NO 82
<211> LENGTH: 14
<212> TYPE: PRT
<213> ORGANISM: Artificial Sequence
<220> FEATURE:
<223> OTHER INFORMATION: EGFRvIII peptide

<400> SEQUENCE: 82

Leu Glu Glu Lys Lys Gly Asn Tyr Val Val Thr Asp His Cys
 1               5                  10
```

ALTERNATIVE SPLICE FORMS OF PROTEINS AS BASIS FOR MULTIPLE THERAPEUTIC MODALITIES

CROSS REFERENCE TO RELATED APPLICATIONS

This application claims the benefit of U.S. Provisional Application Ser. No. 60/293,791, filed May 25, 2001.

REFERENCE TO GOVERNMENT GRANT

The invention described herein was supported in part by the National Institutes of Health, under grant no. CA69495. The government has certain rights in this invention.

FIELD OF THE INVENTION

The present invention relates to the identification and use of alternative splice forms of proteins for the prophylactic or therapeutic treatment of tumors and other disease states.

BACKGROUND OF THE INVENTION

Traditionally, vaccines are derived from material completely foreign to the organism being vaccinated. Nevertheless, it is often desirable to immunize an organism with a vaccine based on proteins derived from the organism itself. For example, control of inflammation, prevention of ovulation or other forms of contraception, inhibition of Alzhiemer's disease, and prevention or inhibition of tumor growth are all conditions which benefit from immunization with endogenous or "self" proteins.

Peptide vaccines can be used to treat subjects with diseased or abnormal cells; for example, cells infected with viruses, intracellular bacteria or parasites, and tumor cells. The peptide vaccine can induce a cytotoxic T lymphocyte (CTL) response against the diseased or abnormal cells. Cytotoxic T lymphocytes (CTLs) destroy diseased or abnormal cells by direct cytotoxicity, and by providing specific and nonspecific help to other immunocytes such as macrophages, B cells, and other types of T cells. Peptide vaccines can also induce an antibody response, which is useful in the prophylactic and therapeutic treatment of the disease or condition.

Current peptide vaccine technology involves identification of an endogenous normal protein which is associated with the pathogenesis of a given condition. The normal whole protein is then used as the basis for a vaccine. Alternatively, portions of the endogenous protein which are predicted to bind to MHC class I or II motifs are identified and used to produce the vaccine. See Falk et al., *Nature* 351:290, 1991. However, peptide vaccines made only from the partial or whole normal protein sequences can be poorly immunogenic against diseased or abnormal cells, and can also induce an immune reaction against those cells of the body which express the normal protein.

Previous attempts to increase the specific immunogenicity of peptide vaccines have focussed on point mutations in endogenous proteins from various types of cancer cells. These point mutations represent a small area of "non-self" within the larger endogenous protein sequence that may be used to elicit an immune response. However, these point mutations are not effectively recognized by the immune system, and peptide vaccines employing such technology have not produced strong immunologic responses.

Peptide vaccines have also been based on the protein products resulting from gene rearrangements (i.e., deletions, chromosomal rearrangements) that are sometimes present in cancer cells. For example, a chromosome 9:22 translocation in chronic myelogenous leukemia cells produces the BCR/Abl fusion protein. This protein contains an area of "non-self" at the BCR/Abl fusion junction, and has elicited some immunologic response in human patients. However, such gene rearrangements are rare, and chromosomal translocations are only known to occur in cancer. Thus, the usefulness of vaccines produced from protein products derived from chromosomal rearrangements is limited.

Thus, it is desirable to identify endogenous proteins which are specific to certain tissues in a given disease state, and which also contain immunologic areas of "non-self" that produce a strong immune response, such as a CTL or antibody response. Ideally, such altered endogenous proteins would be commonly occurring and induce little or no cross-reactivity to the corresponding normal protein.

Primary RNA transcripts from certain genes can undergo alternative splicing to produce messenger RNA (mRNA) which differs from the majority of the mRNA produced by the gene. These alternatively spliced mRNAs are translated into alternative splice form proteins that contain different amino acid sequences than the corresponding protein produced by normally spliced mRNA. Alternative splice form proteins are often expressed in a tissue-specific manner under certain physiologic or disease states. Consequently, these alternative splice forms are present in a limited number of cells in a subject suffering from a given disease or condition. For example, it is known that many types of cancer cells produce alternative splice forms which are not found in normal cells from the same subject. Other disease states in which alternative splice forms are specifically produced include diabetes, Alzhiemer's disease and systemic lupus erythematosus (SLE). These alternative splice forms have not heretofore been recognized as a source for vaccines directed against cells from diseased or abnormal tissue which produce the alternative splice form.

SUMMARY OF THE INVENTION

It has now been found that peptides derived from alternative splice forms of proteins produced in diseased or abnormal cells are highly immunogenic. Such peptides elicit a strong immune response specific to the "non-self" portion of the peptide. In particular, the peptides can elicit a specific CTL response. The peptides can be used in the therapeutic or prophylactic treatment of a disease or condition which is characterized by the presence of the alternative splice form in certain cells.

The invention thus provides a peptide comprising an amino acid sequence unique to an alternative splice form, wherein the alternative splice form is produced by diseased or abnormal cells of a subject but is substantially absent from the subject's normal cells.

The invention also provides a method of identifying immunogenic peptides for treating a subject who has, or is at risk for having, a disease or condition in which diseased or abnormal cells produce at least one alternative splice form, which alternative splice form is substantially absent from normal cells. The method comprises the steps of identifying at least one mRNA which encodes for the at least one alternative splice form; determining at least a partial amino acid sequence of the at least one alternative splice form; and generating at least one peptide comprising an amino acid sequence which is unique to the alternative splice form.

The invention also provides a method of treating a subject who has, or is at risk for having, a disease or condition in which diseased or abnormal cells produce at least one alternative splice form, which alternative splice form is substantially absent from normal cells. The method comprises administering to the subject an effective amount of at least one peptide comprising an amino acid sequence which is unique to the alternative splice form such that an immune response is generated against the diseased or abnormal cells.

The invention further provides a method of preventing or delaying the onset of tumor development in a subject at risk for having a tumor in which tumor cells produce at least one alternative splice form, which alternative splice form is substantially absent from non-tumor cells. The method comprises administering to a subject an effective amount of at least one peptide comprising an amino acid sequence which is unique to the alternative splice form, such that an immune response is generated against the tumor cells.

The invention further provides a method of regressing a tumor in a subject having a tumor in which tumor cells produce at least one alternative splice form, which alternative splice form is substantially absent from non-tumor cells. The method comprises administering to a subject an effective amount of at least one peptide comprising an amino acid sequence which is unique to the alternative splice form, such that an immune response is generated against the tumor cells.

The invention also provides a method for identifying peptides of the invention which induce MHC-restricted cytotoxic T lymphocyte responses in a subject, comprising obtaining peripheral blood lymphocytes (PBLs), exposing the PBLs to one or more of the peptides such that the PBLs are stimulated, incubating the stimulated PBLs with either target cells that endogenously synthesize the alternative splice form from which the peptide is derived or pulsing the target cells with peptide, and detecting lysis of the target cells.

For example, the target cells can be autologously labeled with a radioactive or fluorescent substance. Detecting lysis of the target cells can be accomplished by measuring the amount of autologous label released from the target cells which are lysed by the activated PBLs. Lysis of the target cells can also be detected with an enzyme-linked immunospot ("ELISPOT") assay.

The invention also provides antibodies that bind to specific epitopes on alternative splice forms or peptides comprising an amino acid sequence unique to an alternative splice form. The antibodies can be monoclonal or polyclonal, or can be an antibody fragment that is capable of specifically binding to an alternative splice form epitope.

The invention also provides a hybridoma that produces a monoclonal antibody which specifically binds alternative splice forms or peptides comprising an amino acid sequence unique to an alternative splice form.

The invention further provides a method of treating a subject having, or at risk for having, a disease or condition in which diseased or abnormal cells produce at least one alternative splice form, which alternative splice form is substantially absent from normal cells. The method comprises administering to a subject an effective amount of at least one antibody specific to an amino acid sequence unique to the alternative splice form, such that one or more clinical symptoms in the subject are ameliorated, or the number of diseased or abnormal cells in the subject is reduced.

AMINO ACID ABBREVIATIONS

The nomenclature used to describe the peptide compounds of the present invention follows the conventional practice wherein the amino group is presented to the left and the carboxy group to the right of each amino acid residue. In the formulae representing selected specific embodiments of the present invention, the amino-and carboxy-terminal groups, although not specifically shown, will be understood to be in the form they would assume at physiologic pH values, unless otherwise specified. In the amino acid structure formulae, each residue is generally represented by a one-letter or three-letter designation, corresponding to the trivial name of the amino acid, in accordance with the following schedule:

| A | Alanine | Ala |
|---|---|---|
| C | Cysteine | Cys |
| D | Aspartic Acid | Asp |
| E | Glutamic Acid | Glu |
| F | Phenylalanine | Phe |
| G | Glycine | Gly |
| H | Histidine | His |
| I | Isoleucine | Ile |
| K | Lysine | Lys |
| L | Leucine | Leu |
| M | Methionine | Met |
| N | Asparagine | Asn |
| P | Proline | Pro |
| Q | Glutamine | Gln |
| R | Arginine | Arg |
| S | Serine | Ser |
| T | Threonine | Thr |
| V | Valine | Val |
| W | Tryptophan | Trp |
| Y | Tyrosine | Tyr |

DEFINITIONS

The expression "amino acid" as used herein is meant to include both natural and synthetic amino acids, and both D and L amino acids. "Standard amino acid" means any of the twenty L-amino acids commonly found in naturally occurring peptides. "Nonstandard amino acid" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half life without adversely affecting their biological activity. Additionally, a disulfide linkage may be present or absent in the peptides of the invention.

Amino acids have the following general structure:

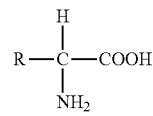

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

"Antibody" as used herein includes polyclonal and monoclonal antibodies, chimeric, single chain, chimeric and humanized antibodies, as well as Fab fragments, including the products of an Fab or other immunoglobulin expression library.

The term "humanized antibody" refers to an antibody that has its complementary determining regions (CDRs) derived from a non-human species immunoglobulin, and the remainder of the antibody molecule derived from a human immunoglobulin.

The term "chimeric antibody" means an antibody comprising a variable region and a constant region derived from different species.

The term "chimeric humanized antibody" is meant a chimeric antibody in which at least the constant region is human-derived.

"Peptide" and "protein" are used interchangeably, and refer to a compound comprised of at least two amino acid residues covalently linked by peptide bonds or modified peptide bonds (e.g., peptide isosteres). No limitation is placed on the maximum number of amino acids which may comprise a protein or peptide. The amino acids comprising the peptides or proteins described herein and in the appended claims are understood to be either D or L amino acids with L amino acids being preferred. The amino acid comprising the peptides or proteins described herein may also be modified either by natural processes, such as posttranslational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide. Also, a given peptide may contain many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins—Structure and Molecular Properties,* 2nd Ed., T. E. Creighton, W.H. Freeman and Company, New York, 1993 and Wold F, Posttranslational Protein Modifications: Perspectives and Prospects, pgs. 1-12 in *Posttranslational Covalent Modification of Proteins,* B. C. Johnson, Ed., Academic Press, New York, 1983; Seifter et al., "Analysis for protein modifications and nonprotein cofactors," *Meth. Enzymol.* (1990) 182: 626-646 and Rattan et al. (1992), "Protein Synthesis: Posttranslational Modifications and Aging," *Ann NY Acad Sci* 663: 48-62.

As used herein, "reading frame" means a specific series of codons in a nucleic acid, for example an mRNA, which produce a given polypeptide when translated.

BRIEF DESCRIPTION OF THE FIGURES

FIGS. 3A and 3B are survival plots of number of tumors per mouse vs. days after birth and total tumor volume in each mouse vs. days after birth, respectively, for MMTV-neu mice treated with immunogenic peptides derived from VEGF family member alternative splice forms. For both figures, nine litter mate female mice either are left untreated ("No treatment"), given GM-CSF only ("GM-CSF"), or given a combination of VEGF family based alternative splice form vaccines with GM-CSF ("Combo"). Each curve on the survival plots represents a single animal.

DETAILED DESCRIPTION OF THE INVENTION

Figures 1A, 1B:
FIG. 1A is a photograph of an agarose gel electrophoresis showing the PCR product representing alternative splice form #1 in VEGFD (SEQ ID NO: 77). Shown is the third round of PCR using primer set 3. The strong band of ~300 bp (labeled as "VEGFD#1") represents SEQ ID NO: 77; the band of 1082 bp (labeled as "VEGFD") represents the expected normally spliced mRNA. M: molecular weight in bp; HC2: PCR amplification from HC2 20d2/c cells.
FIG. 1B is a photograph of an agarose gel electrophoresis showing the results of the PCR amplification of NIH-3T3 cells. Shown is the third round of PCR using primer set 3. Only the band corresponding to the expected normally spliced mRNA is present (labeled as "VEGFD"). M: molecular weights in bp; NIH: PCR amplification from NIH-3T3 cells.

Alternative splice forms (also referred to as "alternative splice form proteins") comprise amino acid sequences not found in the corresponding normal proteins. An amino acid sequence found only in the alternative splice form and not in the corresponding normal protein is considered "unique" to the alternative splice form.

Peptides comprising amino acid sequences which are unique to alternative splice forms are therefore highly immunogenic. As used herein, a "normal" protein is any protein produced from mRNA transcripts which comprise the majority of the total mRNA transcripts produced by a given gene. For example, if two mRNA transcripts are produced by a gene, the mRNA transcript which comprises greater than 50% of the total mRNA transcripts produced by the gene is considered a normally spliced mRNA transcript which is translated into the "normal" protein. The mRNA transcript which comprises less than 50% of the total mRNA produced by the gene is considered an alternatively spliced mRNA, and is translated into an alternative splice form. If three or more mRNA transcripts are produced from a gene, the mRNA transcript which is present in the greatest proportion relative to the other mRNA transcripts is considered a normally spliced mRNA transcript which is translated into the "normal" protein. Those mRNA transcripts which are present in lesser proportions relative the normally spliced mRNA are considered an alternatively spliced mRNA, and are translated into alternative splice forms. By way of example, if a gene produces three mRNA transcripts in the relative proportions of 40:35:25, the mRNA which comprises 40% of the total mRNA transcripts produced is considered the normally spliced mRNA. The two mRNA transcripts comprising, respectively, 35% and 25% of the total mRNA transcripts produced are considered alternative splice forms.

For purposes of the invention, it is assumed that the level of normal or alternatively spliced mRNA produced by a gene is directly proportional to the level of protein produced from the mRNA. The amount of alternatively spliced mRNA, and thus of alternative splice form, in a cell is often a relatively small proportion of the total mRNA transcripts produced by the gene. For example, the alternative splice form can represent 10% or less, 5% or less, 1% or less or 0.5% to 0.1% or less of the total output of a given gene.

The relative amount of mRNA transcripts produced from a gene can be measured by techniques well-known in the art; for example by quantitative reverse-transcriptase polymerase chain reaction (RT-PCR) techniques such as those described in Siebert P D (1993), "Quantitative RT-PCR," Clontech Laboratories, Inc., Palo Alto, Calif.; Carango P et al. (1995), *Ann. Neurol.* 38: 610-617; and Grove D S (1999), *J. Biomolecular Techniques* 10: 11-16, the entire disclosures of which are herein incorporated by reference. Amounts of mRNA transcripts are typically expressed in relative units (e.g., relative fluorescence units), but can be expressed in terms of mass (e.g., micrograms) or moles (e.g., gram molecular weight).

The amount of an alternative splice form in a diseased or abnormal cell (as evaluated either at the protein or mRNA level) can be at least 50% greater than the level of the same alternative splice form which is found in a normal cell. A "diseased" or "abnormal" cell is identified by certain phenotypic abnormalities which are readily recognized by those skilled in the art upon examination of cells or tissue. For example, the pathology and histopathology of different cancers is described in *Cancer: Principles and Practice of Oncology*, (3rd edit., DeVita V T, Hellman S, and Rosenberg S A, eds.), 1989, J. B. Lipincott Co., Phila., Pa., the entire disclosure of which is herein incorporated by reference.

Cells which are tumorigenic or neoplastic can also be identified by certain growth characteristics and morphology exhibited by the cell in culture. Tumorigenic or neoplastic cells are insensitive to contact-induced growth inhibition, and the cells form foci in the culture vessel when cultured for extended periods. Tumorigenic or neoplastic cells also exhibit characteristic morphological changes, disorganized patterns of colony growth, and the acquisition of anchorage-independent growth. Tumorigenic or neoplastic cells also have the ability to form invasive tumors in susceptible animals, which can be assessed by injecting the cells, for example, into athymic mice or newborn animals of the same species using techniques well-known in the art.

Histological, cell culture-based, and other techniques for identifying other types of diseased or abnormal cells are also well-known in the art.

As used herein, an alternative splice form which is "substantially absent from normal cells" means the alternative splice form is not present in the normal cells or is present in a negligible amount, and in any case is not present in more than about 66% of the level found in a diseased or abnormal cell. An immune response directed specifically against diseased or abnormal cells can therefore be generated in a subject by administering one or more peptides comprising amino acid sequences which are unique to the alternative splice form. Immunization with such peptides has the advantage of not eliciting an immune response against normal cells.

One type of alternative splice form contains a novel amino acid sequence formed by the joining of two normally distant amino acid sequences. This type of alternative splice form is created when an mRNA is spliced so as to skip all or part of an exonic sequence which is normally translated into the protein, but which leaves the normal reading frame intact. A novel amino acid sequence is thus created at the "splice junction" by the juxtaposition of two "normal" amino acids which were not heretofore adjacent. Amino sequences from the normal protein flank the splice junction. The skipping of exonic sequences may also create a new codon without shifting the reading frame of the mRNA. In this instance, a new amino acid is inserted at the splice junction which is flanked by normal amino acid sequences. Both types of splice junctions are considered immunologic "non-self" sequences.

Another type of alternative splice form contains novel amino acid sequences translated from coding sequences which are not normally present in the mRNA. Such coding sequences are created by alternative splice events in which intronic sequences, or exonic sequences not typically translated into the normal protein, are included in the mRNA. The coding sequences can also be created by alternative splicing events which alter the native reading frame of the mRNA, resulting in translation of a "missense" amino acid sequence downstream of the alternative splice site. The novel amino acid sequences are considered immunologic "non-self" sequences.

Genes which are involved in a particular disease process, and which are likely to produce alternatively spliced mRNAs, often exhibit altered expression patterns in diseased or abnormal cells as compared to cells from normal tissue.

For example, angiogenesis (the formation of new blood vessels) is a critical process for the continued growth of tumors. Some of the most potent factors for angiogenesis identified in tumors are members of the vascular endothelial growth factor (VEGF) protein family, which are upregulated in tumor cells. The VEGF proteins include VEGF, VEGF-B, VEGF-C, VEGF-D, and placental growth factor (PlGF). The mRNA which produces the VEGF proteins can undergo a variety of splicing events.

Many other genes which produce alternatively spliced mRNAs in a disease-specific manner are known in the art, and can be used in the practice of the present invention. Table 1 contains a representative list of such genes, the diseases or conditions with which they are associated, the alternative splice forms produced by those genes, and peptides of the invention derived from the alternative splice forms.

TABLE 1

| Disease | Journal reference[1] | Gene affected (catagory of protein) | Nature of alternative splice and sequence of peptide derived from alternative splice form | GenBank accession number of gene or gene product[2] and SEQ ID NO. of alternative splice form (full of partial sequence) |
| --- | --- | --- | --- | --- |
| Acute promyelocytic leukemia | Proc. Natl. Acad Sci. (USA) 99:7640-7645 (2002) | Retinoic acid receptor-alpha (signal transduction protein) | Inclusion of 2$^{nd}$ intron in RAR-alpha gene, in-frame (underlined): NSNHVASGAPVCHNPNLPSWQGALGP YGVVVLAPDTWLSSLRLSSSPGVEGRS CSARETQA [SEQ ID NO: 3] | AC090426 |
| Myeloblastic leukemia | J. Biol. Chem., Vol. 275, Issue 33, 25255-25261 | MCL-1 (transcription factor) | Novel sequences after junction: RNHETAFQ GWVCGVLPCR [SEQ ID NO: 2] | AF203373 [SEQ ID NO: 1] |
| Response to stress, infection | J. Biol. Chem., Vol. 276, Issue 31, 29037-29044 | Interleukin-1 Receptor-associated Kinase (signal transduction) | In-frame deletion of 30 amino acids (residues 514-543). Deleted region is VYERLEKLQAVVAGVPGHLEAASCIPP SRQ [SEQ ID NO 5] | U52112 [SEQ ID NO: 4] |
| Thyroid hormone repression | J. Biol. Chem., Vol. 276, Issue 51, 48196-48205 | Branched-chain Aminotransferase (metabolism) | 36-bp gap (corresponding to nucleotides 1030-1065 of BCATm) located near the carboxyl terminus | U68418 [SEQ ID NO: 6] |
| Immunity/ inflammation | J Biol Chem, Vol. 274, Issue 39, 27857-27866 | Human Glucocorticoid Receptor Beta Isoform (signal transduction) | hGRbeta has additional nonhomologous 15 amino acids at C terminus. | |
| Oncogenic progression | J Biol Chem, Vol. 273, Issue 43, 28208-28218 | Bile salt-dependent lipase (BSDL) (body metabolism) | Underlined is novel sequence: APVPPTGDSGAPPVPP [SEQ ID NO: 8] | AF081673 [SEQ ID NO: 7] |
| Endothelial cell activation | J Biol Chem, Vol. 274, Issue 3, 1415-1422 | Variant of HOXA9 (transcription factor) | Inframe junction of sequences: DKPPIDP NNPAANW [SEQ ID NO: 10] | U82759 [SEQ ID NO: 9] |
| Regulation of Folate | J Biol Chem 271: 23820-23827 | Folylpolyglutamate Synthetase Gene (metabolism) | Alternate exon: AVSARGATTEGPARRGMS [SEQ ID NO: 12] | U33557 [SEQ ID NO: 11] |
| Cancer | J. Biol Chem, 267: 4732-4739, 1992 | CD44 splicing variants (cell adhesion/signal transduction) | Five different splicing variants inserted into CD44 coding sequence, all inframe | M83324 [SEQ ID NOS: 13 & 14] M83325 [SEQ ID NOS: 15 & 16] M83326 [SEQ ID NOS: 17 & 18] M83327 [SEQ ID NOS: 19 & 20] M83328 [SEQ ID NOS: 21 & 22] |
| Uterine cancer | Cancer Research, Vol. 54, Issue 13 3337-3341 | CD44 | Containing variant exons v3 to v10, including the v7/v8 transition epitope | |
| Thyroid cancer | Cancer Research, Vol. 56, Issue 5 1037-1042 | CD44 | Contains subsegment from exon 4 joined to a subsegment of exon 13 (v8), followed by the complete sequence of exons 14 and 15 | |
| Gastointenstinal tumors | Cancer Research, Vol. 55, Issue 19 4273-4277 | CD44 | Retention of intron 9 | |
| Dysplastic, and neoplastic cervical epithelium | Clinical Cancer Research Vol. 1, Issue 10 1125-1132 | CD44 variants | | |
| Melanoma | Clinical Cancer Research Vol. 2, Issue 3 447-456 | CD44 variants | | |
| Atherosclerosis | J Biol Chem 268: 17528-17538, 1993 | Variant of Human VLDL receptor (lipid metabolism) | Lacks 84 nucleotides | |
| Allergic response | J Biol Chem 264: 5912-5915 | Variants of IgE receptor alpha chain (receptor/signal transduction) | Exon 2 or part of exon 4 missing | |
| Cardiac Function | J. Biol. Chem. In press | Sarco/Endoplasmic Reticulum Ca2 + ATPase (SERCA) 3 isoforms (ion channels) | Three novel splice forms | AF458230 [SEQ ID NO: 23] AF458229 [SEQ ID NO: 24 AF458228 [SEQ ID NO: 25] |
| Breast Cancer | Cancer Research 59, 2546-2550 | BRCA2 (DNA repair) | Junction of exon 11 to 13 inframe LILVGEPSI STPDGTIK [SEQ ID NO: 26] | U43746 [SEQ ID NO: 27] |
| Prostate Cancer | Cancer Research, Vol. 54, Issue 5 1190-1193 | Estrogen receptor | Variant lacking all of exon 4 | |

TABLE 1-continued

| Disease | Journal reference[1] | Gene affected (catagory of protein) | Nature of alternative splice and sequence of peptide derived from alternative splice form | GenBank accession number of gene or gene product[2] and SEQ ID NO. of alternative splice form (full of partial sequence) |
|---|---|---|---|---|
| Breast Cancer | Cancer Research, Vol. 53, Issue 24 5934-5939 | Constitutively active estrogen receptor (hormone metabolism/signal transduction) | Lack of exon 5 | |
| Breast Cancer | Cancer Research, Vol. 56, Issue 19 4324-4327 | exon 4-deleted estrogen receptor mRNA, deleted in exons 2-4 or in regions within exons 3-7 | | |
| Small Cell lung cancer | Cancer Research 60, 1840-1844 | Neuron-restrictive Silencer factor Repressor (transcriptional regulation) | Novel exon inserted: VGYGYHLVIFTRV [SEQ ID NO: 29] | AF228045 [SEQ ID NO: 28] |
| Lung Cancer | Cancer Research, Vol. 57, Issue 11 2256-2267 | FHIT gene (nucleotide metabolism) | Various deletions of coding exons or insertions of novel exons | |
| Breast Cancer | Cancer Research, Vol. 56, Issue 21 4871-4875 | FHIT gene (nucleotide metabolism) | Additional 32 amino acids at amino terminus due to splicing | |
| Breast Cancer | Cancer Research 59, 4190-4193 | Steroid Receptor RNA Activator (hormone metabolism) | Deletion of 203 bp between 155 and 357 [SEQ ID NO: 31] | AF092038 [SEQ ID NO: 30] |
| Acute lymphoblastic leukemia | Cancer Research, Vol. 56, Issue 9 2171-2177 | ALL-1 gene (transcription factor) | Deletion of exon 8 | |
| Endometrial hyperplasia | Cancer Research, Vol. 58, Issue 12 2500-2503 | PTEN gene (signal transduction) | 4 bp deletion in exon 8 | |
| Endometrial Cancer | Cancer Research, Vol. 57, Issue 24 5579-5583 | Sex hormone binding globulin (hormone metabolizm) | Deletion of entire exon VII | |
| Teratocarcinoma | Cancer Research, Vol. 54, Issue 1 220-225 | PDGF-alpha receptor (receptor/signal transduction) | Lacks exon 14 | |
| Colon Cancer | Cancer Research, Vol. 56, Issue 8 1731-1736 | DT-diaphorase (drug detoxification) | Deletion of exon 4 | |
| Breast Cancer | Clinical Cancer Research Vol. 6, 1135-1139 | SHC gene (signal transduction) | p66 isoform | |
| Desmoplastic round cell tumors | Clinical Cancer Research Vol. 6, 3522-3529 | EWS gene (transcription factor) | Deletion of exons 5, 6, 7 or 8 | |
| Muscle development | Proc. Natl Acad Sci 92:2686-2690 | Nicotinic acetylcholine receptor (neurotransmission/signal transduction) | Inframe deletion of exon 5 | |
| Epithelial neoplasias | Cell Growth & Differentiation, Vol. 6, Issue 9 1185-1191 | Tuberous sclerosis gene (signal transduction) | Deletion from amino acids 947 to 990, (deletion fo 129-bp exon), inclusion of separate 69-bp exon encoding a novel serine-rich amino acid sequence (1272 to 1295) | |
| Gastric cancer | Molecular and Cellular Biology, Oct. 1996, p. 5518-5526 | Ron (tyrosine kinase receptor/signal transduction) | Joining of 2677 to 2825 (inframe deletion of 147 bp exon) | |
| Breast and ovarian cancer | Molecular and Cellular Biology, 17:444-452 | BRCA1 (DNA repair) | Inframe deletion of exon 11 | |
| Phenylketonuria | J. Biol. Chem 266: 9351-9354, 1991 | Phenylalanine Hydroxylase gene (metabolism) | Deletion of Ile at position 94 or 95 | |
| X-linked agamma-globulinemia (immunodeficiency disorder) | J. Bio. Chem. 271:30303-30306 | Bruton's tyrosine kinase (signal transduction) | Deletion of 33 amino acids (amino acid residues 48-80) | |
| Hereditary elliptocytosis (anemia) | J. Biol. Chem. 266:15154-15159, 1991 | | Deletion of exon X, out of frame after junction | J05500 [SEQ ID NO: 37] |
| Osteogenesis imperfecta | J. Biol. Chem. 266, No. 33, Issue of November 25, pp, 22370-22374 | Pro-a1(I) collagen (connective tissue) | Inframe 9 bp (3 amino acid) deletion GPPGA^PGAPG [SEQ ID NO: 38] | |
| Defective apoptosis | J. Biol. Chem. 273:303139-30146 | Bcl-2-related ovarian killer (apoptosis regulation) | Deletion of amino acid 76-118 TVLLRLG^ITWGKVV [SEQ ID NO: 39] | |
| Alzheimer's disease | J. Biol. Chem. 267:10804-10809 | Beta-A4 amyloid precursor protein (amyloid protein) | Inframe deletion of exon 15 | |

TABLE 1-continued

| Disease | Journal reference[1] | Gene affected (catagory of protein) | Nature of alternative splice and sequence of peptide derived from alternative splice form | GenBank accession number of gene or gene product[2] and SEQ ID NO. of alternative splice form (full of partial sequence) |
|---|---|---|---|---|
| Alcoholism | J. Bio. Chem. 276: 29764-29771 | N-Methyl-D-aspartate R1 (neurotransmission/signal transduction) | Eight isoforms generated by alternative splicing of exons 5, 21, and 22 | |
| Goodpasture disease autoimmunity) | J. Bio. Chem. 275: 40392-40399 | Goodpasture antigen-binding protein (serine/threonine kinase, signal transduction) | Deletion from 1519-1596 (amino acids 371-396) | AF232930 [SEQ ID NO: 32] (normal) and [SEQ ID NO: 33] (alternative splice form) AF232935 [SEQ ID NO 34] (alternative splice form partial sequence) |
| Induction of apoptosis | J Biol Chem. 273:11930-11936 | BAX (apoptosis regulation) | Insertion of 49 bp, novel C-terminus: GLPLAESLKRLMSLSPGRPPLLLWDAH VADRDHLCGGSAHRLTHHLEEDGLRP PAALDCVFPP [SEQ ID NO: 35] | |
| Systemic Lupus Erythematosus | Biochemical and Biophysical Research Communications 272, 877-881 | Caspase-8 (apoptosis regulation) | Alternative splicing of intron 8, frameshift after junction (underlined) HLDAG<u>TVEPKREK</u> [SEQ ID NO: 36] | |
| Diabetes (non insulin dependent diabetes) | Biochemical and Biophysical Research Communications 181:1419-1424 | Insulin receptor (receptor/signal transduction) | Alternative splicing of exon 11 resulting in 12 additional amino acids at C-terminus | |
| Pelizaeus-Merzbacher Disease | Annals of Neurology 1995, 38, pp. 610-617 | DM20 – Myelin Component | Two alternative splice forms of DM20 – Alt 1 is a fragment of 224 by encompassing nucleotides −20 to +369 in which 162 bp of exon II (from+4 to +166) has been removed, leaving the reading frame intact but substituting Asp for Gly2. Alt 2 is a fragment of 253 bp from −20 to +369 in which 133 bp (from +33 to +166) is spliced out from exon II, shifting the mRNA out of frame after the splice. | [SEQ ID NOS: 40 & 41] (nucleotide sequence of splice junctions) |

[1] The entire disclosure of each journal article is herein incorporated by reference.
[2] The entire disclosure of each GenBank record is herein incorporated by reference.

As can be seen from Table 1, certain types of diseases or conditions tend to produce diseased or abnormal cells containing alternative splice forms. For example, alternative splice forms are present in diseased or abnormal cells caused by infections or stress; cancers (e.g., acute promyelocytic leukemia; acute lymphoblastic leukemia; myeloblastic leukemia; uterine cancer; thyroid cancer; gastrointestinal tumors; dysplastic and neoplastic cervical epithelium; melanoma; breast cancer; prostate cancer; lung cancer; endometrial cancer; teratocarcinoma; colon cancer; desmoplastic round cell tumors; epithelial neoplasias; gastric cancer; ovarian cancer); disorders or conditions of the immune system (e.g., allergic response, x-linked agammaglobulinemia, immunity/inflammation, systemic lupus erythematosus, Goodpasture disease); metabolic disorders (e.g., phenylketonuria, non-insulin dependent diabetes); collagen disorders (e.g., osteogenesis imperfecta); disorders of the arteries (atherosclerosis); inherited red cell membrane disorders (e.g., hereditary elliptocytosis); thyroid hormone repression; endometrial hyperplasia; Alzheimer's disease; and alcoholism.

Within a particular type of disease or condition, alternative splice forms tend to be produced from certain genes. For example, in cancer, the CD44 gene; steroid hormone receptors genes (such as the estrogen receptor gene) and the FHIT gene produce a variety of alternative splice forms from which peptides of the invention can be derived.

One of ordinary skill in the art can identify other genes which potentially produce alternative splice forms using well-known techniques, including linkage analysis, gene expression array analysis, homology searches, and point mutation analysis, and commercially available computer software which can be used to predict exon usage in a given nucleic acid sequence.

The mRNA transcribed from genes which are involved in a particular disease process can be analyzed for the presence of alternative splice patterns using techniques well-known in the art. Such techniques include reverse transcription-polymerase chain reactions (RT-PCR), northern blotting and in-situ hybridization. Techniques for analyzing mRNA sequences are described, for example, in Busting S A (2000), *J. Mol. Endocrinol.* 25: 169-193, the entire disclosure of which is herein incorporated by reference. Representative techniques for identifying alternatively spliced mRNAs are also described below.

For example, databases that contain nucleotide sequences related to a given disease gene can be used to identify alternatively spliced mRNA. Databases which include nucleotide sequences include GenBank, Embase, and the Cancer Genome Anatomy Project (CGAP) database. The CGAP database, for example, contains expressed sequence tags (ESTs) from various types of human cancers. An mRNA or gene sequence can be used to query such a database to determine whether ESTs representing alternatively spliced mRNAs have been found for a particular gene expressed in a given disease state.

A technique called "RNAse protection" can also be used to identify alternatively spliced mRNAs. RNAse protection involves translation of a gene sequence into synthetic RNA, which is hybridized to RNA derived from diseased or abnormal cells. The hybridized RNA is then incubated with enzymes that recognize RNA:RNA hybrid mismatches. Smaller than expected fragments indicate the presence of alternatively spliced mRNAs. The putative alternatively spliced mRNAs can be cloned and sequenced by methods well known to those skilled in the art.

The technique of reverse transcription coupled with the polymerase chain reaction ("RT-PCR") can also be used to identify alternatively spliced mRNAs. In RT-PCR, mRNA from the diseased tissue is converted into cDNA by the enzyme reverse transcriptase, using methods well-known to those of ordinary skill in the art. The entire coding sequence of the cDNA is then amplified via PCR using a forward primer located in the 3' untranslated region and a reverse primer located in the 5' untranslated region. The amplified products can be analyzed for alternative splice forms, for example by comparing the size of the amplified products with the size of the expected product from normally spliced mRNA. A preferred method of determining the relative size of the amplified products is gel electrophoresis through agarose gels. Any change in the size of the amplified product can indicate alternative splicing.

If the first round of PCR yields an indistinct product band, for example when analyzed by agarose gel electrophoresis, a portion of the initial PCR reaction can be used in second round of amplification. The second round of amplification preferably employs a set of primers that are internal to the first set of primers. This process, called "nested PCR," is well known to those of ordinary skill in the art. If the amplified products still produce an indistinct band on an agarose gel after the second round of amplification, a third round of nested PCR may be performed. Once a distinct band representing the amplification product is produced, the band is excised from the gel, and the DNA is extracted and sequenced according to known techniques (e.g., the dideoxy-chain termination method according to Sanger et al. (1977), *Proc. Natl. Acad. Sci. USA* 74: 5463, the entire disclosure of which is herein incorporated by reference).

Once an alternatively spliced mRNA is identified, the amino acid sequence of all or part of the alternative splice form encoded by the mRNA can be determined by translating the mRNA sequence according to known techniques. The amino acid sequence encoded by the alternatively spliced mRNA can also be predicted from standard codon usage tables. See, e.g., FIG. 9.1 on pg. 214 of Lewin B, *Genes VI*, Oxford University Press, Inc., New York, 1997, the entire disclosure of which is herein incorporated by reference. Peptides based on this sequence can then be generated and used in the practice of the invention.

Nucleic acid sequences from a partially sequenced alternatively spliced mRNA (or nucleic acid sequences derived from a partial amino acid sequence of an alternative splice form) can be used to identify peptides of the invention. For example, a probe or primer can be generated from the partial sequence of an alternatively spliced mRNA or alternative splice form. The probe or primer can be used with known molecular biology techniques such as primer extension, nucleic acid sequencing, or nucleic acid hybridization to obtain additional sequence data with respect to the partially sequenced alternatively spliced mRNA. Peptides of the invention can be synthesized from the additional alternatively spliced mRNA sequences obtained in this manner.

Peptides of the invention must contain at least one amino acid or sequence of amino acids which are not found in the normal protein corresponding to the alternative splice form, or at least one novel juxtaposition of amino acid sequences typically located in different parts of the normal protein. In one embodiment, the peptide of the invention can comprise only amino acid sequences unique to the alternative splice form. Peptides of the invention can be any length, but preferably are between 4 and 50 amino acids in length. Particularly preferred are peptides of the invention which are 7 to 25 amino acids, for example 8 or 9, amino acids in length.

To minimize immunologic cross-reactivity with the corresponding normal protein, it is preferred that the amount of normal amino acid sequence contained in the peptides of the invention is limited. The recognition site for MHC Class I molecules, which are essential for the processing of peptide antigens, is 8 or 9 amino acids in length. Without wishing to be bound by any theory, it is believed that peptides of the invention containing normal amino acid sequences which are 8 or more amino acids in length can generate an unwanted immune response against the normal protein. Therefore, the length of contiguous normal sequence contained within the peptides of the invention is preferably 7 amino acids or less. More preferably, the contiguous normal amino acid sequence is 6, 5, 4, 3, 2 or 1 amino acids in length. It is contemplated that the peptides of the invention can comprise more than one sequence of contiguous normal amino acids.

For peptides of the invention derived from alternative splice forms created by the fusion of ordinarily distant amino acid sequences, it is preferred that the contiguous normal amino acid sequences flanking the splice junction are no more than seven amino acids in length. More preferably, the contiguous normal amino acid sequences flanking the splice junction are each 6, 5, 4, 3, 2 or 1 amino acids in length. In one embodiment, peptides of the invention can comprise contiguous normal amino acid sequences flanking the splice junction of 5 or 6 amino acids in length. Without wishing to be bound by any theory, it is believed that such peptides can produce significantly less cross-reactivity to the corresponding normal protein, while still having an optimal length for MHC class I antigen presentation.

The peptides of the invention can be prepared by any method for synthesizing peptides. For example, the peptides can be obtained by in vitro translation of the corresponding mRNA. The peptides can also be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984); Tam et al., *J. Am. Chem. Soc.* 105:6442, 1983; Merrifield, *Science* 232:341-347, 1986; and Barany and Merrifield, *The Peptides*, Gross & Meienhofer, eds., Academic Press, New York, pp. 1-284 (1979), the entire disclosures of which is incorporated herein by reference.

Alternatively, peptides of the invention can be produced using recombinant DNA technology. For example, nucleic acids encoding the peptides can be synthesized by reverse transcription of the alternatively spliced mRNA, or by chemical synthetic techniques well-known in the art. The nucleic acid coding sequence can then be provided with appropriate linkers and ligated into expression vectors commonly available in the art.

The expression vector can comprise regulatory sequences such as start and stop codons, promoter and terminator regions and an origin of replication. For example, promoter sequences compatible with bacterial hosts can be provided in plasmids containing convenient restriction sites for insertion of the desired coding sequence.

Expression vectors comprising nucleic acids encoding the present immunogenic peptides are preferably transfected into suitable bacterial hosts for expression of the peptides, according to known techniques. Yeast or mammalian cell hosts may also be used, provided the expression vector comprises compatible control sequences. A number of expression vectors and host systems are known in the art, and are commercially available.

Nucleic acids encoding the peptides of the invention can be linked to additional protein coding sequences in an expression vector. Expression of the linked coding sequences produces a fusion protein comprising the peptide of the invention. The additional coding sequences can comprise sequences which encode other peptides of the invention, or sequences which encode other types of proteins.

Other techniques for cloning and expressing nucleic acids are described in, for example, Sambrook et al., *Molecular Cloning, A Laboratory Manual*, Cold Spring Harbor Press, Cold Spring Harbor, N.Y. (1982), and Ausubel et al., (ed.) *Current Protocols in Molecular Biology*, John Wiley and Sons, Inc., New York (1987), and U.S. Pat. Nos. 4,237,224, 4,273,875, 4,431,739, 4,363,877 and 4,428,941, the entire disclosures of which are incorporated herein by reference.

The peptides of the invention can comprise additional amino acids; i.e., amino acids not encoded by the corresponding mRNA. For example, one or more amino acids such as tyrosine, cysteine, lysine, glutamic or aspartic acid can be added to the C- or N-terminus of the peptides. These additional amino acids can be used for: linking two or more peptides of the invention to each other, for coupling one or more peptides of the invention to a polyvalent platform that can enhance presentation of the peptides to the immune system (e.g., polylysine, polyethylene glycol, and the like), for coupling one or more peptides of the invention to a another protein or other molecule; or for modifying the physical or chemical properties of the peptides of the invention. Sites for linking the peptides of the invention to a polyvalent platform or to another protein or other molecule can also be introduced by terminal-$NH_2$ acylation (e.g., acetylation), thioglycolic acid amidation, terminal-carboxy amidation (e.g., with ammonia or methylamine) of the peptides or biotinylation.

Preferably, the peptides of the invention are linked together to form homo- or hetero-multimers. The homo- or hetero-multimers can comprise dimers, trimers, tetramers, pentamers, hexamers or higher multimers. It is understood that formation of the peptides of the invention into multimers should not substantially interfere with ability of the linked peptides to function as desired, e.g., as a cytotoxic T cell determinant or activator of an antibody response.

In a preferred method, homo- or hetero-multimers of the peptides of the invention are formed via cysteine residues which are added to the N- and/or C-terminus of the peptides. The peptides are then formed into multimers via controlled oxidation of the cysteine residues.

In another method, a disulfide/amide forming heterobifunctional agent such as N-succidimidyl-3-(2-pyridyl-dithio) proprionate (SPDP) is used to form multimers with the peptides of the invention. For example, the peptides can be linked via formation of a disulfide linkage between a first SPDP functional group and a cysteine residue in one peptide, and formation of an amide linkage between a second SPDP functional group and free amino group in another peptide. Other suitable disulfide/amide forming heterobifunctional agents are known; see, for example, *Immun. Rev.* 62:185, 1982, the entire disclosure of which is herein incorporated by reference.

Multimers can also be formed from the peptides of the invention using bifunctional coupling agents that form a thioether linkage. Suitable thioether forming agents are commercially available, and include reactive esters of 6-maleimidocaproic acid; 2 bromoacetic acid; 2-iodoacetic acid; and 4-(N-maleimido-methyl)cyclohexane-1-carboxylic acid. To effect coupling of the peptides, the carboxyl groups of the thioether forming agents are activated with succinimide or the sodium salt of 1-hydroxy-2-nitro-4-sulfonic acid. A preferred activated thioether coupling agent is succinimidyl 4-(N-maleimidomethyl)cyclohexane-1-carboxylate (SMCC).

It is understood that monomeric or multimeric peptides of the invention can also be linked to other proteins using the techniques and reagents described above.

The peptides of the invention can also be modified as necessary to provide certain desired attributes such as improved pharmacological or immunologic effects, or to facilitate entry of the peptides into cells.

Modifications which can improve immunologic effects of the peptides of the invention include modifications which enhance the CTL or antibody-inducing activity. For example, the hydrophobicity of the peptide N-terminus can be increased, particularly where the second residue of the N-terminal is already hydrophobic and is implicated in binding to an HLA restriction molecule. Without being bound by any theory, it is believed that increasing the hydrophobicity of the N-terminus of the peptides of the invention enhances the efficiency of presentation to T cells. Thus, the peptides of the invention that contain epitopes for which a host may not generate significant CTL activity can be made CTL-inducing by substituting hydrophobic residues at the N-terminus of the peptide.

Other modifications which improve the immunologic effects of the peptides of the invention include amino acid insertions, deletions, and substitutions (either conservative or non-conservative) which increase the binding affinity of the immunogenic peptide to an MHC molecule for subsequent presentation to a cytotoxic T-lymphocyte. By "conservative substitutions" is meant replacing an amino acid residue with another that is biologically and/or chemically similar; e.g., one hydrophobic residue for another, or one polar residue for another. Combinations of amino acids which are biologically or chemically similar include Gly/Ala; Val/Ile/Leu; Asp/Glu; Asn/Gln; Ser/Thr; Lys/Arg; and Phe/Tyr.

Factors which influence the number and type of amino acid residues that can be substituted or deleted include the spacing between essential epitopic points on the immunogenic peptide, and certain conformational and functional attributes that may be sought (e.g., hydrophobicity vs. hydrophilicity). Replacing one amino acid with another in a given combination would therefore be a conservative substitution. Other conservative substitutions will be apparent to those of ordinary skill in the art.

In addition, the contributions made by the side chains of amino acid residues in the peptides of the invention can be probed via systematic replacement of amino acid residues in the peptide with a specified amino acid (e.g., Ala).

The peptides of the invention can also be modified to increase stability of the peptides, either in vitro or in vivo. Such modifications include synthesizing the peptides to contain at least one D-amino acid. The D-amino acid containing peptides are more resistant to peptidases and are more stable in serum and tissues compared to their L-peptide counterparts. It is expected that peptides of the invention synthesized as D-amino acid containing peptides will have the same efficacy as the corresponding L-peptide. However, any loss of binding affinity for an MHC molecule would be compensated for by increased in vivo stability of the D-amino acid peptide. Stability of an L-amino acid-containing peptide of the invention can also be increased by "capping" the peptide with a D-amino acid, which inhibits exopeptidase destruction of the peptide. D-amino acid containing peptides can also be synthesized as "inverso" or "retro-inverso" forms; that is, by replacing all L-amino acids of a sequence with D-amino acids, or by reversing the sequence of the amino acids and replacing all the L-amino acids with D-amino acids.

Modifications of the peptides of the invention which do not affect the ability of the peptides of the invention to elicit an immune response are also contemplated. For example, amino acid residues which are not required for retention of immunogenic activity can be substituted or deleted. One of ordinary skill in the art can readily determine which amino acids can be substituted or deleted, for example by mutational analysis techniques well-known in the art. Generally, any substitutions, additions or deletions between epitopic and/or conformationally important residues will employ amino acids or moieties chosen to avoid stearic and charge interference that might disrupt binding of the peptide to an MHC molecule. Other types of modifications which do not affect the ability of the peptides of the invention to elicit an immune response are discussed supra under the definition of "protein" or "peptide."

One or more peptides of the invention can be administered to a subject to stimulate an immunologic response against the alternative splice form from which the peptides were derived. The immunologic response stimulated by the peptides includes a cytotoxic T lymphocyte and/or an antibody response. For example, administration of the peptides of the invention can generate an MHC HLA-class I restricted cytotoxic T lymphocyte response, which includes a CD8$^+$ T lymphocyte response specific for a target antigen, wherein CD8$^+$, MHC class I-restricted T lymphocytes are activated. Administration of the peptides of the invention can also generate an MHC HLA-class II restricted cytotoxic T lymphocyte response, which includes a CD4$^+$ T lymphocyte response specific for a target antigen, wherein CD4$^+$, MHC class II-restricted T lymphocytes are activated.

As used herein, "subject" includes an animal, preferably a mammal, more preferably a human being, that has or is at risk for having a disease or condition in which diseased or abnormal cells produce the alternative splice form from which immunogenic peptide is derived. The alternative splice form from which the peptide of the invention is derived is substantially absent from normal cells in the subject. Generation of an immunologic response in the host with the peptides results in the prophylactic or therapeutic treatment of the disease or condition associated with the expression of the alternative splice form.

Preferably, two or more of the peptides of the invention are administered to the subject. For example, two or more peptides can be used which define different epitopes from one or more alternative splice forms. The two or more peptides can be linked to form multimers by the techniques described above, or can be formulated in a composition without forming multimers; e.g., as an admixture. Admixtures of different multimers, or admixtures of multimers and monomeric peptides, are also part of the invention. It is contemplated that admixtures can comprise 1, 2, 3, 4 or 5 or more different monomeric or multimeric peptides of the invention.

When one type of peptide of the invention is administered as a homomultimer, a plurality of repeating epitopes are presented to the subject's immune system. If two or more different peptides of the invention are administered, either as a heteromultimer or an admixture of peptides, a plurality of heterogeneous epitopes are presented to the subject's immune system. The presentation of a plurality of homo- or heterogeneous epitopes produces a synergistic effect on the subject's immune system. Thus, the immune response which is generated by administering the peptides of the invention as multimers or admixtures is greater than the expected additive effects of each peptide comprising the multimer or admixture.

The peptides of the invention can also be administered to a subject in combination with other peptides that present "T-helper" cell epitopes; i.e., epitopes that stimulate T cells which cooperate in the induction of cytotoxic T cells against the target antigen. Peptides that present "T-helper" cell epitopes are described in Ferrari et al., *J. Clin. Invest.* 88:214-222, 1991, and U.S. Pat. No. 4,882,145, the entire disclosures of which are herein incorporated by reference.

As used herein, a substance which is administered "in combination with" a peptide of the invention can be administered at the same time and in the same site as the peptide (i.e., as a complex or as an admixture), or can be administered at a different time and/or place as the peptide. For example, the substance can be administered in the same site before or after administration of a peptide of the invention, or can be administered simultaneously with a peptide of the invention but in a distant site (e.g., the substance can be administered orally if the peptide is administered parenterally, and vice versa; or the substance can be administered in a contralateral limb if both peptide and the substance are administered parenterally). As used herein, a substance which is "complexed" with a of the invention peptide can be covalently or noncovalently attached to the peptide.

The peptides of the invention can also be administered to a subject in combination with at least one component that primes CTLs. For example, certain lipids are known to prime CTLs in vivo against viral antigens. Lipids suitable for priming CTLs include tripalmitoyl-S-glycerylcysteinly-serylserine (P$_3$CSS), which can effectively prime virus-specific cytotoxic T lymphocytes when covalently attached to a peptide. See Deres et al., *Nature* 342:561-564, 1989, the entire disclosure of which is herein incorporated by reference. In a preferred embodiment, peptides of the invention are complexed to P$_3$CSS and the resulting lipopeptide is administered to an subject to specifically prime a cytotoxic T lymphocyte response.

The induction of neutralizing antibodies can also be primed with P$_3$CSS conjugated to a peptide. Thus, peptides of the invention coupled to P$_3$CSS can also elicit a humoral immune response.

In the practice of the invention, at least one peptide of the invention is administered to a patient in an amount sufficient to elicit an immune response; i.e., an antibody or cytotoxic T lymphocyte response, to the diseased or abnormal cells (the "effective amount"). Where peptides of the invention are administered as a multimer or as an admixture, the effective amount represents the cumulative total of the administered peptides. The presence of an immune response in the subject can be determined, for example, by measuring antigen-specific CTL activity in peripheral blood lymphocytes (PBLs) obtained from the subject during treatment. Alternatively, the presence of an immune response in the subject can be determined by measuring the titer of antibodies specific to the peptides of the invention, or by intradermal injection of the peptides of the invention with subsequent measurement of a delayed-type hypersensitivity (DTH) response.

The effective amount of the peptides of the invention administered to a given subject will depend on factors such as the peptide composition, the manner of administration, the stage and severity of the disease being treated, the weight and general state of health of the subject, and the judgment of the prescribing physician. Generally, an effective amount of the peptides of the invention administered to a 70 kg subject is from about 1 microgram to about 2,000 mg of peptide, preferably about 1 microgram to about 500 mg of peptide, more preferably about 10 micrograms to about 200 mg of peptide, and particularly preferably about 50 micrograms to about 100 mg peptide. An optimal dose is about 500 micrograms of peptide/70 kg subject.

It is understood that the peptides of the invention are often employed in serious disease states; that is, situations where the subject's life is threatened. In such cases, particularly in view of the relatively nontoxic nature of the immunogenic peptides, it is possible to administer substantial excesses of the peptides to the subject; i.e., effective amounts in excess of 2000 mg/70 kg subject.

Single or multiple administrations of an effective amount of the peptides of the invention can be performed with dose levels and patterns selected by the treating physician. For therapeutic use, an initial dose of the peptides is preferably administered to a subject at the first appearance of clinical symptoms, or shortly after diagnosis of the disease or condition, with "booster doses" administered until at least a partial abatement of symptoms is observed. A preferred dosage regimen for therapeutic treatment comprises administering to a subject an initial dose of from about 10 micrograms to about 100 mg of at least one peptide of the invention, followed by booster dosages every 2-4 weeks of from about 1 microgram to about 1 mg of at least one peptides of the invention for a period of 6 weeks to 3 months, depending on the strength of the subject's immune response or degree of response to the treatment. Other therapeutic dosage regimens are contemplated.

For prophylactic use, an effective amount of at least one peptide of the invention is preferably administered in uniform doses at regular intervals over a period of weeks or months. A preferred dosage regimen for prophylactic use is administration of about 10 micrograms to about 100 mg of at least one peptide of the invention every 2-4 weeks for 6 to 8 months. Other prophylactic dosage regimens are contemplated.

For therapeutic or prophylactic use, the peptides of the invention can be administered by any route which is sufficient to expose the peptides to the subject's immune system. Routes of administration include enteral (e.g., oral, rectal, intranasal, etc.) and parenteral administration. Parenteral administration includes intravenous, intramuscular, intraarterial, intraperitoneal, intravaginal, intravesical (e.g., into the bladder), intradermal, intrapulmonary, inhalation, topical or subcutaneous administration. Also contemplated within the scope of the invention is the instillation of the peptides into the body of the subject in a controlled formulation, with systemic or local release of the peptides to occur at a later time. Preferred routes of administration are via intramuscular, intranasal, intradermal and subcutaneous delivery.

For therapeutic or prophylactic treatment, at least one peptide of the invention can also be administered to a subject via expression of nucleic acid sequences encoding the peptide in cells of the subject. For example, cells of a subject can be infected with an attenuated viral host engineered to express at least one nucleic acid encoding a peptide of the invention. A preferred attenuated viral host is vaccinia virus. In the practice of the invention, an attenuated viral host comprising nucleic acid sequences encoding one or more of the peptides of the invention is introduced into a subject such that some of the subject's cells are infected with the viral host. The infected cells, under control of the viral host, express the peptides of the invention and elicit an immune response in the subject; i.e., a cytotoxic T lymphocyte or antibody response. Vaccinia viral vectors useful as attenuated viral hosts, and methods for delivering the vectors to a subject are known in the art, for example as described in U.S. Pat. No. 4,722,848, the entire disclosure of which is herein incorporated by reference.

For therapeutic or prophylactic treatment, the peptides of the invention can also be administered to a subject via expression of nucleic acid sequences encoding the peptide in bacterial hosts. In the practice of the invention, a bacterial host comprising one or more nucleic acid sequences encoding a peptide of the invention are introduced into a subject, for example by intradermal or intravesical instillation. The bacterial host expresses the peptides of the invention, and elicits an immune response in the subject; i.e., a cytotoxic T lymphocyte or antibody response. A preferred bacterial host is *bacillus* Calmette Guerin (BCG), which is described in Stover et al. (Nature 351:456-460, 1991), the entire disclosure of which is herein incorporated by reference. Other bacterial hosts suitable for use in the practice of the invention, such as *Salmonella typhi, Listeria monocytogenes* and the like, are known to those skilled in the art.

For therapeutic or prophylactic treatment, the peptides of the invention can also be administered to a subject via expression of nucleic acid sequences encoding the peptide in yeast hosts. In the practice of the invention, a yeast host comprising one or more nucleic acid sequences encoding a peptide of the invention are introduced into a subject, for example orally, or by intradermal or intravesical instillation. The yeast host expresses the peptides of the invention, and elicits an immune response in the subject; i.e., a cytotoxic T lymphocyte or antibody response. Preferred yeast hosts are *Saccharomyces cerevisiae* or *Schizosaccharomyces pombe*.

The peptides of the invention can be administered to a subject in combination with any known carrier or adjuvant. Suitable carriers include keyhole limpet hemocyanin; thyroglobulin; albumins such as human serum albumin; tetanus toxoid; polyamino acids such as poly(D-lysine:D-glutamic acid), and the like. Suitable adjuvants include complete or incomplete Freund's adjuvant, aluminum phosphate, aluminum hydroxide, polylecithins, emulsified oils and alum.

The peptides of the invention can also be administered to a subject in combination with immunostimulatory compounds. For example, the immunogenic peptides can be administered with granulocyte macrophage colony stimulating factor (GM-CSF), which is a cytokine known to enhance the presentation of peptides to dendritic cells for processing and presentation to the immune system. Other suitable immunostimulatory molecules include other cytokines such as IL-12, IL-2, IL-4, IL-5, IL-1alpha, and IL-18; and haptens such as dinitrophenol.

The peptides of the invention can also be administered to a subject by exposing immune system effector cells from a subject to one or more of the peptides ex vivo. As used herein, "immune system effector cells" are cells which either prime the immune system to target other cells for elimination, or which effect elimination of targeted cells (i.e., "killer" cells). Immune system effector cells include dendritic cells, lymphokine-activated killer (LAK) cells, natural killer (NK) cells, T-cells and macrophages. Methods of obtaining immune system effector cells, and methods for ex vivo treatment of such cells are known in the art, for example as described in Blaese et al., 1995, *Science* 270:475-80; Kohn et al., 1995, *Nature Medicine* 1(10):1017-23; and Ferrari et al., 1992, *Blood* 80:1120-24, the entire disclosures of which are herein incorporated by reference.

For example, immune system cells, or mixtures thereof, can be removed from a subject and maintained in culture. The immune system effector cells can optionally be enriched for a particular cell type, either in culture or upon removal from the subject. The cultured immune system cells are then treated with the immunogenic peptides. Treatment of the cells with peptides of the invention includes direct exposure of the cells to the peptides, or introduction of a nucleic acid encoding the peptides into the cells. For cells directly exposed to the peptides of the invention, concentrations far in excess of what could be tolerated by a subject if administered in vivo can be used. For example, cells can be treated with a 10 micromolar solution of the peptides of the invention, or can be treated with peptides of the invention in a final concentration of about 5 mg/ml to about 10 mg/ml, preferably about 0.1 ng/ml to about 5 mg/ml.

Immune system effector cells are generally capable of internalizing the peptides of the invention upon direct exposure to the peptides in culture. However, the peptides of the invention can be modified so that entry into the immune system effector cells is enhanced. For example, the peptides can be encapsulated in a liposome prior to being administered, as is described in more detail below. The encapsulated peptides are delivered directly into the cells by fusion of the liposome to the cell membrane. Reagents and techniques for encapsulating the peptides of the invention in liposomes are well-known in the art, and include, for example, the ProVectin™ Protein Delivery Reagent from Imgenex.

The peptides of the invention can also be modified to enhance entry into the cells by complexing the peptides with a peptide leader sequence known as a "protein transduction domain" or "PTD." PTDs direct entry of the compound into cells by a process known as "protein transduction." See Schwarze et al. (1999), *Science* 285: 1569-1572. PTDs are well-known in the art, and may comprise any of the known PTD sequences including, for example, arginine-rich sequences such as a peptide of nine to eleven arginine residues optionally in combination with one to two lysines or glutamines as described in Guis et al. (1999), *Cancer Res.* 59: 2577-2580, the entire disclosure of which is herein incorporated by reference. Preferred PTDs are sequences of eleven arginine residues or the $NH_2$-terminal 11-amino acid protein transduction domain from the human immunodeficiency virus TAT protein (SEQ ID NO: 42). Other suitable PTD sequences include other arginine-rich sequences; e.g., 9 or 10 arginines, or six or more arginines in combination with one or more lysines or glutamines. Such leader sequences are known in the art; see, e.g., Guis et al. (1999), supra. A PTD may be located anywhere on the peptides of the invention that does not disrupt the peptides' ability to elicit an immune response, but is preferably located at the C-terminal end.

Kits and methods for constructing fusion proteins comprising a peptide of the invention and a PTD are known in the art; for example the TransVector™ system (Q-BIOgene), which employs a 16 amino acid peptide called "Penetratin™" corresponding to the *Drosophila* antennapedia DNA-binding domain; and the Voyager system (Invitrogen Life Technologies), which uses the 38 kDa VP22 protein from Herpes Simplex Virus-1.

The peptides of the invention can also be modified to enhance entry into cells by complexing the peptides with heat shock proteins (HSP), for example as described in U.S. Pat. No. 5,935,576 of Srivastava (peptide non-covalently linked to HSP), or Suzue K et al. (1997), *Proc. Natl. Acad. Sci. USA,* 94:13146-13151 (peptide covalently linked to HSP), the entire disclosures of which are herein incorporated by reference. Fusion proteins comprising HSP sequences and a peptide of the invention can also be generated according to standard techniques.

A nucleic acid encoding a peptide of the invention can be introduced into the immune system effector cells by any known method, for example by transfecting the cells with expression vectors or infecting the cells with an attenuated viral host as described above. Techniques for constructing expression vectors comprising nucleic acid sequences encoding peptides of the invention are discussed above.

After treatment with at least one peptide of the invention, a portion of the ex-vivo treated immune system effector cells can be examined to confirm the presence of appropriate levels of the peptide(s) within the cell, and the remaining treated cells can be reintroduced into the subject. Treated cells may be reintroduced into the subject by parenteral methods, including intravenous infusion and direct injection into the bone marrow. Treated cells are preferably reintroduced into the subject in a saline solution or other pharmaceutically acceptable carrier. The number of treated cells to be reintroduced depends on the purity of the cell population, but a typical dosage is in the range of about $10^5$ to about $10^8$ cells per kilogram of subject body weight. The number of cells available for re-introduction can be increased by expanding the cells in culture prior to treatment with the peptides of the invention.

The invention also provides a method for identifying peptides of the invention which induce MHC-restricted cytotoxic T lymphocyte responses. For example, peripheral blood lymphocytes (PBLs) can be obtained and exposed to one or more peptides of the invention. The ability of the peptides to induce specific cytotoxic activity is determined by incubating the stimulated PBL with autologous labeled (e.g., $^{51}Cr$) target cells (such as HLA matched macrophages, T cells, fibroblasts or B lymphoblastoid cells) that endogenously synthesize the targeted antigen (or, alternatively, the cell is pulsed with the peptide of interest), and measuring specific release of label. Preferably, the PBLs are exposed to pools of peptides of the invention, wherein each peptide is about 8 to 20 amino acids long, preferably 9 to 12 amino acids long. Peptides of the invention which induce cytotoxic T lymphocyte activity can be selected from the pools.

Once an peptide of the invention that stimulates a cytotoxic T lymphocyte response is identified, the MHC restriction element of the response can be determined. This involves incubating the stimulated PBL (or short term cultures thereof) with a panel of labeled target cells of known HLA types that have been pulsed with the peptide of interest or the appropriate controls. The HLA allele(s) of cells that are lysed by the stimulated PBL are compared to cells not lysed. The HLA alleles from the lysed target cells represent the MHC restriction element(s) for the cytotoxic T lymphocyte response to the peptide.

The lysis of target cells by stimulated PBLs can be detected either by measuring the release of label from autologously labeled target cells, or with an enzyme-linked immunospot ("ELISPOT") assay. The ELISPOT method is well-known in the art, and kits and reagents for performing the method are commercially available from BD Biosciences Pharmingen, San Jose, Calif., 95131-1807. An ELISPOT assay can detect cytokine release from a PBL at the single cell level, allowing the direct determination of cytokine-producing cell frequencies.

Briefly, the ELISPOT method is performed by coating a cell culture dish or well with a cytokine capture antibody, for example an anti-interferon gamma antibody. The unoccupied spots on the culture dish or well are then blocked with a non-specific binding protein. Target cells, for example tumor cells, that endogenously synthesize the alternative splice form which has been used to stimulate PBLs are added to the culture dish or well. Alternatively, target cells can be pulsed with the peptide of interest. Activated PBLs are then added to the culture dish or well. If the activated PBLs specifically lyse the target cells, the PBLs secrete cytokines such as interferon-gamma, which is captured by the cytokine capture antibody initially coated onto the culture dish or well. A secondary antibody that recognized a different epitope of interferon gamma is then used to detect the presence of any interferon-gamma secreted by the PBLs and captured by the cytokine capture antibody. The secondary antibody can be conjugated with a detectable label, such as fluorescent or radioactive label. Identification of peptides of the invention which induce MHC-restricted cytotoxic T lymphocyte responses by the ELISPOT method is shown in Example 5 below.

The peptides of the invention can be formulated into pharmaceutical compositions, also called vaccine compositions, according to techniques known in the art. Pharmaceutical compositions of the present invention are characterized as being at least sterile and pyrogen-free. As used herein, "pharmaceutical formulations" include formulations for human and veterinary use. The present pharmaceutical formulations may comprise at least one peptide of the invention mixed with a physiologically acceptable carrier medium to form solutions, suspensions or dispersions. Preferred physiologically acceptable carrier media are water, buffered water, normal saline, 0.4% saline, 0.3% glycine, hyaluronic acid and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions (e.g., 0.01 to 10 mole percent) of chelants (such as, for example, DTPA or DTPA-bisamide) or calcium chelate complexes (as for example calcium DTPA, CaNaDTPA-bisamide), or, optionally, additions (e.g., 1 to 50 mole percent) of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

Methods for preparing pharmaceutical compounds of the invention are known to those of ordinary skill in the art, for example as described in *Remington's Pharmaceutical Science*, 17th ed., Mack Publishing Company, Easton, Pa. (1985), the entire disclosure of which is herein incorporated by reference.

For example, a solid pharmaceutical composition for oral administration can comprise any of the carriers and excipients listed above and 10-95%, preferably 25%-75%, of one or more peptides of the invention. A pharmaceutical composition for aerosol administration can comprise 0.01-20% by weight, preferably 1%-10% by weight, of one or more peptides of the invention in finely divided form along with a surfactant and propellant. Suitable surfactants include esters or partial esters of fatty acids containing from 6 to 22 carbon atoms (e.g., caproic, octanoic, lauric, palmitic, stearic, linoleic, linolenic, olesteric or oleic acid with an aliphatic polyhydric alcohol, or its cyclic anhydride); and mixed esters such as mixed or natural glycerides. The surfactant can comprise 0.1%-20% by weight, preferably 0.25-5% by weight, of the aerosol pharmaceutical composition, with the balance being propellant. A carrier may also be included as desired; e.g., lecithin for intranasal delivery.

The peptides of the invention or pharmaceutical compositions of the invention can be encapsulated in liposomes. Liposomes aid in the delivery of the immunogenic peptides to a particular tissue, such as lymphoid tissue, and can also increase the blood half-life of the peptides or compositions. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al., *Ann. Rev. Biophys. Bioeng.* 9:467, 1980; U.S. Pat. Nos. 4,235,871, 4,501,728, 4,837,028, and 5,019,369, the entire disclosures of which are herein incorporated by reference. Preferably, peptides of the invention are incorporated as part of a liposome, either alone or in conjunction with a ligand molecule that can target the liposome to a particular cell or tissue. Ligands which bind to receptors prevalent in lymphoid cells, such as monoclonal antibodies that bind to the CD45 antigen, are preferred.

The present invention also provides antibodies against alternative splice forms or peptides of the invention. An antibody of the invention specifically binds an epitope of the alternative splice form or peptide of the invention that is not present in the normal protein. The antibody can be a monoclonal antibody, a polyclonal antibody or an antibody fragment that is capable of binding antigen. The antibodies of the invention include chimeric, single chain, and humanized antibodies, as well as Fab fragments and the products of an Fab expression library. Antibody fragments, such as Fab antibody fragments, which retain some ability to selectively bind to the antigen of the antibody from which they are derived, can be made using well known methods in the art. Such methods are generally described in U.S. Pat. No. 5,876,997, the entire disclosure of which is incorporated herein by reference.

Polyclonal antibodies of the invention can be produced by immunizing a host with substantially pure alternative splice form or peptide of the invention, using techniques well-known in the art. The antibody titer in the immunized host can be monitored over time by standard techniques, such as with an enzyme linked immunosorbent assay (ELISA) using immobilized peptide. If desired, the antibody molecules can be harvested or isolated from the host (e.g., from the blood or serum) and further purified by known techniques, such as protein A chromatography to obtain the IgG fraction.

At an appropriate time after immunization, e.g., when the specific antibody titers are highest, antibody-producing cells can be obtained from the host and used to prepare monoclonal antibodies by standard techniques, such as the hybridoma techniques described by Kohler and Milstein (1975) *Nature* 256:495-497 and by Mishell, B. B. et al., *Selected Methods In Cellular Immunology*, (Freeman W H, ed.) San Francisco, 1980; the human B cell hybridoma technique (Kozbor et al. (1983) *Immunol. Today* 4:72); the EBV-hybridoma technique (Cole et al. (1985), *Monoclonal Antibodies and Cancer Therapy*, Alan R. Liss, Inc., pp. 77-96); or trioma techniques. See also *Current Protocols in Immunology* (1994) Coligan et al. (eds.) John Wiley & Sons, Inc., New York, N.Y.). The disclosures of all citations in this paragraph are herein incorporated by reference in their entirety.

Hybridoma cells producing a monoclonal antibody of the invention can be detected by screening the hybridoma culture supernatants for antibodies that bind the polypeptide of interest, e.g., using a standard ELISA assay. Alternatively, a monoclonal antibody directed against an alternative splice form or peptide of the invention can be identified and isolated by screening a recombinant combinatorial immunoglobulin library (e.g., an antibody phage display library) with the peptide of interest. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, methods and reagents suitable for generating and screening an antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734, the entire disclosures of which are herein incorporated by reference.

Recombinant antibodies, such as chimeric and/or humanized monoclonal antibodies, are within the scope of the invention. Such chimeric and humanized (including chimeric humanized) monoclonal antibodies can be produced by recombinant DNA techniques known in the art, for example using methods described in U.S. Pat. No. 5,225,539; PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison (1985) *Science* 229:1202-1207; Oi et al. (1986) *Bio/Techniques* 4:214; Jones et al. (1986) *Nature* 321:552-525; Verhoeyan et al. (1988) *Science* 239:1534; and Beidler et al. (1988) *J. Immunol.* 141:4053-4060, the entire disclosures of which are herein incorporated by reference.

The present antibodies can be used to isolate peptides of the invention, or the alternative splice forms from which they are derived, using standard techniques such as affinity chromatography or immunoprecipitation. Moreover, the present antibodies can be used to detect alternative splice forms (e.g., in a cellular lysate or cell supernatant) in order to evaluate the abundance and pattern of expression of an alternative splice form.

The present antibodies can also be used diagnostically to monitor protein levels in tissue as part of a clinical testing procedure, for example to determine the efficacy of a given treatment regimen. Detection of protein levels with the present antibodies can be facilitated by coupling the antibody to a detectable substance. Suitable detectable substances include various enzymes (e.g., horseradish peroxidase; alkaline phosphatase; beta-galactosidase; and acetylcholinesterase) prosthetic group complexes (e.g., streptavidin/biotin and avidin/biotin), fluorescent materials (e.g., umbelliferone; fluorescein; fluorescein isothiocyanate; rhodamine; dichlorofriazinylamine fluorescein; dansyl chloride; and phycoerythrin, luminescent materials (e.g., luminol), bioluminescent materials (e.g., luciferase, luciferin, and aequorin), and radioactive materials (e.g., $^{125}I$, $^{131}I$, $^{35}S$ or $^{3}H$).

Antibodies of the invention can also be used in the therapeutic or prophylactic treatment of subjects having a disease or condition in which diseased or abnormal cells produce an alternative splice form having epitopes to which the antibody can bind. The alternative splice form is substantially absent from normal cells in the subject. In the practice of the invention, an effective amount of at least one antibody of the invention is administered to a subject. Preferably, at least one monoclonal antibody specific for an alternative splice form or peptide of the invention are administered to the subject.

An "effective amount" of the present antibodies is the amount which ameliorates one or more clinical symptoms in a subject, or causes a reduction in the number of diseased or abnormal cells in a subject. Amelioration of clinical symptoms would be readily apparent to the ordinarily skilled physician. The number of diseased or abnormal cells in a subject's body can also be readily determined. Suitable techniques for determining the number of diseased or abnormal cells includes direct measurement (e.g., calculating the concentration of leukemic cells in the blood or bone marrow) or by estimation from the size of a tissue mass. As used herein, a "tissue mass" is any localized collection of diseased or abnormal cells in a subject's body, for example a tumor. The size of a tissue mass can be ascertained by direct visual observation or by diagnostic imaging methods such as X-ray, magnetic resonance imaging, ultrasound, and scintigriphy. Diagnostic imaging methods used to ascertain size of a tissue mass can be employed with or without contrast agents, as is known in the art. The size of a tissue mass can also be ascertained by physical means, such as palpation of the tissue mass or measurement of the tissue mass with a measuring instrument such as a caliper. An effective amount of the present antibodies can be, for example, from about 0.1 mg/kg to about 100 mg/kg of body weight, preferably about 50 mg/kg to about 100 mg/kg of body weight, more preferably about 10 mg/kg to about 20 mg/kg of body weight.

The antibodies of the invention are preferably administered to a subject by parenteral means, for example by intravascular (e.g., intraarterial or intravenous) injection or infusion.

The following examples are offered by way of illustration, not by way of limitation.

EXAMPLE 1

Identification of VEGF Immunogenic Peptides

Alternative splice forms of vascular endothelial growth factor (VEGF) proteins were identified in HC2 20d2/c cells, which are NIH-3T3 cells that have been transfected with a constitutively active form of the EGF receptor, EGFRvIII. HC2 20d2/c cells were cultured according to standard techniques. Total RNA from HC2 20d2/c cells was isolated, followed by isolation of poly A+ RNA. The poly A+ RNA was used as a template for first strand cDNA synthesis using oligo dT primers. PCR was then performed with primers from VEGF isoforms. The sequences of the primers used for the PCR are provided below. The primers are represented in the 5' to 3' direction, with nucleotide numbers corresponding to the normal cDNA sequence listed to the left of each primer, where available.

Mouse VEGF

```
Set 1
79-99      CCG AAA CCA TGA ACT TTC TGC (SEQ ID NO: 43)
936-916    CTT GGC GAT TTA GCA GCA GAT (SEQ ID NO: 44)

Set 2
117-137    ACC CTG GCT TTA CTG CTG TAC (SEQ ID NO: 45)
909-888    AAA TGG CGA ATC CAG TCC CAC (SEQ ID NO: 46)

Set 3
126-146    TTA CTG CTG TAC CTC CAC CAT (SEQ ID NO: 47)
815-795    GAA GGA TCT CCT CTT CCT TCA (SEQ ID NO: 48)
```

Murine VEGFB:

```
Set 1
119-139    CTG CTT GTT GCA CTG CTG CAG (SEQ ID NO: 49)
778-758    TCT GGA AAG CAG CTT GTC ACT (SEQ ID NO: 50)

Set 2
155-175    GCC CCT GTG TCC CAG TTT GAT (SEQ ID NO: 51)
739-719    TAC AGG TGA CTG GGT TGA GCT (SEQ ID NO: 52)

Set 3
182-202    AGC CAC CAG AAG AAA GTG GTG (SEQ ID NO: 53)
733-713    TGT CTG GGT TGA GCT CTA AGC (SEQ ID NO: 54)
```

Murine VEGFC:

```
Set 1
151-171    AAC ATG CAC TTG CTG TGC TTC (SEQ ID NO: 55)
1559-1539  CTC TCC CGC AGT AAT CCA CAT (SEQ ID NO: 56)

Set 2
292-312    GAG GTC AAG GCT TTT GAA GGC (SEQ ID NO: 57)
1521-1501  CTT GGG CCT CTG TTA CCA TGT (SEQ ID NO: 58)

Set 3
301-321    GCT TTT GAA GGC AAA GAC CTG (SEQ ID NO: 59)
1509-1489  TTA CCA TGT GGT CCC ACA GAG (SEQ ID NO: 60)
```

Murine VEGFD:

```
Set 1
15-35      GGA GAA TGC CTT TTG CAA CAC (SEQ ID NO: 61)
1343-1323  GCC ATT GCA TGG AAA TGT GGC (SEQ ID NO: 62)

Set 2
57-77      CAA CTG CTT AGT CAT CGG TAG (SEQ ID NO: 63)
1234-1214  ACT TGA CAA AGC AGT GAG CTG (SEQ ID NO: 64)

Set 3
96-116     ATG TAT GGA GAA TGG GGA ATG (SEQ ID NO: 65)
1178-1158  GTT GAA TCA AGG GTT CTC CTG (SEQ ID NO: 66)
```

Murine PlGF:

```
Set 1
           TCT CCT CTG GTA TCA GCG TCT (SEQ ID NO: 67)
           GCA CTG AAT TCC TGA GTG TCT (SEQ ID NO: 68)

Set 2
           TGG TGA TTG TGC CTT GAA GGA (SEQ ID NO: 69)
763-743    TCC ATG CCC CTT ATC ATG GAG (SEQ ID NO: 70)

Set 3
88-108     TGA AGG ACC TTG GCT CTG GAT (SEQ ID NO: 71)
           AAT AGA GGG TAG GTA CCA GCA (SEQ ID NO: 72)
```

PCR was performed with each primer set 1. If a distinct band was visible after this round of PCR, then the band was excised and the PCR product was sequenced using the 5' primer. If the band was not distinct, it was excised, the PCR products was purified, and 10% of the purified PCR product was used for further amplification using primer set 2.

Alternatively, if there were multiple indistinct bands, then the PCR products from the reaction tube were purified using a commercially available kit (Qiagen), and 10% of the purified product was used for another round of PCR using primer set 2. If a band was still indistinct it was excised, the PCR product was purified, and 10% of the purified product was is used for further amplification using primer set 3. The distinct bands from the $2^{nd}$ or $3^{rd}$ amplification rounds are sequenced using the appropriate 5' primer. Sequences were compared to the known gene sequence to identify alternative splice forms.

One alternative splice form was identified in VEGF and VEGFB, and two were found in VEGFD (see FIG. 1 for identification of VEGFD#1; SEQ ID NO: 77 below). Amino acid translation of these sequences provided four VEGF peptides which contain amino acid sequences unique to the VEGF alternative splice forms (hereinafter "VEGF peptides"). The partial coding sequences of the alternatively spliced VEGF mRNAs, and the VEGF peptides encoded by the mRNA partial sequences, are provided below.

VEGF Alt. Splice #1

```
                                               (SEQ ID NO: 73)
R   T   K   P   E   K   C   D   K   P   R   R
                                               (SEQ ID NO: 74)
AGA ACA AAG CCA GAA AA^A TGT GAC AAG CCA AGG CGG
               505^637
```

SEQ ID NO: 73 represents the peptide encoded by an alternatively spliced mRNA (SEQ ID NO: 74) spliced to create a junction of nucleotides 505 and 637, bringing together two normally distant sequences. The reading frame of mRNA is preserved, and a new codon is also formed at the splice junction (AAA encoding for a lysine residue).

VEGFB Alt. Splice #1

```
                                               (SEQ ID NO: 75)
V   V   K   Q   L   V   Q   T   P   P   L   P   P
                                               (SEQ ID NO: 76)
GTG GTC AAA CAA CTA GT^G CAG ACG CCG CCG CTT CCT CCA
                  300^678
```

SEQ ID NO: 75 represents the peptide encoded by an alternatively spliced mRNA (SEQ ID NO: 76), spliced to create a junction of nucleotides 300 and 678. The splice junction recreates the native valine at this position, but the subsequent codons are out of frame with the native reading frame of normal VEGFB, so that novel amino acids are produced from nucleotide 679 onward.

VEGFD Alt. Splice #1

```
                                          (SEQ ID NO: 77)
H   G   P   V   K   M   S   S   F   Q   E   T
                                          (SEQ ID NO: 78)
CAT GGA CCA GTG AAG^ATG TCC TCA TTC CAA GAA ACT
                185^752
```

SEQ ID NO: 77 represents the peptide encoded by an alternatively spliced mRNA (SEQ ID NO: 78), spliced to create a junction of nucleotides 185 and 752. The splice junction shifts the codons out of frame at nucleotide 752 relative to the native reading frame of VEGFD, so that novel amino acids are produced from this point onward.

VEGFD Alt. Splice #2

```
                                          (SEQ ID NO: 79)
L   E   R   S   E   S   C   E   D   R   C   P
                                          (SEQ ID NO: 80)
TTG GAA CGA TCT GAA^AGC TGT GAG GAC AGA TGT CCT
                238^1047
```

SEQ ID NO: 79 represents the peptide encoded by an alternatively spliced mRNA (SEQ ID NO: 80), spliced to create a junction of nucleotides 238 and 1047. The splice junction shifts the codons out of frame at nucleotide 1047 relative to the native reading frame of VEGFD, so that novel amino acids are produced from this point onward.

It was confirmed that the VEGF alternative splice forms were specific to the tumor and not found in normal tissue. For the HC2 20d2/c cell model, mRNA from NIH-3T3 cells was subjected to the same PCR conditions using the 3 nested sets of primers described above. NIH 3T3 cells are the cells from which HC2 20d2/c cell line was derived. Either no band or only the normally spliced mRNA was detected for mouse VEGF, VEGFB or VEGFD. Exemplary results are shown in FIG. 1B, which reveals that only the normally spliced VEGFD mRNA was present in NIH-3T3 cells.

For the MMTV-neu mouse tumor model (see Example 3, below), normal cells (fibroblasts) were isolated by explant culture as follows. Skin was excised from the mice, trypsinized and then placed into cell culture using DMEM with 5% fetal bovine serum as the culture media. Fibroblasts were allowed to migrate out from the excised skin and attach to the culture dish, whereupon they were propagated for 5-7 passages. The mRNA from the cultured fibroblasts was harvested, and subjected to the same PCR conditions as the mRNA isolated from MMTV mouse tumor cells using the three nested sets of PCR primers described above. PCR amplification of mRNA from normal MMTV-neu mouse cells revealed no band for the alternative splice form VEGFB, but showed an intact VEGFD band similar to that shown in FIG. 1B, representing the normally spliced mRNA.

The VEGF peptides listed above were synthesized by conventional methods. To avoid potential immune recognition of the normal VEGF family member, the VEGF peptides contained no more than 6 ordinarily contiguous amino acids from the corresponding normal protein. A peptide homodimer was made by adding a cysteine residue to the C-terminus of SEQ ID NO: 73 to give RTKPEKCDKPRRC (SEQ ID NO: 81). Dimerization was accomplished by controlled oxidation of the added C-terminal cysteine residues of SEQ ID NO: 81.

EXAMPLE 2

Regression of Tumors by Treatment with VEGF Peptides

The VEGF peptides and the SEQ ID NO: 85 homodimer were evaluated for their ability to elicit an anti-tumor immune response in a mouse tumor model. A total of 112 syngeneic mice were divided into eight treatment groups of 14 mice each, and injected with HC2 20d2/c tumor cells. Four days post-injection, the first through fifth treatment groups were vaccinated in the left inguinal area with 100 µg of either SEQ ID NO: 73, SEQ ID NO: 75, SEQ ID NO: 77, SEQ ID NO: 79, or the SEQ ID NO: 81 dimer diluted in 100 µl of PBS mixed with 45 ng of murine GM-CSF as an adjuvant. The total volume of phosphate buffered saline (PBS) was 150 microliters with 2 mg/ml mouse serum albumin as a carrier. The sixth treatment group was vaccinated as above with a combination of all four VEGF peptides and the SEQ ID NO: 81 homodimer (60 µg each) in a total of 200 microliters of PBS with 45 ng of murine GM-CSF and 2 mg/ml mouse serum albumin. The seventh treatment group was vaccinated as above with 100 µg of a peptide derived from a mutant epidermal growth factor receptor (EGFR) protein called EGFRvIII (SEQ ID NO: 82). The vaccine composition also contained 45 ng of murine GM-CSF and 2 mg/ml mouse serum albumin. The EGFRvIII mutation is the result of a genomic rearrangement in the EGFR gene, and the EGFRvIII peptide (SEQ ID NO: 82) is reported to induce an immune response against tumor cells expressing the mutant receptor. The eighth treatment group was vaccinated with GM-CSF and 2 mg/ml mouse serum albumin in PBS with no peptide, as a control. All treatment groups were then injected once daily for the next 3 days with the 45 ng GM-CSF in the original area of vaccination.

Figure 2:
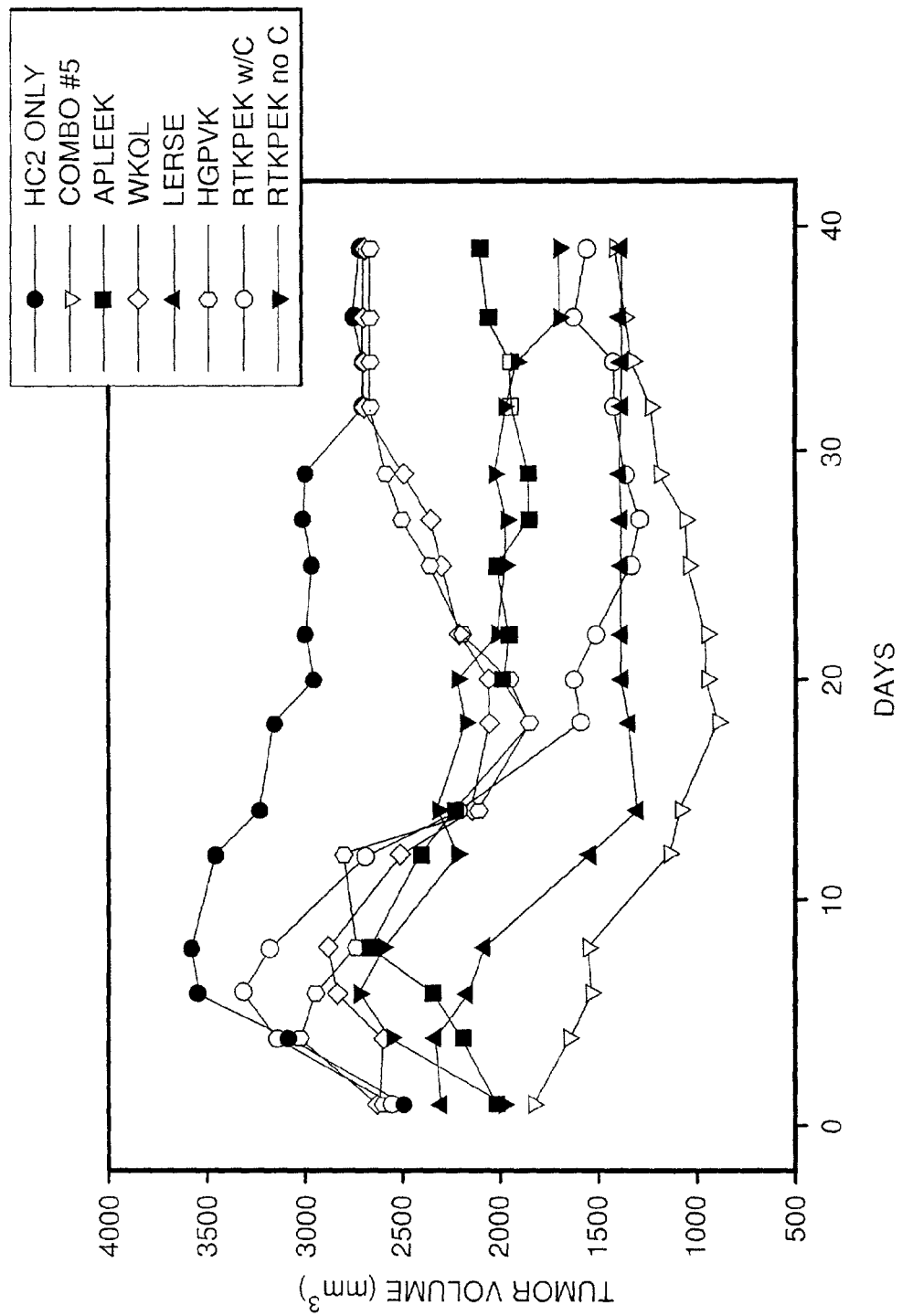
FIG. 2 is a plot of average tumor volumes in mm$^3$ vs. time in days for NIH-Swiss mice vaccinated with various immunogenic peptides derived from VEGF family alternative splice forms.

Mice that received GM-CSF alone exhibited on average a progression of tumors 5 days after vaccination, and then a moderate level of regression thereafter (FIG. 2, "HC2 only"). This regression is most likely due to spontaneous rejection of the mutant EGFRvIII protein which is expressed in HC2 20d2/c tumor cells. Mice that received the EGFRvIII peptide also exhibited progression of tumors for approximately 5 days, but the progression was not as dramatic as the control mice and there is distinct regression noted thereafter (FIG. 2, "APLEEK"). The regression pattern observed for EGFRvIII vaccination is similar to previous results obtained with this peptide. (Moscatello, D. K., *Cancer Research* 57:1419-1424, 1997).

FIG. 2 shows that all four of the monomeric VEGF peptides and the SEQ ID NO: 81 homodimer induce tumor regression to some degree, which is most notable 12 days after vaccination. For two of the peptides, SEQ ID NO: 75 and SEQ ID NO: 81 (FIG. 2, "VVKQL" and "HGPVK"), regression is seen until ~20 days after vaccination; the tumors, however, progress from that point onward. Mice vaccinated with the SEQ ID NO: 73 peptide synthesized without an additional cysteine (FIG. 2, "RTKPEK no C") exhibited a pattern of regression similar to that found for the EGFRvIII peptide. Mice vaccinated with the SEQ ID NO: 81 homodimer or the SEQ ID NO: 79 peptide (FIG. 2, "RTKPEK with C" and "LERSE") show a strong reduction in average tumor volumes by the end of the study, although SEQ ID NO: 81 homodimer treatment group initially shows tumor progression. Mice vaccinated with a combination of all four VEGF peptides and SEQ ID NO: 81 homodimer exhibit no tumor progression, and showed the greatest reduction in tumor volume of all treatment groups (FIG. 2, "Combo 5").

These results demonstrate that administering vaccine compositions comprising peptides based on VEGF family alternative splice forms elicit an effective anti-tumor immune response and causes tumor regression. Moreover, administration of a multimer or admixture of the VEGF peptides can further enhance the anti-tumor effect.

EXAMPLE 3

Delaying Onset of Breast Cancer Tumors by Treatment with VEGF Peptides

The ability of the VEGF peptides to prevent or delay the onset of tumors in MMTV-neu mice was evaluated. MMTV-neu mice are transgenic mice carrying an oncogenic form of the human neu oncogene under the control of the MMTV promoter, which drives expression of this oncogene in mammary tissue. 100% of female MMTV-neu mice develop multiple mammary tumors within 5-6 months of birth, which progress and eventually require sacrifice of the animal. Analysis of MMTV-neu mouse mammary tumors for VEGF family member alternative splice forms revealed alternative splice forms comprising the VEGF peptides SEQ ID NO: 73 and SEQ ID NO: 77.

Nine littermate MMTV-neu female mice were used in the experiment. One treatment group of three mice were initially vaccinated at 6 weeks of age with a combination of 60 micrograms each of SEQ ID NO: 73, SEQ ID NO: 77, and the SEQ ID NO: 81 homodimer with 45 ng of GM-CSF as the adjuvant. The mice are then vaccinated with the same composition at 5, 6, and 7 months of age. A control group of three mice received 45 ng GM-CSF alone as the adjuvant. A control group of three females received only 45 ng of GM-CSF. Both groups of mice were injected with 45 ng of GM-CSF at the original site of injection for an additional 3 days. This same cycle of vaccination was repeated at 5, 6, and 7 months of age. A second control group of three females received no treatment.

The results are given in FIG. 3, and show that untreated mice or mice given only GM-CSF develop tumors by 158 days after birth. All animals in both control groups had tumors by 192 days after, birth (FIG. 3A, "GM-CSF" and "No treatment"). In contrast, mice in the treatment group did not develop tumors until 192 days of age, and all animals in the treatment group did not have tumors until 226 days after birth (FIG. 3A, "Combo"). The total tumor volume per animal also revealed a difference in overall tumor burden between the treatment and control groups. By day 240, two of the untreated mice and one of the GM-CSF only mice attained total tumor volumes of greater than 3000 mm$^3$, necessitating sacrifice of the animals (FIG. 3B, "GM-CSF" and "No treatment"). However, in the treatment group the greatest tumor burden at day 240 was less than 1200 mm$^3$.

Thus, vaccination with compositions comprising VEGF peptides delayed the onset of tumor formation in a mouse model of human breast cancer, and resulted in a significantly reduced tumor burden.

EXAMPLE 4

Antibody Response in MMTV-Neu Mice Vaccinated with a Combination of VEGF Peptides A "dot blot" analysis was performed to assess whether an antibody response was generated in MMTV-neu mice which were vaccinated with a combination of VEGF peptides. Three female MMTV mice were injected with a combination of 60 micrograms each of SEQ ID NO: 73, SEQ ID NO: 77, and the SEQ ID NO: 81 homodimer with 45 ng of GM-CSF as the adjuvant (COMBO) as in Example 3. Three female MMTV-neu mice that were left untreated (No Treatment) and three female MMTV-neu mice that were injected with 45 ng GM-CSF alone (GM-CSF) were used as controls. The dot blots were prepared by separately spotting 1 microgram of BSA, SEQ ID NO: 82 ("EGFRvIII"), SEQ ID NO: 73 ("R-pep"), SEQ ID NO: 81 homodimer ("RC-pep"), SEQ ID NO: 81 ("H-pep"), SEQ ID NO: 79 ("L-pep") or SEQ ID NO: 75 ("V-pep") onto nitrocellulose membranes. One membrane was prepared for each experimental and control animal. The membranes were then incubated with serum taken from the appropriate control or experimental animal at 2 months after the last injection, and diluted 1:100. The membranes were then washed and incubated $^{125}$I anti-mouse secondary antibody, washed again and exposed to x-ray film.

Figure 4A:
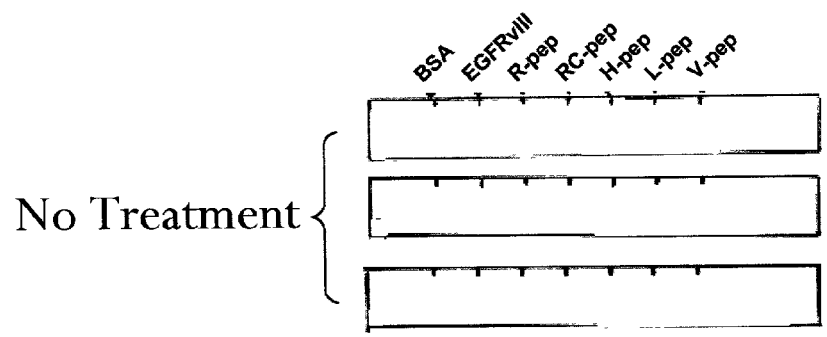
FIG. 4 shows autoradiographs of dot blots measuring the antibody response in MMTV-Neu mice which were A) left untreated ("No Treat"), B) given GMCSF alone ("GM-CSF"), or C) vaccinated with a combination of SEQ ID NO: 73, SEQ ID NO: 77 and SEQ ID NO: 81 and GM-CSF ("COMBO"). The antibody response in the mice was measured against 1 microgram of BSA, SEQ ID NO: 82 ("EG-FRvIII"), SEQ ID NO:73 ("R-pep"), SEQ ID NO: 81 homodimer ("RC-pep"), SEQ ID NO: 77 ("H-pep"), SEQ ID NO: 79 ("L-pep"), or SEQ ID NO: 75 ("V-pep") spotted onto nitrocellulose membranes.
Figure 4B:
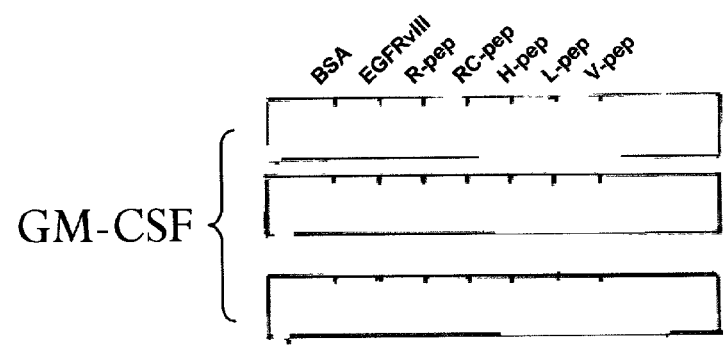
Figure 4C:
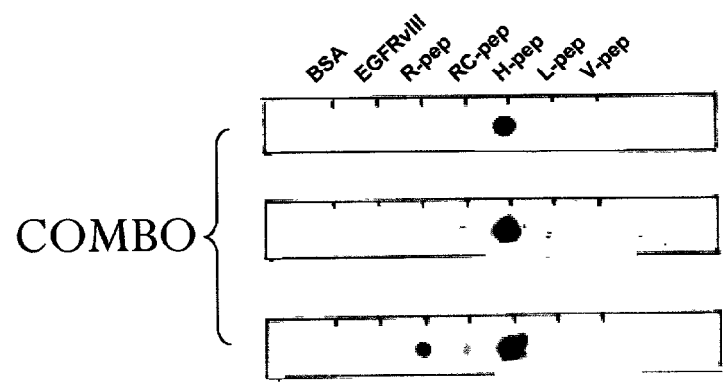

The untreated animals (No Treatment; FIG. 4A) or those that received GM-CSF alone (GM-CSF; FIG. 4B) did not show an antibody response against any VEGF or control peptide tested. In contrast, all three animals that had been immunized with SEQ ID NO: 73, SEQ ID NO: 77 and SEQ ID NO: 85 (COMBO; FIG. 4C) showed a strong antibody reaction against SEQ ID NO: 77. In addition, two of the animals demonstrated an antibody response against SEQ ID NO: 73 and SEQ ID NO: 81. However no animal from the immunized group showed an antibody reaction against the BSA control or the three control peptides (EGFRvIII, L-pep, and V-pep) with which the animals were not vaccinated.

EXAMPLE 5

Generation of Cytotoxic T Lymphocyte Activity by VEGF Peptides

An ELISPOT assay was performed to show that cytotoxic T lymphocyte activity was elicited by VEGF family peptides, as follows. Splenocytes were isolated from mice that were inoculated with HC2 20d2/c tumor cells and subsequently immunized with SEQ ID NO: 73 ("R-pep"), SEQ ID NO: 75 ("V-pep") or SEQ ID NO: 82 ("EGFRvIII") plus GM-CSF that showed tumor regression, or from a mouse inoculated with SEQ ID NO: 75 ("V-pep") and GM-CSF that showed no regression were evaluated in the assay. Splenocytes from mice inoculated with GM-CSF only were used as a control ("control"). HC2 20d2/c tumor cells pulsed with 10 micrograms/ml of the immunizing peptide, or mouse serum albumin (for splenocytes from GM-CSF only treated animals) were used as the target cells for the treatment and control splenocytes, respectively. Untreated HC2 20d2/c tumor cells were used as negative control target cells.

The splenocytes were incubated at various ratios (from 10:1 to 2:1) with target cells in triplicate, and lytic events were identified with an ELISPOT assay using anti-interferon-gamma antibody as the cytokine capture antibody. The specific spots per $10^6$ cells were quantitated using the lytic events from untreated target cells as the background, and then performing linear regression analysis. The results are shown in FIG. 5.

Figure 5:
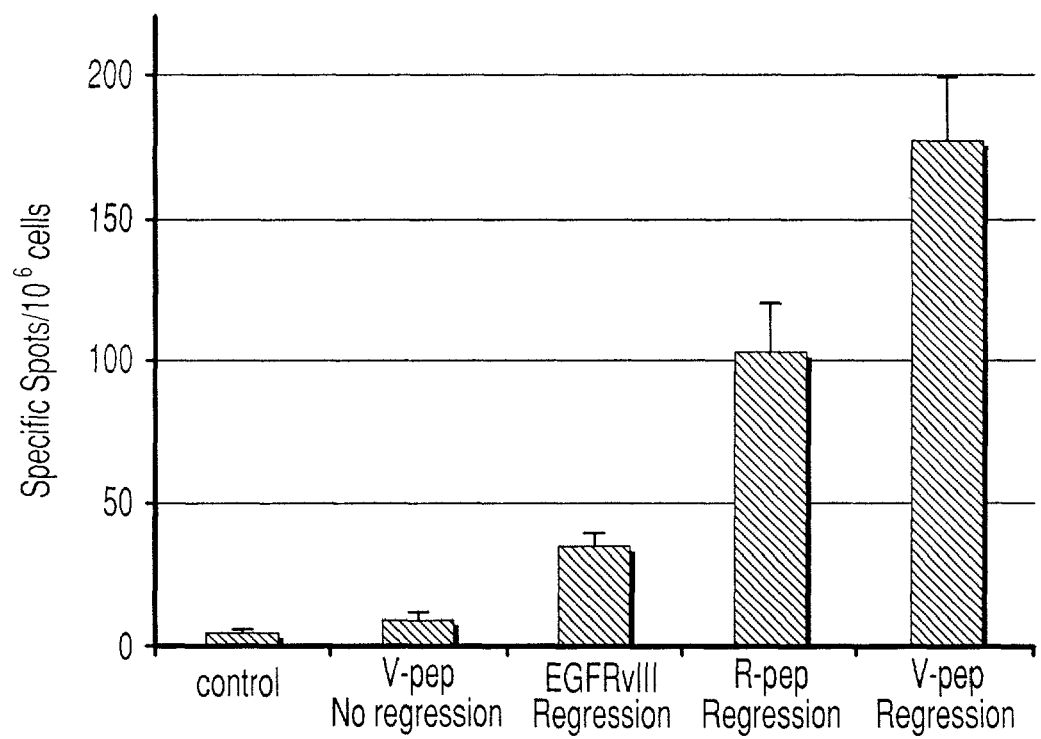
FIG. 5 is a plot showing lytic events identified using the ELISPOT assay with anti-interferon-gamma antibody. Splenocytes isolated from mice inoculated with HC2 20d2/c tumor cells and then immunized with SEQ ID NO: 73 ("R-pep"), SEQ ID NO: 75 ("V-pep") or SEQ ID NO: 82 ("EG-FRvIII") plus GM-CSF that showed tumor regression, or from a mouse inoculated with SEQ ID NO: 75 ("V-pep") and GM-CSF that showed no regression were evaluated in the assay. Mice inoculated with GM-CSF only were used as a control ("control").

FIG. 5 shows that the mice immunized with either SEQ ID NO: 73 ("R-pep") or SEQ ID NO: 75 ("V-pep") and which had undergone tumor regression had strong CTL responses when target cells were pulsed with the vaccinating peptide. These responses were greater than that seen for the mouse treated with SEQ ID NO: 82 ("EGFRvIII") which had undergone tumor regression. In contrast, splenocytes from the mouse treated with only GM-CSF, or the mouse vaccinated with SEQ ID NO: 73 ("V-pep"), neither of which had undergone tumor regression, showed poor CTL responses.

EXAMPLE 6

Generation of Cytotoxic T Lymphocyte Activity by Admixtures of VEGF Peptides An ELISPOT assay is performed to show that cytotoxic T lymphocyte activity is elicited by VEGF family peptides, as follows. Splenocytes are isolated from mice that are inoculated with HC2 20d2/c tumor cells and subsequently immunized with a combination of 60 micrograms each of SEQ ID NO: 73, SEQ ID NO: 77, and the SEQ ID NO: 81 homodimer with 45 ng of GM-CSF as the adjuvant, or SEQ ID NO: 82 ("EGFRvIII") plus 45 ng GM-CSF. Mice inoculated with GM-CSF only are used as a control ("control"). HC2 20d2/c tumor cells pulsed with 10 micrograms/ml of the immunizing peptides, mouse serum albumin (as positive control), or untreated HC2 20d2/c tumor cells (negative control) are used as the target cells. The splenocytes are incubated at various ratios (from 10:1 to 2:1) with target cells in triplicate, and lytic events are identified with an ELISPOT assay using anti-interferon-gamma antibody as the cytokine capture antibody. The specific spots per $10^6$ cells are quantitated using the lytic events from untreated target cells as the background, and then performing linear regression analysis.

The experiment is repeated with the following combinations of 60 micrograms each of the VEGF peptides as indicated:
1) SEQ ID NO: 73 and SEQ ID NO: 77;
2) SEQ ID NO: 77 and SEQ ID NO: 81; and
3) SEQ ID NO: 73; and SEQ ID NO: 81.

EXAMPLE 7

Tumor Prevention and Regression with Peptides, Multimeric Peptides, and Peptide Admixtures Peptides of the invention derived from the alternative splice forms associated with breast cancer, ovarian cancer, prostate cancer, lung cancer, skin cancer, lymphoma, bladder cancer, and pancreatic cancer are tested for their ability to either prevent tumors or induce the regression of tumors in experimental mouse models.

Mouse Models of Cancer

The mouse models used in the experiments are those in which the animals endogenously develop the relevant cancers or support the growth and tumorigenic properties of the relevant tumor-derived cell lines. For breast cancer, mice with a heterozygous deficiency for the pten gene or MMTV-neu transgenic mice are used; for ovarian cancer, mice with a heterozygous mutation in either BRCA1 or BRCA2 are used;

for prostate cancer, transgenic mice with the SV40 early gene under the control of the probasin promoter are used; for lymphoma, mice with a homozygous deficiency for the p53 or p19$^{ARF}$ gene are used; for bladder cancer, mice fed N-butyl-N-(-4-hydroxybutyl)-nitrosamine (BBN) are used. Mouse models of lung and bladder cancer can be obtained, respectively, by introducing cells from the Lewis lung carcinoma cell line or the PANC02 murine pancreatic adenocarcinoma cell line into an appropriate mouse strain. A mouse model of skin cancer can be obtained by inducing tumors in mice by topical application of DMBA (7,12-dimethylbenz[a]anthracene).

Tumor Prevention

Peptides of the invention which are associated with the cancers listed above are identified and synthesized as described above.

For those mouse models in which tumors are induced by a tumorigenic compound, or are produced from implanted tumor cells, the mice are initially vaccinated with approximately 50-500 micrograms of peptide mixed with 45 ng GM-CSF. The mice are then injected twice more with the same composition at intervals of 2 to 4 weeks. Mice receiving GM-CSF only are used as a control. After the third injection, the mice are inoculated with tumor cells or exposed to a tumorigenic compound in a dose known to produce tumors at a high incidence (i.e., in 75% to 90% or greater of the animals) in that particular host. The mice are then monitored for the time to first presentation of tumor, and the sizes of the tumors are measured every other day thereafter.

For those mouse models which spontaneously develop tumors, an initial vaccination with approximately 50-500 micrograms of peptide mixed with 45 ng GM-CSF is given at 6 weeks of age, the time at which the immune system is developed in mice, and then at 2 to 4 week intervals thereafter. Mice receiving GM-CSF only are used as a control. The mice are then monitored for the time to first presentation of tumor, and the sizes of the tumors are measured every other day thereafter.

Tumor Regression

Peptides of the invention which are associated with the cancers listed above are identified and synthesized as described above.

For those mouse models in which tumors are induced by a tumorigenic compound, or are produced from implanted tumor cells, mice are initially inoculated with tumor cells or exposed to the tumorigenic compound. At a time period approximately four days prior to when tumors are expected to develop, the mice are vaccinated with approximately 50-500 micrograms of peptide mixed with 45 ng GM-CSF and injected twice more with the same composition at intervals of 2 to 4 weeks. Mice receiving GM-CSF only are used as a control. The mice are monitored for the time to first presentation of tumor, and the sizes of the tumors are measured every other day thereafter.

For those mouse models which spontaneously develop tumors, an initial vaccination with approximately 50-500 micrograms of peptide mixed with 45 ng GM-CSF is given at 6 weeks of age, the time at which the immune system is developed in mice, and then at 2 to 4 week intervals thereafter. Mice receiving GM-CSF only are used as a control. The mice are monitored for the time to first presentation of tumor, and the sizes of the tumors are measured every other day thereafter.

Tumor Prevention and Regression with Multimeric Peptides

The experiments described above for demonstrating tumor prevention and regression in mouse models of cancer are repeated using dimeric, trimeric, tetrameric, pentameric or hexameric peptides of the invention which are associated with the particular cancer.

Tumor Prevention and Regression with Peptide Admixtures

The experiments described above for demonstrating tumor prevention and regression in mouse models of cancer are repeated using admixtures of two, three, four, five or six peptides of the invention which are associated with the particular cancer.

EXAMPLE 8

Prevention or Regression of Tumors Formed by Syngeneic Mouse Tumor Cells Expressing Human Alternative Splice Forms Peptides of the invention of human origin associated with a cancer, as listed in Table 1, are identified and synthesized as described above. Expression vectors capable of expressing some or all of the human alternative splice form sequences from which the vaccinating peptides are derived are constructed according to standard techniques.

Syngeneic Mouse Tumor Model

An NIH-3T3 cell line is transfected with the SV40 T antigen to render it tumorigenic. Alternatively, an NIH-3T3 cell line is rendered tumorigenic by being maintained continuously in cell culture for 30-40 passages, and tumorigenic cells which spontaneously arise are isolated and propagated.

The tumorigenic NIH-3T3 cells are transfected with the plasmid expression vector described above, and cells expressing the human alternative splice form sequences are selected and propagated by standard techniques. Tumorigenic NIH-3T3 cells expressing the human alternative splice form sequences are injected into NIH Swiss mice, and tumors are allowed to form. The tumors are excised from some animals and propagated in cell culture, where the cells maintain their ability to form tumors in animals. Expression of the human sequences is confirmed. These cells are then used in subsequent tumor prevention/regression experiments.

Tumor Prevention

NIH Swiss mice are initially vaccinated with approximately 50-500 micrograms of one or more peptides of the invention of human origin described above, mixed with 45 ng GM-CSF. The mice are then injected twice more with the same composition at intervals of 2 to 4 weeks. Mice receiving GM-CSF only are used as a control. After the third injection, the mice are inoculated with syngeneic tumor cells expressing human alternative splice form sequences, as described above. The mice are then monitored for the time to first presentation of tumor, and the sizes of the tumors are measured every other day thereafter.

Tumor Regression

NIH Swiss mice are initially inoculated with syngeneic tumor cells expressing the human alternative splice form, as described above. On the fourth day post inoculation, the mice are vaccinated with approximately 50-500 micrograms of one or more peptides of the invention of human origin described above, mixed with 45 ng GM-CSF. The mice are injected twice more with the same composition at intervals of 2 to 4 weeks. Mice receiving GM-CSF only are used as a control. The mice are monitored for the time to first presentation of tumor, and the sizes of the tumors are measured every other day thereafter.

All documents referred to herein are incorporated by reference in their entirety. While the present invention has been described in connection with the preferred embodiments and the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

I claim:

1. A method of treating cancer in a human subject in which diseased or abnormal cells produce at least one alternative splice form, which alternative splice form is substantially absent from normal cells, comprising administering an effective amount of at least one human vascular endothelial growth factor (VEGF) peptide to the subject, such that an immune response generated against the diseased or abnormal cells treats said cancer in the subject;
    wherein said human VEGF peptide comprises an amino acid sequence unique to said alternative splice form,
    wherein the peptide comprises no more than seven contiguous amino acids from a normally spliced product of a VEGF gene, and
    wherein the alternative splice form is produced from a VEGF gene.

2. The method of claim 1, wherein the immune response is an MHC HLA-class I or class II restricted cytotoxic T lymphocyte response, or an antibody response.

3. The method of claim 2, wherein the cytotoxic T lymphocyte response is a CD8+ T lymphocyte response wherein CD8+, MHC class I-restricted T lymphocytes are activated.

4. The method of claim 2, wherein the cytotoxic T lymphocyte response is a CD4+ T lymphocyte response wherein CD4+, MHC class II-restricted T lymphocytes are activated.

5. The method of claim 1, wherein one L-amino acid of the peptide is replaced with a D-amino acid.

6. The method of claim 1, wherein two or more peptides are administered to the subject.

7. The method of claim 6, wherein the two or more peptides comprise a multimer.

8. The method of claim 7, wherein the multimer is a homomultimer.

9. The method of claim 8, wherein the multimer is selected from the group consisting of a dimer; trimer; tetramer; pentamer; and hexamer.

10. The method of claim 9, wherein the multimer is a dimer.

11. The method of claim 7, wherein the multimer is a heteromultimer.

12. The method of claim 11, wherein the multimer is selected from the group consisting of a dimer; trimer; tetramer; pentamer; and hexamer.

13. The method of claim 6, wherein the two or more peptides comprise an admixture.

14. The method of claim 6, wherein the two or more peptides comprise overlapping epitopes from one or more alternative splice forms.

15. The method of claim 1, wherein the at least one peptide is administered to the subject in combination with peptides that present T-helper cell epitopes.

16. The method of claim 1, wherein the at least one peptide is administered to the subject in combination with at least one component that primes cytotoxic T lymphocytes.

17. The method of claim 16, wherein the at least one component that primes cytotoxic T lymphocytes comprises tripalmitoyl-S-glycerylcysteinly-seryl-serine (P3CSS).

18. The method of claim 1, wherein the effective amount is about 1 microgram to about 2,000 mg of the at least one peptide per 70 kg of subject.

19. The method of claim 1, wherein the effective amount is about 1 microgram to about 500 mg of the at least one peptide per 70 kg of subject.

20. The method of claim 1, wherein the effective amount is about 10 micrograms to about 200 mg of the at least one peptide per 70 kg of subject.

21. The method of claim 1, wherein the effective amount is about 50 micrograms to about 100 mg of the at least one peptide per 70 kg of subject.

22. The method of claim 1, wherein the effective amount of the at least one peptide is administered in a single dose.

23. The method of claim 1, wherein the effective amount of the at least one peptide is administered in multiple doses.

24. The method of claim 1, wherein the effective amount of the at least one peptide is administered enterally.

25. The method of claim 24, wherein the enteral route of administration is selected from the group consisting of oral; rectal; and intranasal.

26. The method of claim 1, wherein the effective amount of the at least one peptide is administered parenterally.

27. The method of claim 26, wherein the parenteral route of administration is selected from the group consisting of intravenous; intramuscular; intraarterial; intraperitoneal; intravaginal; intravesical; intradermal; intrapulmonary; inhalation; topical; subcutaneous; and instillation into the body.

28. The method of claim 1, wherein the at least one peptide is administered to a subject in combination with a carrier or adjuvant.

29. The method of claim 28, wherein the carrier is selected from the group consisting of keyhole limpet hemocyanin; thyroglobulin; albumins; tetanus toxoid; and polyamino acids.

30. The method of claim 28, wherein the adjuvant is selected from the group consisting of complete Freund's adjuvant; incomplete Freund's adjuvant; aluminum phosphate; aluminum hydroxide; polylecithins; emulsified oils; and alum.

31. The method of claim 1, wherein the at least one peptide is administered to a subject in combination with an immunostimulatory compound.

32. The method of claim 31, wherein the immunostimulatory compound is selected from the group consisting of cytokines and haptens.

33. The method of claim 32, where the cytokines are selected from the group consisting of GM-CSF; IL-12; IL-2; IL-4; IL-1α; and IL-18.

34. The method of claim 1, wherein the cancer is selected from the group consisting of acute promyelocytic leukemia; acute lymphoblastic leukemia; myeloblastic leukemia; uterine cancer; thyroid cancer; gastrointestinal cancer; dysplastic and neoplastic cervical epithelium; melanoma; endometrial cancer; teratocarcinoma; colon cancer; desmoplastic round cell tumors; gastric cancer; breast cancer; ovarian cancer; prostate cancer; lung cancer; skin cancer; lymphoma; bladder cancer; and pancreatic cancer.

35. The method of claim 1, wherein said administering at least one peptide to a subject comprises the steps of:
    (1) removing immune system effector cells from a subject;
    (2) maintaining the immune system effector cells in culture outside the body of the subject;
    (3) optionally enriching the immune system effector cells for a particular immune system effector cell type;
    (4) treating the cultured immune system effector cells with the at least one peptide;
    (5) optionally examining a portion of the treated immune system effector cells to confirm the presence of the at least one peptide within the cells; and
    (6) reintroducing the treated immune system effector cells into the subject.

36. The method of claim 35, wherein treatment of the immune system effector cells with the at least one peptide comprises direct exposure of the cells to the at least one peptide.

37. The method of claim 35, wherein the treated immune system effector cells are reintroduced into the subject by intravenous infusion or direct injection into the bone marrow.

38. The method of claim 35, wherein about $10^5$ to about $10^8$ treated immune system effector cells per kilogram of subject body weight are reintroduced into the subject.

* * * * *